US012318436B2

United States Patent
Kramer et al.

(10) Patent No.: US 12,318,436 B2
(45) Date of Patent: Jun. 3, 2025

(54) COMPOSITION AND METHOD FOR SPRAY DRYING AN ADJUVANT VACCINE EMULSION

(71) Applicant: ACCESS TO ADVANCED HEALTH INSTITUTE, Seattle, WA (US)

(72) Inventors: Ryan Kramer, Lynnwood, WA (US); Michelle Archer, Seattle, WA (US); Christopher Fox, Sumner, WA (US); Reinhard Vehring, Edmonton (CA); Mani Ordoubadi, Edmonton (CA); Mellissa Gomez, Leduc (CA); Nicholas Carrigy, Sherwood Park (CA)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 564 days.

(21) Appl. No.: 17/612,893

(22) PCT Filed: May 26, 2020

(86) PCT No.: PCT/US2020/034595
§ 371 (c)(1),
(2) Date: Nov. 19, 2021

(87) PCT Pub. No.: WO2020/243115
PCT Pub. Date: Dec. 3, 2020

(65) Prior Publication Data
US 2022/0249646 A1    Aug. 11, 2022

Related U.S. Application Data

(60) Provisional application No. 62/852,983, filed on May 25, 2019.

(51) Int. Cl.
| | | |
|---|---|---|
| *A61K 39/04* | (2006.01) | |
| *A61K 9/00* | (2006.01) | |
| *A61K 31/7016* | (2006.01) | |
| *A61K 39/39* | (2006.01) | |
| *A61K 47/44* | (2017.01) | |
| *A61P 11/00* | (2006.01) | |
| *A61K 39/00* | (2006.01) | |

(52) U.S. Cl.
CPC ............ *A61K 39/04* (2013.01); *A61K 9/0075* (2013.01); *A61K 31/7016* (2013.01); *A61K 39/39* (2013.01); *A61K 47/44* (2013.01); *A61P 11/00* (2018.01); *A61K 2039/543* (2013.01); *A61K 2039/544* (2013.01); *A61K 2039/55572* (2013.01)

(58) Field of Classification Search
CPC ...... A61K 39/04; A61K 9/0075; A61K 47/44; A61P 11/00
See application file for complete search history.

(56) References Cited

FOREIGN PATENT DOCUMENTS

| | | | | |
|---|---|---|---|---|
| JP | 2017-502962 A | 7/2015 | | |
| WO | WO-2009046440 A1 * | 4/2009 | ............ | A61K 35/74 |
| WO | 2009108689 A1 | 9/2009 | | |
| WO | 2015-103167 A2 | 7/2015 | | |
| WO | 2019010560 A1 | 1/2019 | | |
| WO | 2020243115 A1 | 12/2020 | | |

OTHER PUBLICATIONS

Oster et al. 2005 (Comparative study of DNA encapsulation into PLGA microparticles using modified double emulsion methods and spray drying techniques; Journal of Microencapsulation 22(3): 235-244. (Year: 2005).*
Encina et al. 2016 (Conventional spray-drying and future trends for the microencapsulation of fish oil; Trends in Food Science & Technology; 56: 46-60 (Year: 2016).*
R. Vehring, "Pharmaceutical Particle Engineering via Spray Drying" Pharmaceutical Research, vol. 25, No. 5, pp. 999-1022, 2007.
C. Encina et al., "Conventional spray-drying and future trends for the microencapsulation of fish oil," Trends in Food Science & Technology, vol. 56, pp. 46-60, 2016.
S. Bertholet et al., "A defined tuberculosis vaccine candidate boosts BCG and protects against multidrug-resistant *Mycobaterium tuberculosis*," Science Translational Medicine, vol. 2, No. 53, pp. 53-74, 2010.
W. H. Organization, "Global Tuberculosis Report," World Health Organization, Geneva, 2018.
R. N. Coleret al., "The TLR-4 agonist adjuvant, GLA-SE, improves magnitude and quality of immune responses elicited by the ID93 tuberculosis vaccine: first-in-human trial," Nature Partner Journals, vol. 3, No. 34, 2018.
C. B. Fox et al., "Monitoring the effects of component structure and source on formulation stability and adjuvant activity of oil-in-water emulsions," Colloids and Surfaces B; Biointerfaces, vol. 65, pp. 98-105, 2008.
A. G. Floyd, "Top ten considerations in the development of parenterial emulsions," Pharmaceutical Science and Technology Today, vol. 2, No. 4, pp. 134-143, 1999.
R. M. Kramer et al., "Development of a thermostable nanoemulsion adjuvanted vaccine against tuberculosis using a design-of-experiments approach," International Journal of Nanomedicine, vol. 13, pp. 3689-3711, 2018.
M. T. Orr et al., "Elimination of the cold-chain dependance of a nanoemulsion adjuvant vaccine against tuberculois by lyophilization," Journal of Controlled Release, vol. 10, No. 177, pp. 20-26, 2014.

(Continued)

*Primary Examiner* — Mary Maille Lyons
(74) *Attorney, Agent, or Firm* — Benjamin Keim; Newport IP, LLC

(57) ABSTRACT

The invention provides for thermostable spray dried formulations including vaccines and pharmaceutical compositions for inducing or enhancing an immune response and methods of use thereof. The spray dried formulations are a dry powder generally comprising an antigen and/or an adjuvant, a metabolizable oil, and one or more excipients.

36 Claims, 8 Drawing Sheets

Specification includes a Sequence Listing.

(56) References Cited

OTHER PUBLICATIONS

H. Schwartzbach, "Achieving aseptic drying with spray drying technologies," Pharmaceutical Technology Europe, vol. 23, No. 9, 2011.
International Conference On Harmonisation Of Technical Requirements For Registration Of Pharmaceuticals For Human Use, "ICH Harmonised Tripartite Guideline—Stability Testing of New Drug Substances and Products Q1A (R2)," ICH, 2003.
S. Ohtake et al., "Trehalose: current use and future applications," Journal of Pharmaceutical Sciences, vol. 100, No. 6, pp. 2020-2053, 2011.
D. Zhou et al., "Physical stability of amorphous pharmaceuticals: Importance of configurational thermodynamic quantities and molecular mobility," Journal of Pharmaceutical Sciences, vol. 91, No. 8, pp. 1863-1872, Aug. 2002.
M. Gordon et al., "Ideal copolymers and the second-order transitions of synthetic rubbers. i. non-crystalline copolymers," Journal of Applied Chemistry, vol. 2, No. 9, pp. 493-500, Sep. 1952.
T. Chen et al., "Literature review: supplemented phase diagram of the trehalose-water binary mixture," Cryobiology, vol. 40, No. 3, pp. 277-282, 2000.
H. A. Iglesias et al., "Adsorption isotherm of amorphous trehalose," Journal of the Science of Food and Agriculture, vol. 75, No. 2, pp. 183-186, Mar. 26, 1999.
K. D. Roe et al., "Glass transition and crystallization of amorphous trehalose-sucrose mixtures," International Journal of Food Properties, vol. 8, No. 3, pp. 559-574, 2005.
R. Vehring et al., "Particle formation in spray drying," Aerosol Science, vol. 38, pp. 728-746, 2007.
J. Ivey et al., "Dried corticosteroid particle formation from evaporating monodisperse propellant solution droplets," in AAPS Annual Meeting and Exposition, Denver, 1 page, 2016.
S. Hoe et al., "Use of a fundamental approach to spray-drying formulation design to facilitate the development of multi-component dry powder aerosols for respiratory drug delivery," Pharmaceutical Research, vol. 32, No. 2, pp. 449-465, Feb. 2014.
M. Y. Chan et al., "Particle sizing of nanoparticle adjuvant formulations by dynamic light scattering (DLS) and nanoparticle tracking analysis (NTA)," Methods in Molecular Biology, vol. 1494, pp. 239-252, 2017.
H. Wang et al., "Macro-Raman spectroscopy for bulk composition and homogeneity analysis of multi-component pharmaceutical powders," Journal of Pharmaceutical and Biomedical Analysis, vol. 141, pp. 180-191, 2017.
C. Krogsgard Nielsen et al., "Enhancing the antibacterial efficacy of isoeugenol by emulsion encapsulation," International Journal of Food Microbiology, vol. 229, pp. 7-14, 2016.
N. Mlalila et al., "Effects of spray-drying on w/o/w multiple emulsions prepared from a stearic acid matrix," Nanotechnology, Science and Applications, vol. 7, pp. 105-112, 2014.
C. Lee et al., "Raman spectra of planar supported lipid bilayers," Biochimica et Biophysica Acta, vol. 1711, No. 1, pp. 59-71, Jun. 2005.
M. Bringas-Lantigua et al., "Influence of spray-dryer air temperatures on encapsulated mandarin oil," Drying Technology, vol. 29, No. 5, pp. 520-526, 2011.
Office Action for related patent application from China CIPO, application No. 202080048526, mailed Sep. 28, 2023, 17 pages (with translation).
Office Action for related matter Chinese Application No. 2020800485256 dated May 1, 2024, 13 pages.
PCT/US2020/034595—International Search Report and Written Opinion, mailed Sep. 22, 2020, 14 pages.
L. Garcia-Contreras et al., "Immunization by a Bacterial Aerosol", Proceedings of the National Academy of Sciences, vol. 105, No. 12, Mar. 25, 2008, pp. 4656-4660.
Office Action for related matter Japan Patent Application No. 2021-569917, dated Aug. 1, 2024, 7 pages (with translation).
Kanojia, et al., "Developments in the formulation and delivery of spray dried vaccines", Human Vaccines & Immunotherapeutics, 13:10, 2364-2378, Oct. 18, 2017, 17 pages.
Munoz,-Ibanez, et al., "Changes in oil-in-water emulsion size distribution during the atomization step in speay-drying encapsulation," Journal of Food Engineering, 167, Feb. 7, 2015, 122-132.
Related matter CN Patent Application No. 2020800485256 mailed Oct. 23, 2024, 8 pages.
Related family patent Decision of Refusal for Japanese Patent Application No. 2021-569917, dated Feb. 26, 2025, 8 pages (including translation).
Kanojia, G. et al., "Developments in the formulation and delivery of spray dried vaccines", Human Vaccines & Immunotherapies, 2017, vol. 13, No. 10, pp. 2364-2378.
Munoz-Ibanez, M. et al., "Changes in oil-in-water emulsion size distribution during the atomization step in spray-drying encapsulation", Journal of Food Engineering, 2015, vol. 167, pp. 122-132.

\* cited by examiner

SEQUENCE LISTING

<160> NUMBER OF SEQ ID NOS: 8

<210> SEQ ID NO 1
<211> LENGTH: 911
<212> TYPE: PRT
<213> ORGANISM: Mycobacterium tuberculosis

<400> SEQUENCE: 1

```
Met Gly Ser Ser His His His His His Ser Gly Leu Val Pro
1               5                   10                  15

Arg Gly Ser His Met Thr Ile Asn Tyr Gln Phe Gly Asp Val Asp Ala
            20                  25                  30

His Gly Ala Met Ile Arg Ala Gln Ala Gly Ser Leu Glu Ala Glu His
                35                  40                  45

Gln Ala Ile Ile Ser Asp Val Leu Thr Ala Ser Asp Phe Trp Gly Gly
        50                  55                  60

Ala Gly Ser Ala Ala Cys Gln Gly Phe Ile Thr Gln Leu Gly Arg Asn
65                  70                  75                  80

Phe Gln Val Ile Tyr Glu Gln Ala Asn Ala His Gly Gln Lys Val Gln
                85                  90                  95

Ala Ala Gly Asn Asn Met Ala Gln Thr Asp Ser Ala Val Gly Ser Ser
            100                 105                 110

Trp Ala Gly Thr His Leu Ala Asn Gly Ser Met Ser Glu Val Met Met
            115                 120                 125

Ser Glu Ile Ala Gly Leu Pro Ile Pro Pro Ile Ile His Tyr Gly Ala
        130                 135                 140

Ile Ala Tyr Ala Pro Ser Gly Ala Ser Gly Lys Ala Trp His Gln Arg
145                 150                 155                 160

Thr Pro Ala Arg Ala Glu Gln Val Ala Leu Glu Lys Cys Gly Asp Lys
                165                 170                 175

Thr Cys Lys Val Val Ser Arg Phe Thr Arg Cys Gly Ala Val Ala Tyr
            180                 185                 190

Asn Gly Ser Lys Tyr Gln Gly Gly Thr Gly Leu Thr Arg Arg Ala Ala
        195                 200                 205

Glu Asp Asp Ala Val Asn Arg Leu Glu Gly Gly Arg Ile Val Asn Trp
    210                 215                 220

Ala Cys Asn Glu Leu Met Thr Ser Arg Phe Met Thr Asp Pro His Ala
225                 230                 235                 240

Met Arg Asp Met Ala Gly Arg Phe Glu Val His Ala Gln Thr Val Glu
                245                 250                 255

Asp Glu Ala Arg Arg Met Trp Ala Ser Ala Gln Asn Ile Ser Gly Ala
            260                 265                 270

Gly Trp Ser Gly Met Ala Glu Ala Thr Ser Leu Asp Thr Met Thr Gln
        275                 280                 285

Met Asn Gln Ala Phe Arg Asn Ile Val Asn Met Leu His Gly Val Arg
    290                 295                 300

Asp Gly Leu Val Arg Asp Ala Asn Asn Tyr Glu Gln Gln Glu Gln Ala
305                 310                 315                 320

Ser Gln Gln Ile Leu Ser Ser Val Asp Ile Asn Phe Ala Val Leu Pro
                325                 330                 335

Pro Glu Val Asn Ser Ala Arg Ile Phe Ala Gly Ala Gly Leu Gly Pro
            340                 345                 350

Met Leu Ala Ala Ala Ser Ala Trp Asp Gly Leu Ala Glu Glu Leu His
        355                 360                 365
```

```
Ala Ala Ala Gly Ser Phe Ala Ser Val Thr Thr Gly Leu Ala Gly Asp
        370             375                 380
Ala Trp His Gly Pro Ala Ser Leu Ala Met Thr Arg Ala Ala Ser Pro
385                 390                 395                 400
Tyr Val Gly Trp Leu Asn Thr Ala Ala Gly Gln Ala Ala Gln Ala Ala
                405                 410                 415
Gly Gln Ala Arg Leu Ala Ala Ser Ala Phe Glu Ala Thr Leu Ala Ala
                420                 425                 430
Thr Val Ser Pro Ala Met Val Ala Ala Asn Arg Thr Arg Leu Ala Ser
            435                 440                 445
Leu Val Ala Ala Asn Leu Leu Gly Gln Asn Ala Pro Ala Ile Ala Ala
        450                 455                 460
Ala Glu Ala Glu Tyr Glu Gln Ile Trp Ala Gln Asp Val Ala Ala Met
465                 470                 475                 480
Phe Gly Tyr His Ser Ala Ala Ser Ala Val Ala Thr Gln Leu Ala Pro
                485                 490                 495
Ile Gln Glu Gly Leu Gln Gln Gln Leu Gln Asn Val Leu Ala Gln Leu
                500                 505                 510
Ala Ser Gly Asn Leu Gly Ser Gly Asn Val Gly Val Gly Asn Ile Gly
            515                 520                 525
Asn Asp Asn Ile Gly Asn Ala Asn Ile Gly Phe Gly Asn Arg Gly Asp
        530                 535                 540
Ala Asn Ile Gly Ile Gly Asn Ile Gly Asp Arg Asn Leu Gly Ile Gly
545                 550                 555                 560
Asn Thr Gly Asn Trp Asn Ile Gly Ile Gly Ile Thr Gly Asn Gly Gln
                565                 570                 575
Ile Gly Phe Gly Lys Pro Ala Asn Pro Asp Val Leu Val Val Gly Asn
                580                 585                 590
Gly Gly Pro Gly Val Thr Ala Leu Val Met Gly Gly Thr Asp Ser Leu
            595                 600                 605
Leu Pro Leu Pro Asn Ile Pro Leu Leu Glu Tyr Ala Ala Arg Phe Ile
        610                 615                 620
Thr Pro Val His Pro Gly Tyr Thr Ala Thr Phe Leu Glu Thr Pro Ser
625                 630                 635                 640
Gln Phe Phe Pro Phe Thr Gly Leu Asn Ser Leu Thr Tyr Asp Val Ser
                645                 650                 655
Val Ala Gln Gly Val Thr Asn Leu His Thr Ala Ile Met Ala Gln Leu
            660                 665                 670
Ala Ala Gly Asn Glu Val Val Phe Gly Thr Ser Gln Ser Ala Thr
        675                 680                 685
Ile Ala Thr Phe Glu Met Arg Tyr Leu Gln Ser Leu Pro Ala His Leu
        690                 695                 700
Arg Pro Gly Leu Asp Glu Leu Ser Phe Thr Leu Thr Gly Asn Pro Asn
705                 710                 715                 720
Arg Pro Asp Gly Gly Ile Leu Thr Arg Phe Gly Phe Ser Ile Pro Gln
                725                 730                 735
Leu Gly Phe Thr Leu Ser Gly Ala Thr Pro Ala Asp Ala Tyr Pro Thr
                740                 745                 750
Val Asp Tyr Ala Phe Gln Tyr Asp Gly Val Asn Asp Phe Pro Lys Tyr
            755                 760                 765
Pro Leu Asn Val Phe Ala Thr Ala Asn Ala Ile Ala Gly Ile Leu Phe
        770                 775                 780
Leu His Ser Gly Leu Ile Ala Leu Pro Pro Asp Leu Ala Ser Gly Val
```

```
            785                 790                 795                 800
Val Gln Pro Val Ser Ser Pro Asp Val Leu Thr Thr Tyr Ile Leu Leu
                    805                 810                 815

Pro Ser Gln Asp Leu Pro Leu Leu Val Pro Leu Arg Ala Ile Pro Leu
                    820                 825                 830

Leu Gly Asn Pro Leu Ala Asp Leu Ile Gln Pro Asp Leu Arg Val Leu
                    835                 840                 845

Val Glu Leu Gly Tyr Asp Arg Thr Ala His Gln Asp Val Pro Ser Pro
    850                 855                 860

Phe Gly Leu Phe Pro Asp Val Asp Trp Ala Glu Val Ala Ala Asp Leu
865                 870                 875                 880

Gln Gln Gly Ala Val Gln Val Asn Asp Ala Leu Ser Gly Leu Gly
                    885                 890                 895

Leu Pro Pro Pro Trp Gln Pro Ala Leu Pro Arg Leu Phe Ser Thr
                900                 905                 910

<210> SEQ ID NO 2
<211> LENGTH: 891
<212> TYPE: PRT
<213> ORGANISM: Mycobacterium tuberculosis

<400> SEQUENCE: 2

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
                20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
        50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala Gly Thr
                85                  90                  95

His Leu Ala Asn Gly Ser Met Ser Glu Val Met Met Ser Glu Ile Ala
            100                 105                 110

Gly Leu Pro Ile Pro Pro Ile Ile His Tyr Gly Ala Ile Ala Tyr Ala
        115                 120                 125

Pro Ser Gly Ala Ser Gly Lys Ala Trp His Gln Arg Thr Pro Ala Arg
    130                 135                 140

Ala Glu Gln Val Ala Leu Glu Lys Cys Gly Asp Lys Thr Cys Lys Val
145                 150                 155                 160

Val Ser Arg Phe Thr Arg Cys Gly Ala Val Ala Tyr Asn Gly Ser Lys
                165                 170                 175

Tyr Gln Gly Gly Thr Gly Leu Thr Arg Arg Ala Ala Glu Asp Asp Ala
            180                 185                 190

Val Asn Arg Leu Glu Gly Gly Arg Ile Val Asn Trp Ala Cys Asn Glu
        195                 200                 205

Leu Met Thr Ser Arg Phe Met Thr Asp Pro His Ala Met Arg Asp Met
    210                 215                 220

Ala Gly Arg Phe Glu Val His Ala Gln Thr Val Glu Asp Glu Ala Arg
225                 230                 235                 240

Arg Met Trp Ala Ser Ala Gln Asn Ile Ser Gly Ala Gly Trp Ser Gly
                245                 250                 255
```

```
Met Ala Glu Ala Thr Ser Leu Asp Thr Met Thr Gln Met Asn Gln Ala
                260                 265                 270

Phe Arg Asn Ile Val Asn Met Leu His Gly Val Arg Asp Gly Leu Val
            275                 280                 285

Arg Asp Ala Asn Asn Tyr Glu Gln Gln Glu Gln Ala Ser Gln Gln Ile
        290                 295                 300

Leu Ser Ser Val Asp Ile Asn Phe Ala Val Leu Pro Pro Glu Val Asn
305                 310                 315                 320

Ser Ala Arg Ile Phe Ala Gly Ala Gly Leu Pro Met Leu Ala Ala
                325                 330                 335

Ala Ser Ala Trp Asp Gly Leu Ala Glu Glu Leu His Ala Ala Gly
                340                 345                 350

Ser Phe Ala Ser Val Thr Thr Gly Leu Ala Gly Asp Ala Trp His Gly
                355                 360                 365

Pro Ala Ser Leu Ala Met Thr Arg Ala Ala Ser Pro Tyr Val Gly Trp
    370                 375                 380

Leu Asn Thr Ala Ala Gly Gln Ala Ala Gln Ala Ala Gly Gln Ala Arg
385                 390                 395                 400

Leu Ala Ala Ser Ala Phe Glu Ala Thr Leu Ala Ala Thr Val Ser Pro
                405                 410                 415

Ala Met Val Ala Ala Asn Arg Thr Arg Leu Ala Ser Leu Val Ala Ala
                420                 425                 430

Asn Leu Leu Gly Gln Asn Ala Pro Ala Ile Ala Ala Glu Ala Glu
            435                 440                 445

Tyr Glu Gln Ile Trp Ala Gln Asp Val Ala Ala Met Phe Gly Tyr His
    450                 455                 460

Ser Ala Ala Ser Ala Val Ala Thr Gln Leu Ala Pro Ile Gln Glu Gly
465                 470                 475                 480

Leu Gln Gln Gln Leu Gln Asn Val Leu Ala Gln Leu Ala Ser Gly Asn
                485                 490                 495

Leu Gly Ser Gly Asn Val Gly Val Gly Asn Ile Gly Asn Asp Asn Ile
                500                 505                 510

Gly Asn Ala Asn Ile Gly Phe Gly Asn Arg Gly Asp Ala Asn Ile Gly
            515                 520                 525

Ile Gly Asn Ile Gly Asp Arg Asn Leu Gly Ile Gly Asn Thr Gly Asn
    530                 535                 540

Trp Asn Ile Gly Ile Gly Ile Thr Gly Asn Gly Gln Ile Gly Phe Gly
545                 550                 555                 560

Lys Pro Ala Asn Pro Asp Val Leu Val Val Gly Asn Gly Gly Pro Gly
                565                 570                 575

Val Thr Ala Leu Val Met Gly Gly Thr Asp Ser Leu Leu Pro Leu Pro
                580                 585                 590

Asn Ile Pro Leu Leu Glu Tyr Ala Ala Arg Phe Ile Thr Pro Val His
            595                 600                 605

Pro Gly Tyr Thr Ala Thr Phe Leu Glu Thr Pro Ser Gln Phe Pro
    610                 615                 620

Phe Thr Gly Leu Asn Ser Leu Thr Tyr Asp Val Ser Val Ala Gln Gly
625                 630                 635                 640

Val Thr Asn Leu His Thr Ala Ile Met Ala Gln Leu Ala Ala Gly Asn
                645                 650                 655

Glu Val Val Phe Gly Thr Ser Gln Ser Ala Thr Ile Ala Thr Phe
            660                 665                 670

Glu Met Arg Tyr Leu Gln Ser Leu Pro Ala His Leu Arg Pro Gly Leu
```

-continued

```
                675                 680                 685
Asp Glu Leu Ser Phe Thr Leu Thr Gly Asn Pro Asn Arg Pro Asp Gly
            690                 695                 700

Gly Ile Leu Thr Arg Phe Gly Phe Ser Ile Pro Gln Leu Gly Phe Thr
705                 710                 715                 720

Leu Ser Gly Ala Thr Pro Ala Asp Ala Tyr Pro Thr Val Asp Tyr Ala
                725                 730                 735

Phe Gln Tyr Asp Gly Val Asn Asp Phe Pro Lys Tyr Pro Leu Asn Val
            740                 745                 750

Phe Ala Thr Ala Asn Ala Ile Ala Gly Ile Leu Phe Leu His Ser Gly
                755                 760                 765

Leu Ile Ala Leu Pro Pro Asp Leu Ala Ser Gly Val Val Gln Pro Val
            770                 775                 780

Ser Ser Pro Asp Val Leu Thr Thr Tyr Ile Leu Leu Pro Ser Gln Asp
785                 790                 795                 800

Leu Pro Leu Leu Val Pro Leu Arg Ala Ile Pro Leu Leu Gly Asn Pro
                805                 810                 815

Leu Ala Asp Leu Ile Gln Pro Asp Leu Arg Val Leu Val Glu Leu Gly
            820                 825                 830

Tyr Asp Arg Thr Ala His Gln Asp Val Pro Ser Pro Phe Gly Leu Phe
                835                 840                 845

Pro Asp Val Asp Trp Ala Glu Val Ala Ala Asp Leu Gln Gln Gly Ala
            850                 855                 860

Val Gln Gly Val Asn Asp Ala Leu Ser Gly Leu Gly Leu Pro Pro Pro
865                 870                 875                 880

Trp Gln Pro Ala Leu Pro Arg Leu Phe Ser Thr
                885                 890
```

<210> SEQ ID NO 3
<211> LENGTH: 818
<212> TYPE: PRT
<213> ORGANISM: Mycobacterium tuberculosis

<400> SEQUENCE: 3

```
Met Gly Ser Ser His His His His His His Ser Gly Leu Val Pro
1               5                   10                  15

Arg Gly Ser His Met Gly Thr His Leu Ala Asn Gly Ser Met Ser Glu
                20                  25                  30

Val Met Met Ser Glu Ile Ala Gly Leu Pro Ile Pro Pro Ile Ile His
            35                  40                  45

Tyr Gly Ala Ile Ala Tyr Ala Pro Ser Gly Ala Ser Gly Lys Ala Trp
        50                  55                  60

His Gln Arg Thr Pro Ala Arg Ala Glu Gln Val Ala Leu Glu Lys Cys
65                  70                  75                  80

Gly Asp Lys Thr Cys Lys Val Val Ser Arg Phe Thr Arg Cys Gly Ala
                85                  90                  95

Val Ala Tyr Asn Gly Ser Lys Tyr Gln Gly Gly Thr Gly Leu Thr Arg
            100                 105                 110

Arg Ala Ala Glu Asp Asp Ala Val Asn Arg Leu Glu Gly Gly Arg Ile
        115                 120                 125

Val Asn Trp Ala Cys Asn Glu Leu Met Thr Ser Arg Phe Met Thr Asp
    130                 135                 140

Pro His Ala Met Arg Asp Met Ala Gly Arg Phe Glu Val His Ala Gln
145                 150                 155                 160
```

```
Thr Val Glu Asp Glu Ala Arg Arg Met Trp Ala Ser Ala Gln Asn Ile
            165                 170                 175

Ser Gly Ala Gly Trp Ser Gly Met Ala Glu Ala Thr Ser Leu Asp Thr
        180                 185                 190

Met Thr Gln Met Asn Gln Ala Phe Arg Asn Ile Val Asn Met Leu His
        195                 200                 205

Gly Val Arg Asp Gly Leu Val Arg Asp Ala Asn Asn Tyr Glu Gln Gln
    210                 215                 220

Glu Gln Ala Ser Gln Gln Ile Leu Ser Ser Val Asp Ile Asn Phe Ala
225                 230                 235                 240

Val Leu Pro Pro Glu Val Asn Ser Ala Arg Ile Phe Ala Gly Ala Gly
            245                 250                 255

Leu Gly Pro Met Leu Ala Ala Ala Ser Ala Trp Asp Gly Leu Ala Glu
        260                 265                 270

Glu Leu His Ala Ala Gly Ser Phe Ala Ser Val Thr Thr Gly Leu
        275                 280                 285

Ala Gly Asp Ala Trp His Gly Pro Ala Ser Leu Ala Met Thr Arg Ala
    290                 295                 300

Ala Ser Pro Tyr Val Gly Trp Leu Asn Thr Ala Ala Gly Gln Ala Ala
305                 310                 315                 320

Gln Ala Ala Gly Gln Ala Arg Leu Ala Ala Ser Ala Phe Glu Ala Thr
            325                 330                 335

Leu Ala Ala Thr Val Ser Pro Ala Met Val Ala Ala Asn Arg Thr Arg
        340                 345                 350

Leu Ala Ser Leu Val Ala Ala Asn Leu Leu Gly Gln Asn Ala Pro Ala
        355                 360                 365

Ile Ala Ala Ala Glu Ala Glu Tyr Glu Gln Ile Trp Ala Gln Asp Val
    370                 375                 380

Ala Ala Met Phe Gly Tyr His Ser Ala Ala Ser Ala Val Ala Thr Gln
385                 390                 395                 400

Leu Ala Pro Ile Gln Glu Gly Leu Gln Gln Leu Gln Asn Val Leu
            405                 410                 415

Ala Gln Leu Ala Ser Gly Asn Leu Gly Ser Gly Asn Val Gly Val Gly
        420                 425                 430

Asn Ile Gly Asn Asp Asn Ile Gly Asn Ala Asn Ile Gly Phe Gly Asn
    435                 440                 445

Arg Gly Asp Ala Asn Ile Gly Ile Gly Asn Ile Gly Asp Arg Asn Leu
450                 455                 460

Gly Ile Gly Asn Thr Gly Asn Trp Asn Ile Gly Ile Gly Ile Thr Gly
465                 470                 475                 480

Asn Gly Gln Ile Gly Phe Gly Lys Pro Ala Asn Pro Asp Val Leu Val
            485                 490                 495

Val Gly Asn Gly Gly Pro Gly Val Thr Ala Leu Val Met Gly Gly Thr
        500                 505                 510

Asp Ser Leu Leu Pro Leu Pro Asn Ile Pro Leu Leu Glu Tyr Ala Ala
        515                 520                 525

Arg Phe Ile Thr Pro Val His Pro Gly Tyr Thr Ala Thr Phe Leu Glu
    530                 535                 540

Thr Pro Ser Gln Phe Phe Pro Phe Thr Gly Leu Asn Ser Leu Thr Tyr
545                 550                 555                 560

Asp Val Ser Val Ala Gln Gly Val Thr Asn Leu His Thr Ala Ile Met
            565                 570                 575

Ala Gln Leu Ala Ala Gly Asn Glu Val Val Val Phe Gly Thr Ser Gln
```

```
                580                 585                 590
Ser Ala Thr Ile Ala Thr Phe Glu Met Arg Tyr Leu Gln Ser Leu Pro
                595                 600                 605

Ala His Leu Arg Pro Gly Leu Asp Glu Leu Ser Phe Thr Leu Thr Gly
                610                 615                 620

Asn Pro Asn Arg Pro Asp Gly Gly Ile Leu Thr Arg Phe Gly Phe Ser
625                 630                 635                 640

Ile Pro Gln Leu Gly Phe Thr Leu Ser Gly Ala Thr Pro Ala Asp Ala
                645                 650                 655

Tyr Pro Thr Val Asp Tyr Ala Phe Gln Tyr Asp Gly Val Asn Asp Phe
                660                 665                 670

Pro Lys Tyr Pro Leu Asn Val Phe Ala Thr Ala Asn Ala Ile Ala Gly
                675                 680                 685

Ile Leu Phe Leu His Ser Gly Leu Ile Ala Leu Pro Pro Asp Leu Ala
                690                 695                 700

Ser Gly Val Val Gln Pro Val Ser Ser Pro Asp Val Leu Thr Thr Tyr
705                 710                 715                 720

Ile Leu Leu Pro Ser Gln Asp Leu Pro Leu Leu Val Pro Leu Arg Ala
                725                 730                 735

Ile Pro Leu Leu Gly Asn Pro Leu Ala Asp Leu Ile Gln Pro Asp Leu
                740                 745                 750

Arg Val Leu Val Glu Leu Gly Tyr Asp Arg Thr Ala His Gln Asp Val
                755                 760                 765

Pro Ser Pro Phe Gly Leu Phe Pro Asp Val Asp Trp Ala Glu Val Ala
                770                 775                 780

Ala Asp Leu Gln Gln Gly Ala Val Gln Gly Val Asn Asp Ala Leu Ser
785                 790                 795                 800

Gly Leu Gly Leu Pro Pro Trp Gln Pro Ala Leu Pro Arg Leu Phe
                805                 810                 815

Ser Thr

<210> SEQ ID NO 4
<211> LENGTH: 795
<212> TYPE: PRT
<213> ORGANISM: Mycobacterium tuberculosis

<400> SEQUENCE: 4

His Leu Ala Asn Gly Ser Met Ser Glu Val Met Met Ser Glu Ile Ala
1               5                   10                  15

Gly Leu Pro Ile Pro Pro Ile Ile His Tyr Gly Ala Ile Ala Tyr Ala
                20                  25                  30

Pro Ser Gly Ala Ser Gly Lys Ala Trp His Gln Arg Thr Pro Ala Arg
            35                  40                  45

Ala Glu Gln Val Ala Leu Glu Lys Cys Gly Asp Lys Thr Cys Lys Val
        50                  55                  60

Val Ser Arg Phe Thr Arg Cys Gly Ala Val Ala Tyr Asn Gly Ser Lys
65                  70                  75                  80

Tyr Gln Gly Gly Thr Gly Leu Thr Arg Arg Ala Ala Glu Asp Asp Ala
                85                  90                  95

Val Asn Arg Leu Glu Gly Gly Arg Ile Val Asn Trp Ala Cys Asn Glu
                100                 105                 110

Leu Met Thr Ser Arg Phe Met Thr Asp Pro His Ala Met Arg Asp Met
            115                 120                 125

Ala Gly Arg Phe Glu Val His Ala Gln Thr Val Glu Asp Glu Ala Arg
```

-continued

```
                130             135             140
Arg Met Trp Ala Ser Ala Gln Asn Ile Ser Gly Ala Gly Trp Ser Gly
145                 150                 155                 160

Met Ala Glu Ala Thr Ser Leu Asp Thr Met Thr Gln Met Asn Gln Ala
                165                 170                 175

Phe Arg Asn Ile Val Asn Met Leu His Gly Val Arg Asp Gly Leu Val
                180                 185                 190

Arg Asp Ala Asn Asn Tyr Glu Gln Gln Glu Gln Ala Ser Gln Gln Ile
                195                 200                 205

Leu Ser Ser Val Asp Ile Asn Phe Ala Val Leu Pro Pro Glu Val Asn
210                 215                 220

Ser Ala Arg Ile Phe Ala Gly Ala Gly Leu Gly Pro Met Leu Ala Ala
225                 230                 235                 240

Ala Ser Ala Trp Asp Gly Leu Ala Glu Glu Leu His Ala Ala Ala Gly
                245                 250                 255

Ser Phe Ala Ser Val Thr Thr Gly Leu Ala Gly Asp Ala Trp His Gly
                260                 265                 270

Pro Ala Ser Leu Ala Met Thr Arg Ala Ala Ser Pro Tyr Val Gly Trp
                275                 280                 285

Leu Asn Thr Ala Ala Gly Gln Ala Gln Ala Ala Gly Gln Ala Arg
290                 295                 300

Leu Ala Ala Ser Ala Phe Glu Ala Thr Leu Ala Ala Thr Val Ser Pro
305                 310                 315                 320

Ala Met Val Ala Ala Asn Arg Thr Arg Leu Ala Ser Leu Val Ala Ala
                325                 330                 335

Asn Leu Leu Gly Gln Asn Ala Pro Ala Ile Ala Ala Ala Glu Ala Glu
                340                 345                 350

Tyr Glu Gln Ile Trp Ala Gln Asp Val Ala Ala Met Phe Gly Tyr His
                355                 360                 365

Ser Ala Ala Ser Ala Val Ala Thr Gln Leu Ala Pro Ile Gln Glu Gly
                370                 375                 380

Leu Gln Gln Gln Leu Gln Asn Val Leu Ala Gln Leu Ala Ser Gly Asn
385                 390                 395                 400

Leu Gly Ser Gly Asn Val Gly Val Gly Asn Ile Gly Asn Asp Asn Ile
                405                 410                 415

Gly Asn Ala Asn Ile Gly Phe Gly Asn Arg Gly Asp Ala Asn Ile Gly
                420                 425                 430

Ile Gly Asn Ile Gly Asp Arg Asn Leu Gly Ile Gly Asn Thr Gly Asn
                435                 440                 445

Trp Asn Ile Gly Ile Gly Ile Thr Gly Asn Gly Gln Ile Gly Phe Gly
                450                 455                 460

Lys Pro Ala Asn Pro Asp Val Leu Val Val Gly Asn Gly Gly Pro Gly
465                 470                 475                 480

Val Thr Ala Leu Val Met Gly Gly Thr Asp Ser Leu Leu Pro Leu Pro
                485                 490                 495

Asn Ile Pro Leu Leu Glu Tyr Ala Ala Arg Phe Ile Thr Pro Val His
                500                 505                 510

Pro Gly Tyr Thr Ala Thr Phe Leu Glu Thr Pro Ser Gln Phe Phe Pro
                515                 520                 525

Phe Thr Gly Leu Asn Ser Leu Thr Tyr Asp Val Ser Val Ala Gln Gly
                530                 535                 540

Val Thr Asn Leu His Thr Ala Ile Met Ala Gln Leu Ala Ala Gly Asn
545                 550                 555                 560
```

```
Glu Val Val Val Phe Gly Thr Ser Gln Ser Ala Thr Ile Ala Thr Phe
                565                 570                 575

Glu Met Arg Tyr Leu Gln Ser Leu Pro Ala His Leu Arg Pro Gly Leu
                580                 585                 590

Asp Glu Leu Ser Phe Thr Leu Thr Gly Asn Pro Asn Arg Pro Asp Gly
                595                 600                 605

Gly Ile Leu Thr Arg Phe Gly Phe Ser Ile Pro Gln Leu Gly Phe Thr
                610                 615                 620

Leu Ser Gly Ala Thr Pro Ala Asp Ala Tyr Pro Thr Val Asp Tyr Ala
625                 630                 635                 640

Phe Gln Tyr Asp Gly Val Asn Asp Phe Pro Lys Tyr Pro Leu Asn Val
                645                 650                 655

Phe Ala Thr Ala Asn Ala Ile Ala Gly Ile Leu Phe Leu His Ser Gly
                660                 665                 670

Leu Ile Ala Leu Pro Pro Asp Leu Ala Ser Gly Val Val Gln Pro Val
                675                 680                 685

Ser Ser Pro Asp Val Leu Thr Thr Tyr Ile Leu Leu Pro Ser Gln Asp
                690                 695                 700

Leu Pro Leu Leu Val Pro Leu Arg Ala Ile Pro Leu Leu Gly Asn Pro
705                 710                 715                 720

Leu Ala Asp Leu Ile Gln Pro Asp Leu Arg Val Leu Val Glu Leu Gly
                725                 730                 735

Tyr Asp Arg Thr Ala His Gln Asp Val Pro Ser Pro Phe Gly Leu Phe
                740                 745                 750

Pro Asp Val Asp Trp Ala Glu Val Ala Ala Asp Leu Gln Gln Gly Ala
                755                 760                 765

Val Gln Gly Val Asn Asp Ala Leu Ser Gly Leu Gly Leu Pro Pro Pro
                770                 775                 780

Trp Gln Pro Ala Leu Pro Arg Leu Phe Ser Thr
785                 790                 795

<210> SEQ ID NO 5
<211> LENGTH: 143
<212> TYPE: PRT
<213> ORGANISM: Mycobacterium tuberculosis

<400> SEQUENCE: 5

Met Ile Thr Asn Leu Arg Arg Arg Thr Ala Met Ala Ala Ala Gly Leu
1               5                   10                  15

Gly Ala Ala Leu Gly Leu Gly Ile Leu Leu Val Pro Thr Val Asp Ala
                20                  25                  30

His Leu Ala Asn Gly Ser Met Ser Glu Val Met Met Ser Glu Ile Ala
                35                  40                  45

Gly Leu Pro Ile Pro Pro Ile Ile His Tyr Gly Ala Ile Ala Tyr Ala
        50                  55                  60

Pro Ser Gly Ala Ser Gly Lys Ala Trp His Gln Arg Thr Pro Ala Arg
65                  70                  75                  80

Ala Glu Gln Val Ala Leu Glu Lys Cys Gly Asp Lys Thr Cys Lys Val
                85                  90                  95

Val Ser Arg Phe Thr Arg Cys Gly Ala Val Ala Tyr Asn Gly Ser Lys
                100                 105                 110

Tyr Gln Gly Gly Thr Gly Leu Thr Arg Arg Ala Ala Glu Asp Asp Ala
                115                 120                 125

Val Asn Arg Leu Glu Gly Gly Arg Ile Val Asn Trp Ala Cys Asn
```

130           135           140

<210> SEQ ID NO 6
<211> LENGTH: 98
<212> TYPE: PRT
<213> ORGANISM: Mycobacterium tuberculosis

<400> SEQUENCE: 6

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 7
<211> LENGTH: 580
<212> TYPE: PRT
<213> ORGANISM: Mycobacterium tuberculosis

<400> SEQUENCE: 7

Met Asn Phe Ala Val Leu Pro Pro Glu Val Asn Ser Ala Arg Ile Phe
1               5                   10                  15

Ala Gly Ala Gly Leu Gly Pro Met Leu Ala Ala Ala Ser Ala Trp Asp
            20                  25                  30

Gly Leu Ala Glu Glu Leu His Ala Ala Ala Gly Ser Phe Ala Ser Val
        35                  40                  45

Thr Thr Gly Leu Ala Gly Asp Ala Trp His Gly Pro Ala Ser Leu Ala
    50                  55                  60

Met Thr Arg Ala Ala Ser Pro Tyr Val Gly Trp Leu Asn Thr Ala Ala
65                  70                  75                  80

Gly Gln Ala Ala Gln Ala Gly Gln Ala Arg Leu Ala Ala Ser Ala
                85                  90                  95

Phe Glu Ala Thr Leu Ala Ala Thr Val Ser Pro Ala Met Val Ala Ala
                100                 105                 110

Asn Arg Thr Arg Leu Ala Ser Leu Val Ala Ala Asn Leu Leu Gly Gln
            115                 120                 125

Asn Ala Pro Ala Ile Ala Ala Glu Ala Glu Tyr Glu Gln Ile Trp
        130                 135                 140

Ala Gln Asp Val Ala Ala Met Phe Gly Tyr His Ser Ala Ala Ser Ala
145                 150                 155                 160

Val Ala Thr Gln Leu Ala Pro Ile Gln Glu Gly Leu Gln Gln Leu
                165                 170                 175

Gln Asn Val Leu Ala Gln Leu Ala Ser Gly Asn Leu Gly Ser Gly Asn
            180                 185                 190

Val Gly Val Gly Asn Ile Gly Asn Asp Asn Ile Gly Asn Ala Asn Ile
        195                 200                 205

Gly Phe Gly Asn Arg Gly Asp Ala Asn Ile Gly Ile Gly Asn Ile Gly
    210                 215                 220

```
Asp Arg Asn Leu Gly Ile Gly Asn Thr Gly Asn Trp Asn Ile Gly Ile
225                 230                 235                 240

Gly Ile Thr Gly Asn Gly Gln Ile Gly Phe Gly Lys Pro Ala Asn Pro
            245                 250                 255

Asp Val Leu Val Val Gly Asn Gly Gly Pro Gly Val Thr Ala Leu Val
            260                 265                 270

Met Gly Gly Thr Asp Ser Leu Leu Pro Leu Pro Asn Ile Pro Leu Leu
            275                 280                 285

Glu Tyr Ala Ala Arg Phe Ile Thr Pro Val His Pro Gly Tyr Thr Ala
            290                 295                 300

Thr Phe Leu Glu Thr Pro Ser Gln Phe Phe Pro Phe Thr Gly Leu Asn
305                 310                 315                 320

Ser Leu Thr Tyr Asp Val Ser Val Ala Gln Gly Val Thr Asn Leu His
            325                 330                 335

Thr Ala Ile Met Ala Gln Leu Ala Ala Gly Asn Glu Val Val Val Phe
            340                 345                 350

Gly Thr Ser Gln Ser Ala Thr Ile Ala Thr Phe Glu Met Arg Tyr Leu
            355                 360                 365

Gln Ser Leu Pro Ala His Leu Arg Pro Gly Leu Asp Glu Leu Ser Phe
            370                 375                 380

Thr Leu Thr Gly Asn Pro Asn Arg Pro Asp Gly Gly Ile Leu Thr Arg
385                 390                 395                 400

Phe Gly Phe Ser Ile Pro Gln Leu Gly Phe Thr Leu Ser Gly Ala Thr
            405                 410                 415

Pro Ala Asp Ala Tyr Pro Thr Val Asp Tyr Ala Phe Gln Tyr Asp Gly
            420                 425                 430

Val Asn Asp Phe Pro Lys Tyr Pro Leu Asn Val Phe Ala Thr Ala Asn
            435                 440                 445

Ala Ile Ala Gly Ile Leu Phe Leu His Ser Gly Leu Ile Ala Leu Pro
450                 455                 460

Pro Asp Leu Ala Ser Gly Val Val Gln Pro Val Ser Ser Pro Asp Val
465                 470                 475                 480

Leu Thr Thr Tyr Ile Leu Leu Pro Ser Gln Asp Leu Pro Leu Leu Val
            485                 490                 495

Pro Leu Arg Ala Ile Pro Leu Leu Gly Asn Pro Leu Ala Asp Leu Ile
            500                 505                 510

Gln Pro Asp Leu Arg Val Leu Val Glu Leu Gly Tyr Asp Arg Thr Ala
            515                 520                 525

His Gln Asp Val Pro Ser Pro Phe Gly Leu Phe Pro Asp Val Asp Trp
            530                 535                 540

Ala Glu Val Ala Ala Asp Leu Gln Gln Gly Ala Val Gln Gly Val Asn
545                 550                 555                 560

Asp Ala Leu Ser Gly Leu Gly Leu Pro Pro Pro Trp Gln Pro Ala Leu
            565                 570                 575

Pro Arg Leu Phe
            580

<210> SEQ ID NO 8
<211> LENGTH: 94
<212> TYPE: PRT
<213> ORGANISM: Mycobacterium tuberculosis

<400> SEQUENCE: 8

Met Thr Ile Asn Tyr Gln Phe Gly Asp Val Asp Ala His Gly Ala Met
```

```
1               5                  10                 15
Ile Arg Ala Gln Ala Gly Ser Leu Glu Ala Glu His Gln Ala Ile Ile
                20                 25                 30

Ser Asp Val Leu Thr Ala Ser Asp Phe Trp Gly Gly Ala Gly Ser Ala
            35                 40                 45

Ala Cys Gln Gly Phe Ile Thr Gln Leu Gly Arg Asn Phe Gln Val Ile
        50                 55                 60

Tyr Glu Gln Ala Asn Ala His Gly Gln Lys Val Gln Ala Ala Gly Asn
65              70                 75                 80

Asn Met Ala Gln Thr Asp Ser Ala Val Gly Ser Ser Trp Ala
                85                 90
```

COMPOSITION AND METHOD FOR SPRAY DRYING AN ADJUVANT VACCINE EMULSION

CROSS-REFERENCE TO RELATED APPLICATION(S)

This application is a 371 of International Application PCT/US2020/034595, filed on May 26, 2020, which claims the benefit and priority of U.S. provisional application Ser. No. 62/852,983, filed on May 25, 2019, which is hereby incorporated by reference herein in its entirety, including all references and appendices cited therein, for all purposes, as if fully set forth herein.

FIELD

This specification generally relates to a dry powder composition and method for spray drying an adjuvant and/or adjuvant/antigen emulsion.

BACKGROUND OF THE INVENTION

Stockpiling vaccines in preparation for a pandemic as well as the provision of vaccines to remote or less developed areas is limited by lack of vaccine formulation stability without refrigeration. This can make providing vaccines to developing countries difficult due to the lack of refrigeration availability, particularly during transportation to remote areas. Eliminating the requirement of cold-chain for vaccines would greatly reduce the cost of storage and transportation and would further simplify stockpiling for pandemics. Additionally, existing vaccines commonly require admixture of the antigen with the adjuvant prior to administration of the vaccine to a subject. The provision of one vial vaccines that do not require admixture before administration would greatly reduce the risk of loss and simplify the process of vaccination.

The subject matter discussed in the background section should not be assumed to be prior art merely as a result of its mention in the background section. Similarly, a problem and the understanding of the causes of a problem mentioned in the background section or associated with the subject matter of the background section should not be assumed to have been previously recognized in the prior art. The subject matter in the background section may merely represent different approaches, which in and of themselves may also be inventions. All publications, patents, and patent applications cited herein are hereby incorporated by reference in their entirety for all purposes.

BRIEF SUMMARY OF THE INVENTION

One aspect of the invention is a dry powder vaccine composition, comprising an effective amount of an antigen, an adjuvant, a metabolizable oil, and one or more excipients, wherein the particle size of the dry powder has a diameter of less than about 120 µm. Other aspects of the invention are dry powder vaccine compositions, comprising an effective amount of an adjuvant, a metabolizable oil, and one or more excipients, wherein the particle size of the dry powder has a diameter of less than about 120 µm. In some embodiments, the particles of the dry powder vaccine have a diameter of less than about 20 m. In some embodiments, the one or more excipients is a saccharide selected from the group consisting of trehalose, lactose, raffinose, and lactulose. In some embodiments, the metabolizable oil is chosen from squalene, synthetic squalene, grape seed oil, polyprenol, olive oil or a synthetic isoprenoid. In some embodiments, the adjuvant is a TLR4 agonist. In some embodiments, the composition is thermostable at a temperature between about 8° C. to about 60° C. for at least 1 month. In some embodiments, the composition is thermostable for at least 3 months, including at least 6 months, including at least 12 months.

In some aspects, the composition further comprises 1,2-dimyristoyl-sn-glycero-3-phosphocholine (DMPC), 1-palmitoyl-2-oleoyl-sn-glycerol-3-phosphocholine (POPC), 1,2-dioleoyl-sn-glycero-3-phosphocholine (DOPC), Dipalmitoylphosphatidylcholine (DSPC), egg PC, lecithin, tween, or a combination thereof. In some embodiments, the metabolizable oil is squalene. In some embodiments, the TLR4 agonist is MPL, 3d-MPL, or synthetic GLA. In some embodiments, the TLR4 agonist is GLA. In some embodiments, the particle size is less than about 120 µm and the composition is inhalable. In some embodiments, the antigen is a polypeptide, a nucleic acid encoding a polypeptide, or a pathogen. In some embodiments, the dry powder is produced by spray drying.

Other aspects of the invention include an inhalable, dry powder vaccine composition, comprising an effective amount of an adjuvant, a metabolizable oil, and one or more excipients, wherein the particle size of the dry powder has a diameter of less than about 120 µm. In some embodiments, the inhalable, dry powder vaccine composition, comprises an effective amount of an antigen, an adjuvant, a metabolizable oil, and one or more excipients, wherein the particle size of the dry powder has a diameter of less than about m. In some embodiments, the particles of the inhalable dry powder vaccine have a diameter of less than about 10 µm or as low as 100 nm-300 nm. In some embodiments, the composition is thermostable at a temperature between about 8° C. to about 60° C. for at least 1 month. In some embodiments, the composition includes a shell former taken from the group of peptides or amino acids. In some embodiments, the shell former is leucine. In some embodiments, the composition includes 1,2-dimyristoyl-sn-glycero-3-phosphocholine (DMPC), 1-palmitoyl-2-oleoyl-sn-glycerol-3-phosphocholine (POPC), 1,2-dioleoyl-sn-glycero-3-phosphocholine (DOPC), Dipalmitoylphosphatidylcholine (DSPC), egg PC, lecithin, tween, or a combination thereof.

Other aspects of the invention are methods for generating a thermostable dry powder vaccine composition, comprising the step of spray drying an oil-in-water emulsion to form a thermostable dry powder vaccine composition, wherein the oil-in-water emulsion comprises (1) an antigen, (2) a metabolizable oil, (3) one or more excipients, (4) an adjuvant, and (5) a shell-former. In some embodiments, the method includes packaging the spray-dried vaccine in an aluminum bag with a desiccant pouch and double heat-sealing. In some embodiments, the oil-in-water emulsion further comprises a shell former. In some embodiments, the oil-in-water emulsion further comprises 1,2-dimyristoyl-sn-glycero-3-phosphocholine (DMPC), 1-palmitoyl-2-oleoyl-sn-glycerol-3-phosphocholine (POPC), 1,2-dioleoyl-sn-glycero-3-phosphocholine (DOPC), egg PC, lecithin, tween, or a combination thereof. In some embodiments, the method also includes spray drying the composition in a spray dryer using an atomization gas at predetermined process parameters to obtain a spray dried powder vaccine. In some embodiments, the parameters include an atomizing gas pressure of 10 psi, an atomizing gas flow rate of 0.6 mL/min, and a drying gas flow rate of 200 SLPM.

Other aspects of the invention are methods of administering a thermostable dry powder therapeutic composition to a subject, comprising administering a thermostable dry powder vaccine via inhalation of the dry powder.

Other aspects of the invention are methods of administering a thermostable dry powder vaccine composition to a subject, comprising (1) reconstituting a dry powder vaccine with an aqueous diluent and (2) administering the reconstituted dry powder vaccine via a parenteral route. In some embodiments, the thermostable dry powder vaccine is any of the composition provided herein.

Other aspects of the invention are methods of administering a dry powder therapeutic composition to a subject, comprising administering a thermostable dry powder therapeutic via inhalation of the dry powder. The therapeutic immune response elicited by the method can be for treatment of cancer. The methods also include administering the dry powder therapeutic parenterally after reconstitution. In some embodiments, the dry powder vaccine may demonstrate therapeutic benefits in diseases with a respiratory component, including, but not limited to, Tuberculosis (TB), Influenza (flu), Respiratory syncytial virus infection (RSV), and lung cancer. In some embodiments, if the delivery is via inhalation, the particle size is less than about 20 µm. In some embodiments, if the delivery is via a respiratory route (such as nasal or pulmonary), the particle size is less than about 120 µm.

Any of the above embodiments may be used alone or together with one another in any combination. Inventions encompassed within this specification may also include embodiments that are only partially mentioned or alluded to or are not mentioned or alluded to at all in this brief summary or in the abstract.

BRIEF DESCRIPTION OF THE DRAWINGS

In the following drawings like reference numbers are used to refer to like elements. Although the following figures depict various examples of the invention, the invention is not limited to the examples depicted in the figures.

FIG. 8 shows a diagram of a next generation impactor (NGI). The version shown is combined with an Alberta Idealized Throat and can be used to model deposition in the human throat and lungs.

DETAILED DESCRIPTION

Figure 1:
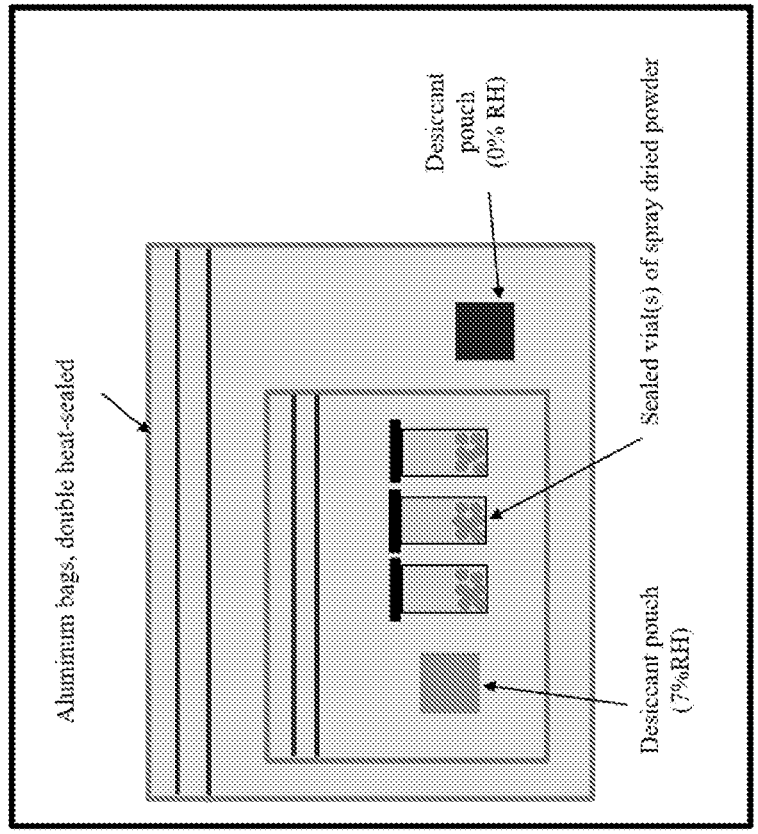
FIG. 1a shows a simplified schematic showing the functional principle for a nano spray dryer.
FIG. 1b shows a simplified schematic for a packaging protocol to ensure humidity control during powder storage.
Figure 1:
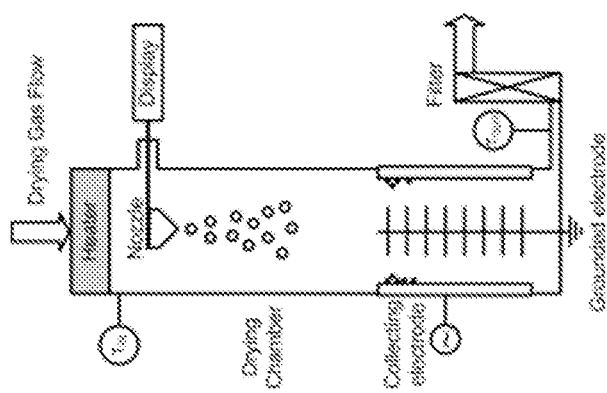

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

In one aspect, spray drying is used to produce a dry powder vaccine containing an antigen or adjuvant or both. Thus, the invention provides dry powder vaccine compositions, comprising an effective amount of an antigen, an adjuvant, a metabolizable oil, and one or more excipients, wherein the particle size of the dry powder has a diameter of less than about 120 µm for respiratory delivery (e.g., nasal or pulmonary) or less than about 20 µm for respiratory delivery (e.g., via inhalation). In other embodiments, the dry powder vaccine does not have an antigen. In some embodiments, the dry powder vaccine does not have an adjuvant. In some embodiments, the dry powder vaccine has more than one antigen or adjuvant or both. The dry powder vaccine can be formulated and spray dried to create particle sizes conducive to administration via inhalation. Thus, in some aspects the dry powder vaccine has a particle size of less than about 20 µm including but not limited to 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2 µm, 1 µm, less than 900 nm, less than 800 nm, less than 700 nm, less than 600 nm, less than 500 nm, less than 400 nm, less than 300 nm, less than 200 nm, and less than 100 nm. In some embodiments, the dry powder vaccine has a particle size of less than about 120 µm, including but not limited to 110 µm, 100 µm, 90 µm, 80 µm, 70 µm, 60 µm, 50 µm, 40 µm, 30 µm, and 20 µm. In some embodiments, the formulation for the inhalable dry powder vaccine also comprises a shell former (e.g., leucine). Other aspects of the invention are methods of making dry powder vaccine compositions that are thermostable, and/or inhalable.

As one of skilled in the art will appreciate, the terms, spray dried vaccine, spray dried adjuvant mixture, spray dried vaccine composition, thermostable spray dried vaccine, dry powder vaccine, dry powder adjuvant, and dry powder vaccine composition are used interchangeably herein. This term generally refers to a spray dried powder comprising an effective amount of an antigen, an adjuvant, a metabolizable oil, and one or more excipients, wherein the particle size of the dry powder has a diameter of less than about 50 µm. In some embodiments, the particle size of the dry powder has a diameter of less than about 20 µm. In some embodiments, the particle size of the dry powder has a diameter of less than 15 µm, including but not limited to, less than 10 µm, less than 5 µm, less than 4 µm, less than 3 µm, less than 2 µm, less than 1 µm, less than 900 nm, less than 800 nm, less than 700 nm, less than 600 nm, less than 500 nm, less than 400 nm, less than 300 nm, less than 200 nm, and less than 100 nm. The vaccine can be administered as a dry powder (via inhalation) or after reconstitution (e.g., via a parenteral route).

As provided herein, the spray dried vaccine is thermostable. For example, the composition is stable from between about 8° C. and about 60° C., including, but not limited to, 10° C., 15° C., 20° C., 25° C., 30° C., 35° C., 40° C., 45° C., 50° C., and 55° C. Such compositions further comprise suitable excipients, such as pharmaceutically acceptable excipients (carriers) including buffers, acids, bases, sugars, diluents, preservatives, shell formers, cryo preservatives, and the like which are well known in the art and are described herein.

Conversion of liquid material, such as vaccines, into a dry powder will reduce costs associated with refrigeration and transportation. Spray drying provides a unique solution as it allows for the powder to be engineered to have specific properties. As such, in the examples herein, spray drying was investigated as a method to encapsulate an adjuvanted tuberculosis vaccine, formulated as oil-in-water nanoemulsions, within dry powder. Successful encapsulation of the adjuvanted vaccine within non-cohesive, amorphous microparticles was achieved in one iteration, with high retention rate of all components. Stability of the powder was investigated over 3 months at different temperatures. Results showed that the powder was physically stable for all temperatures. Physiochemical analysis on the reconstituted powder showed small antigen and adjuvant losses over time with increased temperature storage, though nano-emulsion size was maintained for all samples. These proof of concept results indicate a novel method of adjuvanted vaccine encapsulation, with room for stability improvement via further formulation development. The use of spray drying also allows for inhalable routes of delivery.

In some aspects, the invention provides methods for stimulating an immune response in a subject comprising reconstituting a spray dried vaccine composition described herein into an emulsion and administering the emulsion to the subject. In some embodiments, the emulsion is an oil-in-water emulsion. In some embodiments, the immune response is a non-specific immune response. In some embodiments, the immune response is an antigen-specific immune response. A method described herein for stimulating an immune response, or a reconstituted thermostable spray-dried vaccine composition described herein, can be used alone or in combination with other conventional methods of treatment (e.g., chemotherapeutic agents). In another embodiment, the invention provides methods for stimulating an immune response in a subject comprising administering the dry powder to the subject without reconstitution (via inhalation).

In some aspects, the invention provides methods for administering a therapeutic for the treatment of cancer, autoimmune diseases, etc. The methods may comprise administering a therapeutic amount of the dry powder composition via inhalation or other methods to the lungs or respiratory system. The methods may comprise reconstituting the dry powder composition and then administering the reconstituted composition parenterally.

In some aspects, the spray dried vaccine compositions were tested and the nano-emulsion size was maintained for all samples. This was a surprising result, because it was not known in the field that nanoemulsions of a substance that is liquid at room temperature could be converted into a gel-microparticle and reconstituted to the same droplet size without significant losses. Previous attempts either resulted in significant losses or changes in the droplet sizes.

In some embodiments, reference to "about" a value or parameter herein includes (and describes) variations that are directed to that value or parameter per se. For example, description referring to "about X" includes description of "X".

Definitions

It is understood that aspects and embodiments of the invention described herein include "comprising," "consisting," and "consisting essentially of" aspects and embodiments.

An "individual" or a "subject" is a mammal, more preferably a human. Mammals also include, but are not limited to farm animals, sport animals, pets (such as cats, dogs, horses), primates, mice and rats.

As used herein and in the appended claims, the singular forms "a," "an," and "the" include plural reference unless the context clearly indicates otherwise.

As used herein, "spray-dried emulsions," is used interchangeably with "dry powder vaccine," "dry powder," "dry powder adjuvant," "dry powder compositions," spray dried compositions, "spray dried vaccines," "powder" and "dry emulsions".

As used herein "reconstituted" dry powder vaccine or vaccine refers to adding a liquid to the dry powder. This may be for administering the vaccine or may be for testing the vaccine.

As used herein "Spray drying" is the process of producing a powder through the drying of aerosolized solution droplets.

Excipients as used herein refers to substances other than the pharmacologically active drugs, which are included in the manufacturing process, or fill-finish process for storage or shipment of the pharmacologically active drug. "Spray-dried excipients" or "excipients", as used herein, may refer to substances other than the pharmacologically active drug which are included in the spray dry process to contribute to the form or formulation of a suitable powder structure. Excipients may include bulking agents, buffering agents, emulsifiers or solubilizing agents.

GLA-SE is the Toll-like receptor 4 agonist glucopyranosyl lipid adjuvant-stable emulsion (GLA-SE), a vaccine adjuvant consisting of the synthetic TLR4 agonist glucopyranosyl lipid adjuvant (GLA) formulated in a squalene-in-water emulsion (SE). GLA-SE augments both TH1 and IgG2-skewed antibody responses to a variety of vaccine antigens.

ID93 is a subunit TB vaccine candidate comprised of four antigens representing different families of Mtb proteins. Rv1813 is a conserved hypothetical protein that is upregulated under hypoxic growth and predicted to be localized in the outer membrane. Rv2608 (PPE42) is a probable outer membrane-associated PPE (Pro-Pro-Glu (PPE) motif-containing) protein. Rv3619 (EsxV) and Rv3620 (EsxW) are secreted proteins belonging to the ESAT-6 family of virulence factors. The four ID93 antigens have been shown to be recognized in Mtb-exposed individuals.

Spray drying is a gentle method for producing powders with a defined particle size out of solutions, dispersions, and emulsions which is used for pharmaceuticals, food, biotechnology, and other industrial materials synthesis. FIG. 1a shows a diagram of a typical spray drying technique, showing that spray drying uses drying gas to rapidly evaporate solvent (or water) from atomized particles, leaving behind only the solid components of the solution (the dry powder). The drying medium is typically air, but an inert gas, e.g. nitrogen, can be employed when the liquid is a flammable solvent or the product is oxygen-sensitive.

In the past, the limitations of spray drying were the particle size (minimum 2 micrometers), the yield (maximum around 70%), and the sample volume (minimum 50 ml for devices in lab scale). Recently, minimum particle sizes have been reduced to 300 nm, yields up to 90% are possible, and the sample amount can be as small as 1 ml. These expanded limits are possible due to new technological developments to the spray head, the heating system, and the electrostatic particle collector. To emphasize the small particle sizes possible with this new technology, it has been described as "nano" spray drying. However, the smallest particles produced are in the sub-micrometer range common to fine particles rather than the nanometer scale of ultrafine particles.

General Techniques

The practice of the present invention will employ, unless otherwise indicated, conventional techniques of molecular biology, recombinant DNA, biochemistry, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Md. (1989).

Characteristics of the Spray Dried Adjuvant or Antigen Compositions

Provided herein are spray dried compositions comprising an antigen and/or an adjuvant. In some embodiments, the spray dried compositions are dry powder vaccine compositions. The dry powder vaccine compositions can be antigen compositions, adjuvant compositions and/or antigen/adjuvant (one vial) compositions. The present invention describes that antigen, adjuvant vaccine compositions can be spray dried and stored, maintained, or exposed to temperatures between about 8° C. to about 60° C. and that the compositions can be administered in a reconstituted form or as a dry powder via inhalation. Further, when reconstituted, the compositions may have one or more of the following characteristics: (1) maintain a desirable pH around physiologic 7.4, (2) maintain a particle size of less than 120 μm with little or no aggregation, (3) exhibit no significant degradation or alteration of each active ingredient (for example the antigen, the adjuvant), and (4) are suitable to induce or stimulate an immune response in a subject.

Thermostability of the spray dried (dry powder) vaccine compositions provided herein can be assessed in the spray dried (powder) state or following reconstitution. Thermostability of the spray dried vaccine compositions provided herein can be assessed by visual observation, and/or with the aid of one or more assays provided herein. These assays can provide an estimate of the integrity of the emulsion, antigen, and/or adjuvant following spray drying and reconstitution.

The thermostability assays and observations described herein can be carried out upon spray drying, 1 hour following spray drying, 6 hours following spray drying, 12 hours following spray drying, 24 hours following spray drying, 36 hours following spray drying, 48 hours following spray drying, 1 week following spray drying, 2 weeks following spray drying, 1 month following spray drying, 2 months following spray drying, 3 months following spray drying, 4 months following spray drying, 6 months following spray drying, 12 months following spray drying, or beyond. Prior to carrying out the assays and observations, the composition can be maintained, stored at, or exposed to temperatures greater than or about 8° C., for example, greater than or about 25° C., greater than or about 37° C., or greater than or about 50° C., or about 60° C.

The thermostability assays and observations described herein can be carried out upon reconstitution of the dry powder composition, immediately upon reconstitution, 1 hour following reconstitution, 6 hours following reconstitution, 12 hours following reconstitution, 24 hours following reconstitution, 36 hours following reconstitution, 48 hours following reconstitution, or 1 week following reconstitution.

One of ordinary skill in the art would understand that the present invention is designed to provide dry powder vaccine compositions that can be stored and or shipped at temperatures more closely approaching ambient temperatures in the developed or developing world therefore in some embodiments the spray dried composition is maintained, stored, or exposed to more than one temperature or a combination of temperatures between about 8° C. and about 60° C.

In some embodiments, the thermostability of the dry powder vaccine compositions provided herein is assessed by visual observation, prior to reconstitution as a dry powder. In other embodiments, the thermostability of the dry powder vaccine compositions provided herein is assessed following reconstitution by the aid of one or more assays, for example biophysical and biochemical assays.

In some embodiments, the particle size of the dry powder or the reconstituted vaccine is evaluated. For example, dynamic light scattering (DLS) can be used to evaluate emulsion particle size. In some embodiments, this is compared to the emulsion particle size prior to dry spraying, for example in the liquid stable emulsion state prior to dry spraying. In some embodiments the emulsion particle size is not compared to the particles size prior to dry spraying. In some embodiments herein, the particle size is determined by measuring the Z-average diameter (Z-Ave) of the liquid dry powder composition. In particular embodiments, a thermostable composition is indicated when the reconstituted liquid emulsion of the spray dried composition maintained, stored, or exposed at a temperature greater than or about 8° C. has a particle size with a Z-average diameter of less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, or less than about 90 nm, less than about 80 nm, less than about 70 nm, or less than about 60 nm. In particular embodiments, the reconstituted emulsion has a particle size with a Z-average diameter range of about 100 nm to about 200 nm In some embodiments, the polydispersity index (PdI) is evaluated following reconstitution of the spray dried composition. For example, dynamic light scattering (DLS) can be used to evaluate the PdI. In some embodiments, this is compared to the PDI of the liquid emulsion prior to spray drying, for example in the liquid stable emulsion state prior to spray drying.

In some embodiments, the pH of the emulsion is evaluated following reconstitution of the spray dried (dry powder) composition. In some embodiments, this is compared to the pH prior to spray drying, for example in the liquid stable emulsion state prior to spray drying.

In some embodiments, the % deterioration or % breakdown of the antigen, adjuvant, and/or other components of the dry powder composition is evaluated, upon reconstitution or as a dry powder. In some embodiments, reverse phase high performance liquid chromatography (RP-HPLC) is used to evaluate the chemical degradation, if any, of the components. In one exemplary embodiment, the chemical degradation of squalene, DMPC, and GLA, is monitored by RP-HPLC. In other embodiments gel-based Coomassie staining is used to evaluate the degradation of the protein antigen of vaccine, if any, of the spray dried composition, upon reconstitution. A thermostable composition as provided herein is one exhibits no more than or about 25%, 20%, 15%, 10%, 9%, 8%, 7%, 6%, 5%, 4%, 3%, 2%, 1% antigen and/or adjuvant, or other component degradation, loss or breakdown after reconstitution of the thermostable spray dried composition which was maintained at a temperature greater than or at about 8° C.

Excipients

Excipients of the invention may be used singly or in combination with other excipients which include, but are not limited to, shell-forming agents, buffering agents, solubilizing agents, isotonicity agents, tonicifying agents, surfactants, emulsifiers, antimicrobial agents, and/or collapse temperature modifiers.

In some embodiments the excipients are substances other than the pharmacologically active drug, which are included in the manufacturing process, or fill-finish process for storage or shipment of the pharmacologically active drug including, without limitation, spray drying, and are contained in a finished pharmaceutical process.

In some embodiments, an excipient is a substance added to a liquid stable oil-in-water emulsion formulation prior to spray drying which yields a powder following spray drying. In some embodiments, excipients are substances that enhance the inhalability of spray dried formulations, such as by reducing the particle size of the spray dried powder or making the particle less likely to stick to each other or to the tissues in the mouth, throat or esophagus.

Excipients suitable for vaccine formulations and/or spray dried vaccine or adjuvant formulations are known in the art (See, e.g. Bahetia et. al., 2010: J. Excipients and Food Chem.:1 (1)41-54, Grabenstein J D. ImmunoFacts: Vaccines and Immunologic Drugs—2012 (37th revision). St Louis, Mo.: Wolters Kluwer Health, 2011 and, by Vaccine) and include, buffering agents, solubilizing agents, isotonicity agents, tonicifying agents, surfactants, emulsifiers, antimicrobial agents, and/or collapse temperature modifiers. A list of excipients in currently approved vaccines can be found via the Centers for Disease Control (see worldwide web at cdc.gov/vaccines/pubs/pinkbook/downloads/appendices/B/excipient-table-2.p-df., September 2013, "Vaccine Excipient & Media Summary. Excipients Included in U.S. Vaccines, by Vaccine") and include without limitation sucrose, D-mannose, D-fructose, dextrose, potassium phosphate, plasdone C, anhydrous lactose, micro crystalline cellulose, polacrilin potassium, magnesium stearate, cellulose acetate phthalate, alcohol, acetone, castor oil, FD&C Yellow #6 aluminum lake dye, human serum albumin, fetal bovine serum, sodium bicarbonate, human-diploid fibroblast cell cultures (WI-38), Dulbecco's Modified Eagle's Medium, aluminum hydroxide, benzethonium chloride, formaldehyde, gluteraldehyde, amino acids, vitamins, inorganic salts, sugars, glycerin, asparagine, citric acid, potassium phosphate, magnesium sulfate, iron ammonium citrate, lactose, aluminum potassium sulfate, aluminum hydroxyphosphate, potassium aluminum sulfate, peptone, bovine extract, thimerosal (trace), modified Mueller and Miller medium, beta-propiolactone, thimerosol (multi-dose vials only), monobasic sodium phosphate, dibasic sodium phosphate, monobasic potassium phosphate, potassium chloride, potassium glutamate, calcium chloride, sodium taurodeoxycholate, neomycin sulfate, polymyxin B, egg protein, lactalbumin hydrolysate, and neomycin sulfate.

Buffering Agents

In some embodiments, the compositions of the present invention comprise a buffering agent. Buffering agents useful as excipients in the present invention include Tris acetate, Tris base, Tris HCl, Ammonium phosphate, Citric Acid, Sodium Citrate, Potassium citrate, Tartic Acid, Sodium Phosphate, Zinc Chloride, Arginine, and Histidine. In some embodiments buffering agents include pH adjusting agents such as hydrochloric acid, sodium hydroxide, and meglumine.

Solubilizing Agents

In some embodiments suitable solubilizing agents include complexing excipients such as ethylenediaminetetraacetic acid (EDTA), Alpha cyclodextrin, Hydroxypropyl-.beta.-cyclodextrin (HP-.beta.-CD). Surfactants may also be included as solubilizing excipients including polysorbate 80 and Tween. Other Co-Solvents known in the art as solubilizing agents may be used and include tert-butyl alcohol, isopropyl alcohol, dichloromethane, ethanol and acetone.

Tonicifying agents for use as excipients in the present invention include glycerol, sodium chloride, sucrose, mannitol, and dextrose. Collapse temperature modifiers include dextran, Hydroxyethyl starch, ficoll, and gelatin. Antimicrobial agents include benzyl alcohol, phenol, m-cresol, methyl paraben, ethyl paraben, thimerosol.

Isotonicity Agents

In some embodiments, the compositions of the present invention comprise an isotonicity agent. In some embodiments, the isotonicity agent is glycerol. In one particular embodiment, the isotonicity agent is present at a concentration of about 0.36% v/v in the oil-in-water emulsion formulation prior to spray drying or in the oil-in-water emulsion upon reconstitution.

Surfactants

In some embodiments, the compositions of the present invention comprise a surfactant. In some embodiments, the surfactant is pluronic F68. In some embodiments, the surfactant is present at a ratio of about 100:1 (oil:surfactant). In some embodiments, the surfactant is present at a concentration of about 0.018% w/v. In some embodiments, the surfactant is present at a concentration of about 0.0001% w/v, about 0.0005% w/v, about 0.001% w/v, about 0.005% w/v, about 0.01% w/v, about 0.011% w/v, about 0.012% w/v, about 0.013% w/v, about 0.014% w/v, about 0.015% w/v, about 0.016% w/v, about 0.017% w/v, about 0.018% w/v, about 0.019% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, or about 1% w/v. The percentages and ratios described herein refer to the ratios and percentages in either the oil-in-water emulsion formulation prior to spray drying or in the dry powder or in the dry powder after reconstitution.

Emulsifiers

In some embodiments, the compositions of the present invention comprise an emulsifier. In some embodiments, the emulsifier is 1,2-dimyristoyl-sn-glycero-3-phosphocholine (DMPC). In some embodiments, the emulsifier is lecithin. In some embodiments, the emulsifier is present at a ratio of about 1:5 (emulsifier:oil). In some embodiments, the emulsifier is present at a concentration of about 0.38% w/v. In some embodiments, the emulsifier is present at a concentration of about 0.002% w/v, about 0.005% w/v, about 0.010% w/v, about 0.015% w/v, about 0.020% w/v, about 0.025% w/v, about 0.030% w/v, about 0.035% w/v, about 0.040% w/v, about 0.045% w/v, about 0.050% w/v, about 0.055% w/v, about 0.060% w/v, about 0.065% w/v, about 0.070% w/v, about 0.075% w/v, about 0.080% w/v, about 0.085% w/v, about 0.090% w/v, about 0.095% w/v, about 0.10% w/v, about 0.15% w/v, about 0.20% w/v, about 0.25% w/v, about 0.30% w/v, about 0.35% w/v, about 0.40% w/v, about 0.45% w/v, about 0.50% w/v, about 0.55% w/v, about 0.60% w/v, about 0.65% w/v, about 0.70% w/v, about 0.75% w/v, about 0.80% w/v, about 0.85% w/v, about 0.90% w/v, about 0.95% w/v, about 1% w/v, about 2% w/v, about 3% w/v, about 4% w/v, about 5% w/v, about 6% w/v, about 7% w/v, about 7.5% w/v, about 8% w/v, about 9% w/v, or about 10% w/v. The percentages and ratios described herein refer to the ratios and percentages in either the oil-in-water emulsion formulation prior to spray drying or in the dry powder.

Adjuvants for Use in Thermostable Spray Dried Vaccine Compositions

In some aspects of the invention provided herein, a composition described herein (e.g., thermostable spray dried vaccine) comprises an adjuvant. In some embodiments the adjuvant is provided alone, for example, for use a therapeutic agent. In other embodiments, the adjuvant is provided in combination with an antigen.

Adjuvants for use in compositions that modify the immune response are well known in the art. For example, adjuvants for use in compositions described herein may comprise one or more of an immunostimulatory adjuvant, a delivery adjuvant, an inorganic adjuvant, or an organic adjuvant. Non-limiting examples of adjuvants for use in compositions described herein can be found, inter alia, in Barouch D. H., 2008, Nature, 455(7213):613-9; Morrow et al., 2008, AIDS, 22(3):333-8; and McGeary et al., 2003, Peptide Sci., 9(7):405-181.

In some embodiments, an adjuvant used in a composition described herein (e.g., thermostable dry powder vaccine) is an immunostimulatory adjuvant. Immunostimulatory adjuvants can be adjuvants that directly act on the immune system such as, for example, a cytokine, a TLR ligand or a microbial toxin. In some embodiments herein, the adjuvant is a cytokine adjuvant. One or more cytokine can be suitable as an adjuvant alone or in a combination with one or more additional adjuvants in a composition described herein. Suitable cytokines include an interferon (IFN), an interleukin (IL), a chemokine, a colony-stimulating factor, or a tumor necrosis factor. In some embodiments, the interferon is a Type I IFN, a Type II IFN, or a Type III IFN. In some embodiments, the interferon is Inala., Inbeat's., IFN-gamma., or IFN-lamda. and subtypes from among these (e.g., IFN-lamda., IFN-lamda.2, and IFN-lamda.3). In some embodiments, the cytokine is an interleukin. Non-limiting examples of interleukins that can be used as an adjuvant in a composition described herein include IL-1, IL-2, IL-3, IL-4, IL-5, IL-6, IL-7, IL-8, IL-9, IL-10, IL-11, IL-12, IL-13, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35 and IL-36. In some embodiments, the cytokine is a chemokine. In some embodiments, the chemokine is a CC chemokine, a CXC chemokine, a C chemokine, or a CX3C chemokine. Non-limiting examples of CC chemokines that can be used as an adjuvant in a composition described herein include CCL1, CCL2, CCL3, CCL4, CCL5, CCL6, CCL7, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. Non-limiting examples of CXC chemokines that can be used in a composition described herein include CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. In some embodiments, the cytokine is a colony-stimulating factor. In some embodiments, the colony-stimulatory factor is granulocyte macrophage colony-stimulating factor (GM-CSF), granulocyte colony-stimulating factor (G-CSF), or macrophage colony-stimulating factor (M-CSF). In some embodiments, the cytokine is a tumor necrosis factor. Non-limiting examples of a tumor necrosis factor family protein that can be used as an adjuvant in a composition described herein include TNF-alpha. and 4-1BBL.

In some embodiments, the immunostimulatory adjuvant is a Toll-like receptor (TLR) ligand (e.g., a TLR agonist). One or more TLR ligand can be suitable as an adjuvant alone or in a combination with one or more additional adjuvant in a composition described herein. TLRs include cell surface transmembrane receptors of the innate immune system that confer early-phase recognition capability to host cells for a variety of conserved microbial molecular structures such as may be present in or on a large number of infectious pathogens. (e.g., Armant et al., 2002 Genome Biol. 3(8): reviews3011.1-3011.6; Fearon et al., 1996 Science 272:50; Medzhitov et al., 1997 Curr. Opin. Immunol. 9:4; Luster 2002 Curr. Opin. Immunol. 14:129; Lien et al. 2003 Nat. Immunol. 4:1162; Medzhitov, 2001 Nat. Rev. Immunol. 1:135; Takeda et al., 2003 Ann Rev Immunol. 21:335;

Takeda et al. 2005 Int. Immunol. 17:1; Kaisho et al., 2004 Microbes Infect. 6:1388; Datta et al., 2003 J. Immunol. 170:4102).

Induction of TLR-mediated signal transduction to potentiate the initiation of immune responses via the innate immune system may be effected by TLR agonists (i.e., a TLR ligand), which engage cell surface TLR. For example, lipopolysaccharide (LPS) may be a TLR agonist through TLR2 or TLR4 (Tsan et al., 2004 J. Leuk. Biol. 76:514; Tsan et al., 2004 Am. J. Physiol. Cell Phsiol. 286:C739; Lin et al., 2005 Shock 24:206); poly(inosine-cytidine) (polyI:C) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG 10101 Bayes et al. Methods Find Exp Clin Pharmacol 27:193; Vollmer et al. Expert Opinion on Biological Therapy 5:673; Vollmer et al., 2004 Antimicrob. Agents Chemother. 48:2314; Deng et al., 2004 J. Immunol. 173:5148) may be TLR agonists through TLR9 (Andaloussi e a., 2006 Glia 54:526; Chen et al., 2006 J. Immunol. 177:2373); peptidoglycans may be TLR2 and/or TLR6 agonists (Soboll et al., 2006 Biol. Reprod. 75:131; Nakao et al., 2005 J. Immunol. 174:1566); 3M003 (4-amino-2-(ethoxymethyl)-.alpha.,.alpha.-dimethyl-6,7,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 J. Immunol. 174:1259) may be a TLR7 agonist (Johansen 2005 Clin. Exp. Allerg. 35:1591) and/or a TLR8 agonist (Johansen 2005); flagellin may be a TLR5 agonist (Feuillet et al., 2006 Proc. Nat. Acad. Sci. USA 103:12487); a profilin may be a TLR11 agonist (Hedhli et al., 2009, Vaccine, 27(16):2274-87); a lipopeptide may be a TLR1, TLR2, and/or TLR6 agonist (Gao et al., 2013, Vaccine, 31(26): 2796-803); and hepatitis C antigens may act as TLR agonists through TLR7 and/or TLR9 (Lee et al., 2006 Proc. Nat. Acad. Sci. USA 103:1828; Horsmans et al., 2005 Hepatol. 42:724). Other TLR agonists are known (e.g., Schirmbeck et al., 2003 J. Immunol. 171:5198) and may be used according to certain of the presently described embodiments.

For example, and by way of background (see, e.g., U.S. Pat. No. 6,544,518) immunostimulatory oligonucleotides containing ummethylated CpG dinucleotides ("CpG") are known as being adjuvants when administered by both systemic and mucosal routes (WO 96/02555, EP 468520, Davis et al., J. Immunol, 1998. 160(2):870-876; McCluskie and Davis, J. Immunol., 1998, 161(9):4463-6). CpG is an abbreviation for cytosine-guanosine dinucleotide motifs present in DNA. The central role of the CG motif in immuno stimulation was elucidated by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., Proc. Natl. Acad. Sci., USA, 1998, 95(26), 15553-8).

In some embodiments, the oligonucleotides for use as an adjuvant of the present invention contain two or more dinucleotide CpG motifs separated by at least three, more preferably at least six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Examples of preferred oligonucleotides have sequences that are disclosed in the following publications; for certain herein disclosed embodiments the sequences preferably contain phosphorothioate modified internucleotide linkages: (1) CPG 7909: Cooper et al., "CPG 7909 adjuvant improves hepatitis B virus vaccine seroprotection in antiretroviral-treated HIV-infected adults." AIDS, 2005 Sep. 23; 19(14): 1473-9; (2) CpG 10101: Bayes et al., "Gateways to clinical trials." Methods Find. Exp. Clin. Pharmacol. 2005 April; 27(3):193-219; and (3) Vollmer J., "Progress in drug development of immunostimulatory CpG oligodeoxynucleotide ligands for TLR9." Expert Opinion on Biological Therapy. 2005 May; 5(5): 673-682.

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilizing an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phosphodiesters. Other internucleotide bonds which stabilize the oligonucleotide may also be used.

In certain embodiments, the adjuvant is a TLR4 agonist. In some embodiments, the TLR4 agonist used in a composition of the invention comprises a glucopyranosyl lipid adjuvant (GLA), such as those described in U.S. Patent Publication Nos. US2007/021017, US2009/045033, US2010/037466, and US 2010/0310602, the contents of which are incorporated herein by reference in their entireties. In some embodiments, the adjuvant used in a composition of the invention herein is an attenuated lipid A derivative (ALD). ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay (CELD50) ALDs useful according to the subject invention include monophosphoryl lipid A (MLA) and 3-deacylated monophosphoryl lipid A (3D-MLA). MLA and 3D-MLA are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 U.S. Pat. No. 4,912,094 to Myers, et al., also assigned to Ribi ImmunoChem Research, Inc., embodies 3-deacylated monophosphoryl lipid A and a method for its manufacture.

In some embodiments, response modifiers such as imidazoquinoline and other immune response modifiers known in the art and may also be included as adjuvants in certain presently disclosed embodiments. Certain preferred imidazoquinoline immune response modifiers include, by way of non-limiting example, resiquimod (R848), imiquimod and gardiquimod (Hemmi et al., 2002 Nat. Immunol. 3:196; Gibson et al., 2002 Cell. Immunol. 218:74; Gorden et al., 2005 J. Immunol. 174:1259); these and other imidazoquinoline immune response modifiers may, under appropriate conditions, also have TLR agonist activity as described herein. Other immune response modifiers are the nucleic acid-based double stem loop immune modifiers (dSLIM). Specific examples of dSLIM that are contemplated for use in certain of the presently disclosed embodiments can be found in Schmidt et al., 2006 Allergy 61:56; Weihrauch et al. 2005 Clin Cancer Res. 11(16):5993-6001; Modern Biopharmaceuticals, J. Knablein (Editor). John Wiley & Sons, Dec. 6, 2005. (dSLIM discussed on pages 183 to about 200), and from Mologen A G (Berlin, FRG: [retrieved online on Aug. 18, 2006, see worldwide web at mologen.com/English/04.20-dSLIM.shtml]).

In some embodiments, an adjuvant used in a composition described herein is a polysaccharide derived from bacteria or plants. Non-limiting examples of polysaccharide-based adjuvants that can be used alone or in combination with one or more additional adjuvant in a composition described herein include glucans (e.g., beta glucans), dextrans (e.g., sulfated and diethylaminoethyl-dextrans), glucomannans, galactomannans, levans, xylans, fructans (e.g., inulin), chitosan, endotoxins (e.g., lipopolysaccharide), biobran MGN-3, polysaccharides from *Actinidia eriantha*, eldexomer, and variations thereof.

In some embodiments, an adjuvant used in a composition described herein is a proteosome or subunit thereof. In some embodiments, an adjuvant used in a composition described herein comprises identical or different antigenic peptide sequences assembled around a lysine core. In some embodiments, an adjuvant used in a composition described herein is a toxin (e.g., a bacterial toxin). In some embodiments, the toxin is from one or more bacteria selected from the group consisting of *Escherichia coli, Vibrio cholera, Bordetella pertussis*, and *Bordetella parapertussis*.

In some embodiments, an adjuvant used in a composition described herein (e.g., themostable dry powder vaccine) is a delivery adjuvant. A delivery adjuvant can serve as an adjuvant and/or can deliver an antigen. Non-limiting examples of an adjuvant that can be used alone or in combination with one or more additional adjuvant in a composition described herein includes mineral salts (e.g., calcium phosphate), emulsions (e.g., squalene in water), liposomes (e.g., DPPC:cholesterol liposomes), virosomes (e.g., immunopotentiating reconstituted influenza virosomes), and microspheres.

Other adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a composition described herein include Pluronic® L121 (BASF Corp., Mount Olive, N.J.; see, e.g., Yeh et al., 1996 Pharm. Res. 13:1693; U.S. Pat. No. 5,565,209), CRL1005 (e.g., Triozzi et al., 1997 Clin Canc. Res. 3:2355), poly(lactic-co-glycolic acid) (PLGA), poly(lactic acid) (PLA), poly-(D,L-lactide-co-glycolide) (PLG), and polyl:C. (See, e.g., Powell and Newman, "Vaccine design—The Subunit and Adjuvant Approach", 1995, Plenum Press, New York).

In some embodiments, an adjuvant used in a composition described herein (e.g., thermostable dry powder vaccine) is an organic adjuvant. Organic adjuvants can be adjuvants that are derived from living organisms or chemically contain carbon. In some embodiment, the adjuvant is a peptide derived from a microbial cell wall (e.g., muramyl dipeptide and variants thereof). In some embodiments, the adjuvant is trehalose 6,6'-dimycolate or variants thereof. See Schweneker et al., 2013, Immunobiology, 218(4):664-73. In some embodiments, the adjuvant is stearyl tyrosine.

Saponins and saponin mimetics, including QS21 and structurally related compounds conferring similar effects and referred to herein as QS21 mimetics. (see, e.g., U.S. Pat. No. 5,057,540; EP 0 362 279 B1; WO 95/17210), plant alkaloids such as tomatine, detergents such as (but not limited to) saponin, polysorbate 80, Span 85 and stearyl tyrosine, an imidazoquinoline immune response modifier, and a double stem loop immune modifier (dSLIM, e.g., Weeratna et al., 2005 Vaccine 23:5263) may be used as an adjuvant according to certain of the presently described embodiments.

In some embodiments, the adjuvant used in a composition described herein is a saponin or a saponin mimetic. Detergents including saponins are taught in, e.g., U.S. Pat. No. 6,544,518; Lacaille-Dubois, M and Wagner H. (1996 Phytomedicine 2:363-386), U.S. Pat. No. 5,057,540, Kensil, Crit Rev Ther Drug Carrier Syst, 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. QS21 may comprise an HPLC purified non-toxic fraction derived from the bark of Quillaja *Saponaria* Molina. The production of QS21 is disclosed in U.S. Pat. No. 5,057,540. (See also U.S. Pat. Nos. 6,936,255, 7,029,678 and 6,932,972.) Also described in these references is the use of QS7 (a non-haemolytic fraction of Quil-A) which acts as a potent adjuvant for systemic vaccines. Use of QS21 is further described in Kensil et al. (1991. J. Immunology 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., Vaccine, 10(9):572-577, 1992).

In some embodiments, the adjuvant is an "immunostimulatory complexes" known as ISCOMS (e.g., U.S. Pat. Nos. 6,869,607, 6,846,489, 6,027,732, 4,981,684), including saponin-derived ISCOMATRIX®, which is commercially available, for example, from Iscotec (Stockholm, Sweden) and CSL Ltd. (Parkville, Victoria, Australia).

Escin is another detergent related to the saponins for use in the adjuvant compositions of the embodiments herein disclosed. Escin is described in the Merck index (12th Ed.: entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin (also known as aescin) have been purified and shown to be biologically active (Yoshikawa M, et al. (Chem Pharm Bull (Tokyo) 1996 August; 44(8): 1454-1464)).

Digitonin is another detergent, also being described in the Merck index (12th Ed., entry 3204) as a saponin, being derived from the seeds of *Digitalis purpurea* and purified according to the procedure described by Gisvold et al., J. Am. Pharm. Assoc., 1934, 23, 664; and Rubenstroth-Bauer, Physiol. Chem., 1955, 301, 621.

In some embodiments, an adjuvant used in a composition described herein (e.g., thermostable dry powder vaccine) is an inorganic adjuvant. Inorganic adjuvants can be adjuvants that are generally not carbon-based such as, for example, mineral salts, emulsions, and calcium phosphates. Mineral salts adjuvants contemplated herein include, but are not limited to, aluminum-based compounds such as aluminum phosphate and aluminum hydroxide. As used herein, calcium phosphate adjuvants include, but are not limited to, calcium ions (Ca2+) together with orthophosphates (PO43−), metaphosphates (PO3−), or pyrophosphates (P2O74−).

As also noted above, one type of adjuvant for use in a composition as described herein may be the aluminum adjuvants, which are generally referred to as "alum." Alum adjuvants are based on the following: aluminum oxy-hydroxide; aluminum hydroxyphosphate; or various proprietary salts. Vaccines that use alum adjuvants may include vaccines for tetanus strains, HPV, hepatitis A, inactivated polio virus, and other antigens as described herein. Alum adjuvants are advantageous because they have a good safety record, augment antibody responses, stabilize antigens, and are relatively simple for large-scale production. (Edelman 2002 Mol. Biotechnol. 21:129-148; Edelman, R. 1980 Rev. Infect. Dis. 2:370-383.).

In some embodiments, the compositions of the present invention comprise an adjuvant. In some embodiments, the adjuvant is a TLR4 agonist. In some embodiments, the adjuvant is present at a concentration of about 0.5 µg/mL to about 12 mg/mL. In some embodiments, the adjuvant is present at a concentration of about 0.5 µg/mL, about 1 µg/mL, about 2 µg/mL, about 3 µg/mL, about 4 µg/mL, about 5 µg/mL, about 6 µg/mL, about 7 µg/mL, about 8 µg/mL, about 9 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, or about 100 µg/mL. In some embodiments, the adjuvant is an MPL or GLA described herein. In some embodiments, the adjuvant is present at a concentration of about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, or about 12 mg/mL.

Suitable adjuvants for use in certain compositions described herein (e.g., a thermostable spray dried vaccine composition) include commercially available adjuvants such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); AddaVax (InvivoGen); MF59 (Norvartis); AS03 (GlaxoSmithKline); AS01B (GlaxoSmithKline); AS02A (GlaxoSmithKline).

Some embodiments as provided herein include compositions (e.g., thermostable dry powder vaccine compositions), that contain one adjuvant and at least one more adjuvant that is different from the first adjuvant. For example, a composition provided herein may comprise GLA and a second adjuvant other than GLA. In some embodiments, a composition provided herein comprises two, three, four or five adjuvants. In some embodiments, a composition provided herein comprises two adjuvants.

An adjuvant as described herein includes an adjuvant that, when administered to a subject such as a human (e.g., a human patient), a non-human primate, a mammal or another higher eukaryotic organism having a recognized immune system, is capable of altering (i.e., increasing or decreasing in a statistically significant manner, and in certain embodiments, enhancing or increasing) the potency and/or longevity of an immune response. (See, e.g., Powell and Newman, "Vaccine design—The Subunit and Adjuvant Approach", 1995, Plenum Press, New York). In certain embodiments disclosed herein GLA and a desired antigen, and optionally one or more adjuvant, may so alter, e.g., elicit or enhance, an immune response that is directed against the desired antigen.

Antigens for Use in Thermostable Spray Dried (Dry Powder) Vaccine Compositions

In some embodiments the thermostable vaccine composition is used to elicit or enhance the immunoreactivity or an immune response in a host to an antigen.

In some embodiments the antigen may be already present in the host such as an autoimmune antigen, allergen, or cancer antigen and the vaccine composition may only include the stable emulsion and optionally an adjuvant that when administered elicits or enhances the immunoreactivity to the antigen already present in a subject. This administration of a vaccine composition comprising the thermostable spray dried adjuvant composition for eliciting an immune response to an antigen already present in a host as used herein is a monotherapy.

In some embodiments, a vaccine composition described herein comprises one or more antigens.

An antigen, for use in certain embodiments of the herein described compositions and methods for generating and using such compositions, may be any target epitope, molecule (including a biomolecule), molecular complex (including molecular complexes that contain biomolecules), sub-cellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

In some embodiments, an antigen may be present at any concentration sufficient to elicit or enhance immunoreactivity in a subject at a desired level. In some embodiments, an antigen may be present at a concentration range of about 0.1 µg/mL to about 10 mg/mL, including but not limited to about 1 µg/mL to about 5 mg/mL, about 1 µg/mL to about 2 mg/mL, about 2.5 µg/mL to about 1 mg/mL, about 5 µg/mL to about 500 µg/mL, about 10 µg/mL to about 500 µg/mL, 0.1 µg/mL to about 250 µg/mL, about 1 µg/mL to about 250 µg/mL, about 2.5 µg/mL to about 250 µg/mL, about 5 µg/mL to about 250 µg/mL, about 10 µg/mL to about 250 µg/mL, 0.1 µg/mL to about 100 µg/mL, about 1 µg/mL to about 100

μg/mL, about 2.5 μg/mL to about 100 μg/mL, about 5 μg/mL to about 100 μg/mL, 0.1 μg/mL to about 50 μg/mL, about 1 μg/mL to about 50 μg/mL, about 2.5 μg/mL to about 50 μg/mL, 0.1 μg/mL to about 2.5 μg/mL, about 1 μg/mL to about 2.5 μg/mL, or about 0.1 μg/mL to about 10 μg/mL. The concentrations provided refer to the concentrations of the antigen in either the oil-in-water emulsion formulation prior to spray drying or in the dry powder or in the dry powder upon reconstitution.

In certain embodiments the compositions described herein (e.g., a thermostable spray dried vaccine composition) comprise an antigen or antigenic composition capable of eliciting an immune response against a human or other mammalian pathogen, which antigen or antigenic composition may include a composition derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gp1, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, or M proteins, or combinations thereof).

In some embodiments the compositions described herein (e.g., a thermostable spray dried vaccine composition) comprise an antigen or antigenic composition capable of eliciting an immune response against a human or other mammalian pathogen, which antigen or antigenic composition may include a composition derived from one or more bacterial pathogens such as *Neisseria* spp., including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexneri; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci;* Leptospira spp., including *L. interrogans; Treponema* spp., including *T. pallidum* (for example the rare outer membrane proteins), *T. denticola, T. hyodysenteriae*; or other bacterial pathogens.

In certain embodiments the compositions described herein (e.g., a thermostable spray dried vaccine composition) comprise an antigen or antigenic composition capable of eliciting an immune response against a human or other mammalian pathogen, which antigen or antigenic composition may include a composition derived from one or more parasites (See, e.g., John, D. T. and Petri, W. A., Markell and Voge's Medical Parasitology—9th Ed., 2006, WB Saunders, Philadelphia; Bowman, D. D., Georgis' Parasitology for Veterinarians-8th Ed., 2002, WB Saunders, Philadelphia) such as *Plasmodium* spp., including *P. falciparum; Toxoplasma* spp., including *T. gondii* (for example SAG2, SAGS, Tg34); *Entamoeba* spp., including *E. histolytica; Babesia* spp., including *B. microti; Trypanosoma* spp., including *T. cruzi;* Giardia spp., including *G. lamblia;* Leshmania spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis,* and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). Certain embodiments may therefore contemplate vaccine compositions that include an antigen derived from *Schistosoma* spp., *Schistosoma mansonii, Schistosoma haematobium,* and/or *Schistosoma japonicum,* or derived from yeast such as *Candida* spp., including *C. albicans; Cryptococcus* spp., including *C. neoformans.*

In some embodiments, a composition described herein comprises at least two heterologous polypeptides of a *Mycobacterium* species of the tuberculosis complex. A *Mycobacterium* species of the tuberculosis complex includes those species traditionally considered as causing the disease tuberculosis, as well as *Mycobacterium* environmental and opportunistic species that cause tuberculosis and lung disease in immune compromised patients, such as patients with AIDS, e.g., *Mycobacterium tuberculosis* (Mtb), *Mycobacterium bovis*, or *Mycobacterium africanum*, BCG, *Mycobacterium avium, Mycobacterium intracellulare, Mycobacterium celatum, Mycobacterium genavense, Mycobacterium haemophilum, Mycobacterium kansasii, Mycobacterium simiae, Mycobacterium vaccae, Mycobacterium fortuitum*, and *Mycobacterium scrofulaceum* (see, e.g., Harrison's Principles of Internal Medicine, volume 1, pp. 1004-1014 and 1019-1020). The sequences of antigens from *Mycobacterium* species are readily available. For example, *Mycobacterium tuberculosis* sequences can be found in Cole et al., Nature 393:537 (1998) and can be found at websites such as those maintained by the Wellcome Trust, Sanger Institute and Institut Pasteur.

Other specific antigens for *M. tuberculosis* that may be used in a composition described herein are for example Th Ra12, Tb H9, Tb Ra35, Tb38-1, Erd 14, DPV, MTI, MSL, mTTC2 and hTCC1 (WO 99/51748).

Proteins for *M. tuberculosis* also include fusion proteins and variants thereof where at least two, preferably three polypeptides of *M. tuberculosis* are fused into a larger protein. In certain embodiments, fusion proteins include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647.

In certain embodiments, a composition described herein comprises an isolated fusion protein comprising a combination of two or more covalently linked *M. tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv151 1 and Rv3875, and antigens having at least 90% identity to any of the foregoing sequences.

In certain embodiments, a composition described herein comprises the ID93 fusion protein, which comprises the antigens Rv2608, Rv3619, Rv3620 and Rv1813 or a sequence having at least 90% identity to the combination of antigens. ID93 antigens are described in United States Patent Application number 20160324783, published Nov. 10, 2016 (Single Vial Vaccine Formulations), herein incorporated by reference in its entirety as SEQ ID NOS:1-8. In another embodiment, the composition comprises the ID93 fusion protein, which comprises the antigens Rv2608, Rv3619, Rv3620 and Rv1813, wherein the sequences of the antigens are from *M. tuberculosis*. In another embodiment, the ID93 fusion protein comprises a sequence set forth in SEQ ID NO: 1, or a sequence having at least 90% identity thereto. In some embodiments, the fusion protein comprises a sequence set forth in SEQ ID NO:2, or a sequence having at least 90% identity thereto. In some embodiments, the therapeutic vaccine comprises a fusion protein comprising a combination of *Mycobacterium* antigens Rv2608, Rv3620 and Rv1813, or a sequence having at least 90% identity the combination of antigens. In some embodiments, the *Mycobacterium* antigens Rv2608, Rv3620 and Rv1813 are *M. tuberculosis* antigens Rv2608, Rv3620 and Rv1813. In some embodiments, the fusion protein comprises a sequence set forth in SEQ ID NO:3 or 4, or a sequence having at least 90% identity to SEQ ID NO:3 or SEQ ID NO:4. In some embodiments, antigen Rv1813 comprises the amino acid sequence of SEQ ID NO:5. In some embodiments, antigen Rv3620 comprises the amino acid sequence of SEQ ID NO:6. In some embodiments, antigen Rv2608 comprises the amino acid sequence of SEQ ID NO:7. In some embodiments, antigen Rv3619 comprises the amino acid sequence of SEQ ID NO: 8. One skilled in the art would understand that one or more N-terminal amino acids (such as signal sequences) may be removed. These sequences are described in U.S. Pat. No. 8,486,414 which is incorporated herein by reference. In some embodiments, the composition comprises the ID93 fusion protein, or a polynucleotide encoding the same, which comprises four antigens belonging to families of Mtb proteins associated with virulence (Rv2608, Rv3619, Rv3620) or latency (Rv1813), as described in US Patent Application Publication No. 2010/0129391 (specifically incorporated herein by reference in its entirety).

In some embodiments, a composition described herein comprises an antigen for *Chlamydia*. Antigens for *Chlamydia* include for example the High Molecular Weight Protein (HWMP) (WO 99/17741), ORF3 (EP 366 412), and putative membrane proteins (Pmps). Other *Chlamydia* antigens of the composition can be selected from the group described in WO 99128475. In some embodiments, a composition described herein comprises antigens derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other bacterial antigens are derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Derivatives of Hepatitis B Surface antigen are well known in the art and include, inter alia, those PreS1, Pars2 S antigens set forth described in European Patent applications EP-A414 374; EP-A-0304 578, and EP 198474. In some embodiments, a composition described herein comprises the HIV-1 antigen, gp120, especially when expressed in CHO cells. In a further embodiment, the composition comprises gD2t as hereinabove defined.

In some embodiments, a composition described herein comprises an antigen derived from the Human Papilloma Virus (HPV) considered to be responsible for genital warts (HPV 6 or HPV 11 and others), and the HPV viruses responsible for cervical cancer (HPV16, HPV18 and others). In some embodiments, the composition is a genital wart prophylactic, or therapeutic, vaccine comprising L1 particles or capsomers, and fusion proteins comprising one or more antigens selected from the HPV 6 and HPV 11 proteins E6, E7, L1, and L2. Certain forms of fusion protein include L2E7 as disclosed in WO 96/26277, and proteinD(1/3)-E7 disclosed in GB 9717953.5 (PCT/EP98/05285). In some embodiments, the composition is an HPV cervical infection or cancer, prophylaxis or therapeutic vaccine, comprising HPV 16 or 18 antigens. For example, L1 or L2 antigen monomers, or L1 or L2 antigens presented together as a virus like particle (VLP) or the L1 alone protein presented alone in a VLP or capsomere structure. Such antigens, virus like particles and capsomere are per se known. See for example WO94/00152, WO94/20137, WO94/05792, and WO93/02184.

Additional early proteins may be included alone or as fusion proteins such as E7, E2 or preferably F5 for example; some embodiments include a VLP comprising L1E7 fusion proteins (WO 96/11272). In some embodiments, HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such a composition (e.g., a thermostable spray dried vaccine composition) may optionally contain either or both E6 and E7 proteins front HPV 18, preferably in the form of a Protein D-E6 or Protein D-E7 fusion protein or Protein D E6/E7 fusion protein. A composition of the present invention may additionally comprise antigens from other HPV strains, preferably from strains HPV 31 or 33.

Compositions of the present invention may further comprise antigens derived from parasites that cause Malaria. For example, antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. An embodiment of the present invention is a Malaria vaccine wherein the antigenic preparation comprises a combination of the RTS,S and TRAP antigens. Other plasmodia antigens that are likely candidates to be components of a multistage Malaria vaccine are *P. falciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

Certain herein disclosed embodiments contemplate an antigen that is derived from at least one infectious pathogen such as a bacterium, a virus or a fungus, including an Actinobacterium such as *M. tuberculosis* or *M. leprae* or another *mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus, Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia*, and *Leishmania*.

For example, in embodiments of compositions containing antigens derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Compositions and methods are known in the art for identifying subjects having, or suspected of being at risk for having, an infection with an infectious pathogen as described herein.

For example, the bacterium *Mycobacterium tuberculosis* causes tuberculosis (TB). The bacteria usually attack the lungs but can also attack the kidney, spine, and brain. If not treated properly, TB disease can be fatal. The disease is spread from one person to another in the air when an infected person sneezes or coughs. In 2003, more than 14,000 cases of TB were reported in the United States.

Although tuberculosis can generally be controlled using extended antibiotic therapy, such treatment is not sufficient to prevent the spread of the disease and concerns exist regarding the potential selection for antibiotic-resistant strains. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance. (e.g., U.S. Pat. No. 7,087,713).

Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48 72 hours after injection, which indicates exposure to Mycobacterial antigens. Sensitivity and specificity have, however, been a problem with this test, and individuals vaccinated with BCG cannot be distinguished from infected individuals. (e.g., U.S. Pat. No. 7,087,713).

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-gamma), which, in turn, has been shown to trigger the anti-mycobacterial effects of macrophages in mice. While the role of IFN-gamma in humans is less clear, studies have shown that 1,25-dihydroxy-vitamin D3, either alone or in combination with IFN-gamma or tumor necrosis factor-alpha, activates human macrophages to inhibit *M. tuberculosis* infection. Furthermore, it is known that IFN-gamma stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection, see Chan and Kaufmann, in Tuberculosis: Pathogenesis, Protection and Control, Bloom (ed.), ASM Press. Washington, D.C. (1994).

Existing compounds and methods for diagnosing tuberculosis or for inducing protective immunity against tuberculosis include the use of polypeptides that contain at least one immunogenic portion of one or more *Mycobacterium* proteins and DNA molecules encoding such polypeptides. Diagnostic kits containing such polypeptides or DNA sequences and a suitable detection reagent may be used for the detection of *Mycobacterium* infection in patients and biological samples. Antibodies directed against such polypeptides are also provided. In addition, such compounds may be formulated into compositions described herein for immunization against *Mycobacterium* infection. (U.S. Pat. Nos. 6,949,246 and 6,555,653).

Malaria was eliminated in many parts of the world in the 1960s, but the disease still persists and new strains of the disease are emerging that are resistant to existing drugs. Malaria is a major public health problem in more than 90 countries. Nine out of ten cases of malaria occur in sub-Saharan Africa. More than one third of the world's population is at risk, and between 350 and 500 million people are infected with malaria each year. Forty-five million pregnant women are at risk of contracting malaria this year. Of those individuals already infected, more than 1 million of those infected die each year from what is a preventable disease. The majority of those deaths are children in Africa.

Malaria is usually transmitted when a person is bitten by an infected female *Anopheles* mosquito. To transmit the mosquito must have been infected by having drawn blood from a person already infected with malaria. Malaria is caused by a parasite and the clinical symptoms of the disease include fever and flu-like illness, such as chills, headache, muscle aches, and tiredness. These symptoms may be accompanied by nausea, vomiting, and diarrhea. Malaria can also cause anemia and jaundice because of the loss of red blood cells.

Infection with one type of malaria, *Plasmodium falciparum*, if not promptly treated, may cause kidney failure, seizures, mental confusion, coma, and death.

An in vitro diagnostic method for malaria in an individual is known, comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed (see, e.g., U.S. Pat. No. 7,087,231).

Expression and purification of a recombinant *Plasmodium falciparum* (3D7) AMA-1 ectodomain have been described. Previous methods have produced a highly purified protein which retains folding and disulfide bridging of the native molecule. The recombinant AMA-1 is useful as a diagnostic reagent, as well as in antibody production, and as a protein for use alone, or as part of, a vaccine to prevent malaria. (U.S. Pat. No. 7,029,685). Polynucleotides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection. (U.S. Pat. No. 6,706,872) Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection (see, e.g., U.S. Pat. No. 6,231,861).

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. (U.S. Pat. No. 7,060,276) Similarly known are the expression and purification of a recombinant *Plasmodium falciparum* (3D7) MSP-1.sub.42, which retains folding and disulfide bridging of the native molecule. The recombinant MSP-1.sub.42 is useful as a diagnostic reagent, for use in antibody production, and as a vaccine. (U.S. Pat. No. 6,855,322).

Diagnostic methods for the detection of human malaria infections to identify a subject having or suspected of being at risk for having an infection with a malaria infectious pathogen are thus known according to these and related disclosures. Specifically, for example, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the above-described reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis.

Detection of the reduced APAD in the foregoing manner provides a positive indication of malaria infection (e.g., U.S. Pat. No. 5,124,141). In another methodology for diagnosing malaria, a polypeptide comprising a characteristic amino acid sequence derived from the *Plasmodium falciparum* antigen GLURP, is recognized in a test sample by a specific antibody raised against or reactive with the polypeptide. (U.S. Pat. No. 5,231,168).

Leishmaniasis is a widespread parasitic disease with frequent epidemics in the Indian subcontinent, Africa, and Latin America and is a World Health Organization priority for vaccine development. A complex of different diseases, *Leishmania* parasites cause fatal infections of internal organs, as well as serious skin disease. One of the most devastating forms of leishmaniasis is a disfiguring infection of the nose and mouth. The number of cases of leishmaniasis are increasing, and it is now out of control in many areas. Leishmaniasis is also on the rise in some developed countries, specifically southern Europe as a result of HIV infection. Available drugs are toxic, expensive, and require long-term daily injections.

*Leishmania* are protozoan parasites that inhabit macrophages or the white blood cells of the immune system. The parasites are transmitted by the bite of small blood sucking insects (sand flies), which are difficult to control, as they inhabit vast areas of the planet.

Visceral leishmaniasis is the most dangerous of the three manifestations of the disease. It is estimated that about 500,000 new cases of the visceral form (kala-azar or "the killing disease") occur each year. More than 200 million people are currently at risk for contracting visceral leishmaniasis. Over 90 percent of visceral leishmaniasis cases occur in India, Bangladesh, Sudan, Brazil, and Nepal. Most of the deaths occur in children. Those with the cutaneous forms are often left permanently disfigured.

*Leishmania* infections are difficult to diagnose and typically involve histopathologic analysis of tissue biopsy specimens. Several serological and immunological diagnostic assays have, however, been developed. (U.S. Pat. No. 7,008, 774; Senaldi et al., (1996) J. Immunol. Methods 193:9 5; Zijlstra, et al., (1997) Trans. R. Soc. Trop. Med. Hyg. 91:671 673; Badaro, et al., (1996) J. Inf. Dis. 173:758 761; Choudhary, S., et al., (1992) J. Comm. Dis. 24:32 36; Badaro, R., et al., (1986) Am. J. Trop. Med. Hyg. 35:72 78; Choudhary, A., et al., (1990) Trans. R. Soc. Trop. Med. Hyg. 84:363 366; and Reed, S. G., et al., (1990) Am. J. Trop. Med. Hyg. 43:632 639). The promastigotes release metabolic products into the culture medium to produce conditioned medium. These metabolic products are immunogenic to the host. See Schnur, L. F., et al., (1972) lsrl. J. Med. Sci. 8:932 942; Sergeiev, V. P., et al., (1969) Med. Parasitol. 38:208 212; El-On, J., et al., (1979) Exper. Parasitol. 47:254 269; and Bray, R. S., et al., (1966) Trans. R. Soc. Trop. Med. Hyg. 60:605 609; U.S. Pat. Nos. 6,846,648, 5,912,166; 5,719,263; 5,411,865).

In some embodiments, an antigen is *Leishmania* antigen described in US 2009/0041798, US 2009/0291099, U.S. Pat. Nos. 8,410,258, 8,231,881, and WO 2012/064659, which are incorporated herein by reference. In some embodiments, the antigen is a fusion polypeptide comprising at least a *Leishmania* sterol 24-c-methyltransferase (SMT) polypeptide sequence and a *Leishmania* non-specific nucleoside hydrolase (NH) polypeptide sequence. In some embodiments, the *Leishmania* NH polypeptide sequence comprises at least an immunogenic portion of a sequence having at least 90% identity to a *Leishmania* NH sequence of *L. donovani, L. infantum* and *L. major*. In some embodiments, the *Leishmania* NH polypeptide sequence comprises at least an immunogenic portion of a sequence selected from the group consisting of SEQ ID NOs: 1, 3 and 5, or a sequence having at least 90% identity thereto. In some embodiments, the *Leishmania* SMT polypeptide sequence comprises at least an immunogenic portion of a sequence having at least 90% identity to a *Leishmania* SMT sequence of *L. donovani, L. infantum* and *L. major*. In some embodiments, the *Leishmania* SMT polypeptide sequence comprises at least an immunogenic portion of a sequence selected from the group consisting of SEQ ID NOs: 7, 9 and 11, or a sequence having at least 90% identity thereto. In some embodiments, the fusion polypeptide comprises an amino acid sequence set forth in SEQ ID NO: 13, or a sequence having at least 90% identity thereto. The sequences of SEQ ID NO:1, 3, 5, 7, 9, 11 and 13 are provided in WO 2012/064659 and US 20120114688, which are incorporated herein by reference.

About 40 million people around the world are infected with HIV, the virus that causes AIDS. Around 3 million people die of the disease each year, 95 percent of them in the developing world. Each year, close to 5 million people become infected with HIV. Currently, sub-Saharan African carries the highest burden of disease, but it is quickly spreading to other countries such as India, China, and Russia. The epidemic is growing most rapidly among minority populations. In the United States there have been more than 950,000 cases of AIDS reported since 1981. AIDS hits people during their most productive years. Women, for both biological and social reasons, have an increased risk for HIV/AIDS.

AIDS is caused by human immunodeficiency virus (HIV), which kills and damages cells of the body's immune system and progressively destroys the body's ability to fight infections and certain cancers. HIV is spread most commonly by having unprotected sex with an infected partner. The most robust solution to the problem is preventing the virus from spreading. Making a safe, effective, and affordable HIV vaccine is one way to reach this goal. Across the world, fewer than one in five people at high risk for HIV infection have access to effective prevention.

Methods for diagnosing HIV infections are known, including by virus culture, PCR of definitive nucleic acid sequences from patient specimens, and antibody tests for the presence of anti-HIV antibodies in patient sera, (see e.g., U.S. Pat. Nos. 6,979,535, 6,544,728, 6,316,183, 6,261,762, 4,743,540.).

According to certain other embodiments as disclosed herein, the compositions and methods of use may include an antigen that is derived from a cancer cell, as may be useful for the immunotherapeutic treatment of cancers. For example, the composition may find utility with tumor rejection antigens such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 Current Opinions in Immunology 8, pps 628-636; Van den Eynde et al., International Journal of Clinical & Laboratory Research (1997 & 1998); Correale et al. (1997), Journal of the National Cancer Institute 89, p. 293. These non-limiting examples of cancer antigens are expressed in a wide range of tumor types such as melanoma, lung carcinoma, sarcoma and bladder carcinoma. See, e.g., U.S. Pat. No. 6,544,518. Other tumor-specific antigens are suitable for use in compositions described herein include, but are not restricted to, tumor-specific or tumor-associated gangliosides such as GM.sub.2, and GM.sub.3 or conjugates thereof to carrier proteins; or an antigen for use in a GLA vaccine composition for eliciting or enhancing an anti-cancer immune response may be a self peptide hormone such as whole length Gonadotrophin hormone releasing hormone (GnRH, WO 95/20600), a short 10 amino acid long peptide, useful in the treatment of many cancers.

In another embodiment prostate antigens are used, such as Prostate specific antigen (PSA), PAP, PSCA (e.g., Proc. Nat. Acad. Sci. USA 95(4) 1735-1740 1998), PSMA or, in a preferred embodiment an antigen known as Prostase. (e.g., Nelson, et al., Proc. Natl. Acad. Sci. USA (1999) 96: 3114-3119; Ferguson, et al. Proc. Natl. Acad. Sci. USA 1999. 96, 3114-3119; WO 98/12307; U.S. Pat. No. 5,955, 306; WO 98/20117; U.S. Pat. Nos. 5,840,871 and 5,786,148; WO 00/04149. Other prostate specific antigens are known from WO 98/137418, and WO/004149. Another is STEAP (PNAS 96 14523 14528 7-12 1999).

Other tumor associated antigens useful in the context of the present invention include: Plu-1 (J Biol. Chem 274 (22) 15633-15645, 1999), HASH-1, HasH-2, Cripto (Salomon et al Bioessays 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

The herein disclosed embodiments pertaining to compositions comprising a cancer antigen may be useful against any cancer characterized by tumor associated antigen expression, such as HER-2/neu expression or other cancer-specific or cancer-associated antigens.

Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohisto-cytochemical and immunohistopathological examination of patient samples (e.g., blood, skin biopsy, other tissue biopsy, surgical specimens, etc.), PCR tests for defined genetic (e.g., nucleic acid) markers, serological tests for circulating cancer-associated antigens or cells bearing such antigens, or for antibodies of defined specificity, or other methodologies with which those skilled in the art will be familiar. See, e.g., U.S. Pat. Nos. 6,734,172; 6,770,445; 6,893,820; 6,979,730; 7,060,802; 7,030,232; 6,933,123; 6,682,901; 6,587,792; 6,512,102; 7,078,180; 7,070,931; JP5-328975; Waslylyk et al., 1993 Eur. J Bioch. 211(7):18.

Compositions and methods according to certain embodiments of the present invention may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells (Akamizu et al., 1996; Kellerman et al., 1995; Raju et al., 1997; and Texier et al., 1992); pemphigus is cadherin-like pemphigus antigens such as desmoglein 3 and other adhesion molecules (Memar et al., 1996: Stanley, 1995; Plott et al., 1994; and Hashimoto, 1993); and thrombic thrombocytopenic purpura is antigens of platelets. (See, e.g., U.S. Pat. No. 6,929,796; Gorski et al. (Eds.), Autoimmunity, 2001, Kluwer Academic Publishers, Norwell, Mass.; Radbruch and Lipsky, P. E. (Eds.) Current Concepts in Autoimmunity and Chronic Inflammation (Curr. Top. Microbiol. and Immunol.) 2001, Springer, N.Y.)

Autoimmunity plays a role in more than 80 different diseases, including type 1 diabetes, multiple sclerosis, lupus, rheumatoid arthritis, scleroderma, and thyroid diseases. Vigorous quantitative estimates of morbidity for most autoimmune diseases are lacking. Most recent studies done in the late 1990s reveal that autoimmune diseases are the third most common major illness in the United States; and the most common autoimmune diseases affect more than 8.5 million Americans. Current estimates of the prevalence of the disease range from 5 to 8 percent of the United States population. Most autoimmune diseases disproportionately affect women. Women are 2.7 times more likely than men to acquire an autoimmune disease. Women are more susceptible to autoimmune diseases; men appear to have higher levels of natural killer cell activity than do women. (Jacobsen et al, Clinical Immunology and Immunopathology, 84:223-243, 1997.)

Autoimmune diseases occur when the immune system mistakes self tissues for nonself and mounts an inappropriate attack. The body can be affected in different ways from autoimmune diseases, including, for example, the gut (Crohn's disease) and the brain (multiple sclerosis). It is known that an autoantibody attacks self-cells or self-tissues to injure their function and as a result, causes autoimmune diseases, and that the autoantibody may be detected in the patient's serum prior to the actual occurrence of an autoimmune disease (e.g., appearance of clinical signs and symptoms). Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests (e.g., U.S. Pat. Nos. 6,919,210, 6,596, 501, 7,012,134, 6,919,078) while other autoimmune diagnostics may involve detection of a relevant metabolite (e.g., U.S. Pat. No. 4,659,659) or immunological reactivity (e.g., U.S. Pat. Nos. 4,614,722 and 5,147,785, 4,420,558, 5,298, 396, 5,162,990, 4,420,461, 4,595,654, 5,846,758, 6,660, 487).

In certain embodiments, the compositions of the invention will be particularly applicable in treatment of the elderly and/or the immunosuppressed, including subjects on kidney dialysis, subjects on chemotherapy and/or radiation therapy, transplant recipients, and the like. Such individuals generally exhibit diminished immune responses to vaccines and therefore use of the compositions of the invention can enhance the immune responses achieved in these subjects.

In other embodiments, the antigen or antigens used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):577-121). Exacerbations of COPD are often caused by bacterial (e.g. pneumococcal) infection (Clin Microbiol Rev. 2001 April; 14(2):336-63).

Oils for Use in the Thermostable Compositions

Certain embodiments contemplate compositions described herein that include an oil, which in some such embodiments may contribute adjuvant activity and in other such embodiments may additionally or alternatively provide a pharmaceutically acceptable carrier or excipient. Any number of suitable oils are known and may be selected for inclusion in the compositions based on the present disclosure. Examples of such oils, by way of illustration and not limitation, include squalene, synthetic squalene, biosynthetic squalene, mineral oil, grape seed oil, a synthetic isoprenoid, biosynthetic isoprenoid, polyprenol, olive oil, cholesterol, and a mannide monooleate.

An oil contemplated herein can be used in an emulsion system and such emulsion systems are referred to as an emulsion adjuvant. Emulsion adjuvants include oil-in-water, water-in-oil, or water-in-oil-in-water mixtures. Without being bound by theory, such emulsion adjuvants can function by enabling slow release of antigens to provide continued stimulation of the immune system. Certain emulsion adjuvants can also be used as a delivery system for other adjuvants including immunostimulatory adjuvants such as, but not limited to, CpG oligodeoxynucleotides (CpG ODN), glucopyranosyl lipid adjuvant (GLA), monophosphoryl lipid A (MLA), and 3-deacylated monophosphoryl lipid A (3D-MLA). Certain emulsion systems for formulating adjuvant compositions have been described, including single or multiphase emulsion systems. Oil-in-water emulsion adjuvants per se have been suggested to be useful as an adjuvant composition (EP 0 399 843B), also combinations of oil-in-water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil-in-water emulsions (U.S. Pat. No. 5,424,067; EP 0 480 981 B).

The oil emulsion adjuvants for use in the present invention may be natural or synthetic, and may be mineral or organic. Examples of mineral and organic oils will be readily apparent to the man skilled in the art. In a particular embodiment, a composition of the invention (e.g., a themostable spray dried vaccine) comprises an emulsion of oil-in-water wherein the adjuvant is incorporated in the oil phase. In order for an oil-in-water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any plant oil, vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used.

Squalene (2,6,10,15,19,23-Hexamethyl-2,6,10,14,18,22-tetracosahexaene), for example, is an unsaturated oil which is found in large quantities in shark-liver oil, and in lower quantities in olive oil, wheat germ nil, rice bran oil, and yeast, and is a particularly preferred oil for use in this invention. Squalene is a metabolizable oil by virtue of the fact that it is an intermediate in the biosynthesis of cholesterol (Merck index, 10th Edition, entry no. 8619). Illustrative metabolizable oils useful according to the subject invention include, but are not limited to, squalene, soybean oil, sesame oil and caprylic/capric acid triglycerides (MIGLYCOL 810 oil). In one embodiment, the metabolizable oil comprises squalene. In another embodiment, the metabolizable oil comprises one or more yeast-derived isoprenoids, such as yeast-derived squalene or related isoprenoid structure derived from yeast.

In some embodiments, the compositions of the present invention comprise a metabolizable oil that is present at a concentration of about 0.01%-5% v/v, about 0.01%-4% v/v, about 0.01%-3% v/v, about 0.01%-2% v/v, about 0.01%-1% v/v, or about 0.01%-0.5% v/v. In some embodiments, the metabolizable oil is present at a concentration of about 0.01% v/v, about 0.05% v/v, about 0.1% v/v, about 0.5% v/v, about 1% v/v, about 1.5% v/v, about 2% v/v, about 2.5% v/v, about 3% v/v, about 3.5% v/v, about 4% v/v, about 4.5% v/v, about 5% v/v, about 6% v/v, about 7% v/v, about 8% v/v, about 9% v/v, about 10% v/v, about 11% v/v, about 12% v/v, about 13% v/v, about 14% v/v, about 15% v/v, about 16% v/v, about 17% v/v, about 18% v/v, about 19% v/v, or about 20% v/v. In some embodiments, the metabolizable oil is present at a concentration of about 2% v/v. In some embodiments, the metabolizable oil is present at a concentration below 1% v/v. The percentages described refer to the percentages in either the oil-in-water emulsion formulation prior to spray drying, in the dry powder after spray drying or in the reconstituted dry powder.

The size of the oil droplets found within the stable oil-in-water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges.

The hydrophilic-lipophilic balance (HLB) of an emulsion allows for the estimation of the hydrophilic or lipophilic force of a surfactant. The HLB of an amphiphilic molecule is generally calculated as follows: HLB=(2O×Weight of the hydrophilic part)/(Weight of the amphiphilic molecule). The HLB may have a value ranging from 0 (for the most lipophilic molecule) to 20 (for the most hydrophilic molecule). According to the chemical composition of the surfactant (notably for example the addition of ethoxyl groups or of alkene oxides), this estimation may change and the domain of HLB value may increase (for example, the LUTROL F68® has a HLB of 29). With a mixture of surfactants, the HLB of the mixture is the addition of the HLB of each surfactant, balanced by its Weight ratio: HLB=(HLB surfactant X.times.Weight surfactant X)+(HLB surfactant Y.times.Weight surfactant Y)/(Weight surfactant X+Weight surfactant Y) In one embodiment of an emulsion made according to the present invention, the final HLB of the emulsion is from about 9 to about 12, preferably from about 9.5 to about 11.5 and more preferably from about 10 to about 11.5. In some embodiments the HLB of the emulsion is from about 10.5 to about 11.0. The method of producing oil-in-water emulsions is well known to the person skilled in the art. Commonly, the method comprises the mixing the oil phase with a suitable surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar)) could be adapted to produce smaller or larger volumes of emulsion. This adaptation could be achieved by routine experimentation comprising the measurement of the resultant emulsion until a preparation was achieved with oil droplets of the required diameter.

Therapeutic Compositions

In some embodiments the spray dry composition is a therapeutic composition and is useful for therapeutic purposes. Thus, in some embodiments, the compositions described comprise the dry powder composition and further comprises a bioactive agent for the treatment of a disease, condition, or disorder. In some embodiments the agent is useful for the treatment or prevention of allergy, cancer, infectious disease, autoimmunity, or addiction. In some embodiments the agent is useful for the stimulating, enhancing and/or modulating an immune response. Thus, while described as an "antigen," herein, the bioactive agent may also activate other therapeutic and immune response.

In some aspects of the disclosed embodiments, the compositions comprise cancer antigens or nucleic acids encoding a cancer antigen. In some embodiments, a vaccine composition comprises a cancer antigen will be useful against any cancer characterized by tumor associated antigen expression, such as HER-2/neu expression or other cancer-specific or cancer-associated antigens.

Compositions and methods according to certain embodiments of the present disclosure may also be used for the prophylaxis or therapy of autoimmune diseases, which include diseases, conditions or disorders wherein a host's or subject's immune system detrimentally mediates an immune response that is directed against "self tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells; pemphigus is cadherin-like pemphigus antigens such as desmoglein 3 and other adhesion molecules; and thrombic thrombocytopenic purpura is antigens of platelets.

The compositions provided herein may be used for inducing protective immunity, for example against tuberculosis include the use of polypeptides that contain at least one immunogenic portion of one or more *Mycobacterium* proteins and DNA and RNA molecules encoding such polypeptides. In addition, such compounds may be formulated into vaccines and/or pharmaceutical compositions for immunization against *Mycobacterium* infection.

In other embodiments, the compositions of the present disclosure include antigens associated with respiratory diseases, such as those caused or exacerbated by bacterial infection (e.g. pneumococcal), for the prophylaxis and therapy of conditions such as chronic obstructive pulmonary disease (COPD). Other diseases with a respiratory component that may be treated include, but are not limited to, Tuberculosis (TB), Influenza (flu), Respiratory syncytial virus infection (RSV), and lung cancer.

In addition to direct in vivo procedures, ex vivo procedures may be used in which cells are removed from a host, modified, and placed into the same or another host animal. It will be evident that one can utilize any of the compositions noted above for introduction of antigen-encoding nucleic acid molecules into tissue cells in an ex vivo context. Protocols for viral, physical and chemical methods of uptake are well known in the art.

In some aspects, the compositions of the present disclosure are useful for enhancing or eliciting, in a host, a patient or in cell culture, an immune response. As used herein, the term "subject" refers to any mammal. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

Use of Pharmaceutical and Therapeutic Thermostable Compositions

In another aspect, provided herein are methods for stimulating an immune response in a subject comprising administering a reconstituted spray dried vaccine composition described herein to the subject. The method may further comprise a step of reconstituting the thermostable spray dried vaccine composition into an oil-in-water emulsion before administration.

In another aspect, provided herein are methods for stimulating a therapeutic response in a subject comprising administering a reconstituted spray dried vaccine composition described herein to the subject. The method may further comprise a step of reconstituting the thermostable spray dried vaccine composition into an oil-in-water emulsion before administration. In some embodiments, the therapeutic response is for the treatment or prevention of allergy, cancer, infectious disease, autoimmunity, or addiction.

In another embodiment, provided herein are methods for stimulating an immune response in a subject comprising administering a spray dried vaccine or adjuvant powder via an inhalable method.

In another embodiment, provided herein are methods for stimulating an immune response in a subject comprising administering a spray dried vaccine or adjuvant powder via an inhalable method. In some embodiments, the therapeutic response is for the treatment or prevention of allergy, cancer, infectious disease, autoimmunity, or addiction.

In some embodiments, the present invention is useful for treating diseases with a respiratory component. In some embodiments, the respiratory component includes antigens associated with (or treatments for) Tuberculosis (TB), Influenza (flu), Respiratory syncytial virus infection (RSV), and lung cancer.

Accordingly, the present invention is useful for enhancing or eliciting, in a host, a patient or a subject, or in cell culture, an immune response. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

Routes of Administration

The present invention is directed to methods and compositions for vaccination, therapeutic treatment and prevention of conditions such as an infectious disease, cancer, or an autoimmune disease. The methods of the present invention comprise routes of administration that include parenteral and non-parenteral administration. Non-parenteral routes of administration include, but are not limited to, oral, buccal, sublingual, topical, transdermal, ophthalmic, otic, nasal, rectal, inhalation and vaginal routes. Injectable methods include, but are not limited to, parenteral routes of administration, intravenous, intramuscular, subcutaneous, intraperitoneal, intraspinal, intrathecal, intracerebroventricular, intraarterial and other routes of injection. These inventions contemplate compositions that can provide controlled, slow release, or sustained release of the antigen and/or adjuvant over a predetermined period of time.

In some embodiments, the composition for vaccination is a dry powder composition, and the administration comprises reconstituting the dry powder vaccine with an aqueous diluent prior to administration of the vaccine, and administering the reconstituted vaccine parenterally. In some embodiments, the adjuvant vaccine composition it reconstituted separately from the antigen composition and admixed prior to administration. In some embodiments, the reconstituted vaccine is administered immediately. In other embodiments, the dry powder vaccine is administered as a dry powder, for example via inhalation. In some embodiments, the method of inhalation comprises the use of an inhaler. In some embodiments, the inhaler is an active or passive dry powder inhaler or a pressurized metered dose inhaler. In some embodiments, the dry powder formulation is administered directly to the lungs.

Formulations

While embodiments of the formulations herein are dry powder formulations and/or reconstituted dry powder formulations, it is to be understood that this invention is not limited to the particular formulations, process steps, and materials disclosed herein as such formulations, process steps, and materials may vary somewhat.

Formulations are known to those skilled in the art and include but are not limited to formulations such as tablets, coated tablets, chewable tablets, effervescent tablets, pellets, capsules, syrups, suppositories, injectable formulations, and dispersion of the active agent in a medium that is insoluble in physiologic fluids or where the release of the antigen and/or adjuvant is released after degradation of the formulation due to mechanical, chemical or enzymatic activity.

Kits and Pharmaceutical Packs

Also contemplated in certain embodiments are kits comprising the herein described vaccine compositions, which may be provided in one or more containers. In one embodiment all components of the vaccine compositions are present together in a single container, but the invention embodiments are not intended to be so limited and also contemplate two or more containers.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Preferred examples of such containers include glass and/or plastic sealed or re-sealable tubes and ampules, including those having a rubber septum or other sealing means that is compatible with withdrawal of the contents using a needle and syringe.

Such containers may, for instance, be made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

The invention will be more fully understood by reference to the following examples. They should not, however, be construed as limiting the scope of the invention. It is understood that the examples and embodiments described herein are for illustrative purposes only. The various embodiments described above can be combined to provide further embodiments. Various modifications or changes in light thereof will become apparent to those skilled in the art from the foregoing description and are to be included within the spirit and purview of this application, and are to fall within the scope of the appended claims.

EXAMPLES

Conversion of liquid material, such as vaccines, into a dry powder reduces costs associated with refrigeration and transportation. Spray drying provides a unique solution as it allows for the powder to be engineered to have specific properties. For example, the use of spray drying as a dry powder processing method allows for engineering of the resulting powder to control properties such as flowability, size, and morphology. In Examples 1-4, spray drying was investigated as a method to encapsulate an adjuvanted tuberculosis vaccine, formulated as oil-in-water nanoemulsions within dry powder. Successful encapsulation of the adjuvanted vaccine within non-cohesive, amorphous microparticles was achieved in one iteration, with high retention rate of all components. Stability of the powder over 3 months at different temperatures showed that the powder was physically stable for all temperatures. Physiochemical analysis of the reconstituted powder showed antigen and agonist losses over time with increased temperature storage, though nano-emulsion size was maintained for all samples. This was a surprising result, because it was not known in the field that nanoemulsions of a substance that is liquid at room temperature could be converted into a gel-microparticle and reconstituted to the same droplet size without significant losses. In Example 4, the use of spray drying was investigated for inhalable routes of delivery.

The methods in Examples 1-4 used a spray-dried vaccine or adjuvant and characterized the dry powder, and the reconstituted vaccine formulation for stability and other important characteristics to determine the feasibility of a spray-dried formulation. The engineered particles should encapsulate the nano-emulsions within an amorphous microparticle for long term stability. Two formulations were spray dried and assessed for stability: the GLA-SE vehicle spray dried with trehalose and Tris buffer (SD-TG), and the GLA-SE vehicle with the ID93 protein spray dried with trehalose and Tris buffer (SD-TGI). The inhalable formulations may additionally include leucine.

ID93 was used because it is a recombinant protein composed of four *Mycobacterium tuberculosis* (Mtb) antigens to induce strong type T helper cell ($T_H1$) immune response as a vaccine to combat tuberculosis (TB) at all ages [3]. This antigen is combined with glucopyranosyl lipid A (GLA) squalene oil-in-water emulsion (SE), where GLA-SE is an adjuvant system formulated as a nanoemulsion [3]. The World Health Organization (WHO) has noted in the 2018 Global Tuberculosis Report that TB is the leading cause of death from a single infectious agent [4]. The only currently licensed TB vaccine to prevent infections of Mtb, baccille Calmette-Guerin (BCG) has been effectively implemented for children's immunization in 158 countries, but there is currently no vaccine that is effective in preventing TB in adults [4]. GLA-SE+ID93 vaccine dosage tests on mice, guinea pigs, and nonhuman primates showed induced $T_H1$ responses, as well as boosting BCG immunization [3]. The adjuvant component was used because it was shown in human clinical studies that vaccination with the GLA-SE+ID93 formulation elicited a higher antibody response than vaccination with ID93 alone [5].

Manufacture of a Dry Powder Vaccine by Spray Drying an Oil in Water Emulsion

The following formulations and methods were used to produce a dry powder spray dried vaccine and/or adjuvant composition.

TABLE 1

Formulation targets for the SD-TG and SD-TGI formulations

Design Targets
  Colloid concentration and integrity retained post-spray drying
  Stability maintained ≥3 months at 37° C.
    Squalene content loss ≤20%
    Emulsion size change ≤50%
    Polydispersity index <0.2
    GLA content loss ≤20%
    ID93 content loss ≤20%

The Formulation was produced using In-silico Modelling for Particle Design. Trehalose was used as an excipient. Trehalose is a disaccharide that is used as an excipient to stabilize biologics and was chosen to be the excipient used in this study. A relatively high solute concentration (100 mg/ml) of the excipient was utilized.

The design of stability for a maximum temperature was possible because the physical stability of amorphous materials is closely related to its molecular mobility, which is a function of storage temperature [13]. Storing at or below the Kauzmann temperature; that is, the temperature at which the molecular mobility is insignificant, will maximize physical stability. The Kauzmann temperature is approximately 50 K below $T_g$ [13]. Based on the formulation target of long term stability at 37° C., the $T_g$ of the spray dried powder must be >88° C. As described by the Gordon-Taylor equation [14], $T_g$ for sugar-water mixtures can be determined based on their mass fractions and an empirical parameter k. Chen et al. [15] modelled the trehalose-water glass transition curve by fitting literature data to the Gordon-Taylor equation, to determine a k of 5.2.

The moisture content of the final spray dried powder was engineered using the moisture sorption data of trehalose, which indicates that subjecting trehalose powder to outlet relative humidity of 10% will lead to an approximate 2-3% moisture content [16] [17]. Based on this trehalose-water plasticization curve [15] and the moisture sorption data [16] [17], the relative humidity at the dryer outlet and collection point must be <10% to ensure physical stability. Similarly, the outlet temperature must be significantly lower than the $T_g$ to prevent crystallization of the resulting powder. Based on these calculations, processing parameters were calculated such that the outlet temperature would be approximately 36° C. and the outlet relative humidity would be 7%. A relatively low drying gas temperature was chosen as well in order to prevent possible evaporation of the nanoemulsions during the spray drying process. It should be noted that these calculations were made based on data on powders generated from trehalose-water systems and the particles in this work will theoretically consist of ~17% GLA-SE emulsions.

The chemicals were formulated as follows: the GLA-SE vehicle in water and ID93 protein in water were formulated by IDRI (Seattle, WA, USA). Trehalose Dihydrate (Trehalose) and HPLC grade water were purchased from Fisher Scientific (Ottawa, ON, Canada). Tris(hydroxymethyl)aminomethane (Tris) and Hydrochloric acid (HCl) were purchased from Sigma Aldrich (Oakville, ON, Canada). A vial of the lead lyophilized vaccine candidate (TT) [8], was provided by IDRI (Seattle, WA, USA) for comparison.

Example 1

Feedstock Preparation

The Feedstock Preparation was as follows: ID93 (1.2 mg/ml ID93 protein) was stored in small aliquots at −80° C. prior to use. Similarly, a stock concentration of GLA-SE solution (10% [v/v] squalene, 50 μg/mL GLA) was stored in a refrigerator prior to use (see also [27] [28] for preparation of the stock GLA-SE). The feedstock was prepared by mixing 40 mM of Tris with 200 mg/ml of trehalose in HPLC water, then pH adjusting using hydrochloric acid to a pH of 7.5±1. Masses were measured using one of two balances (Model XS4002S; Mettler Toledo; Mississauga, ON, Canada), (Model ME204E; Mettler Toledo; Mississauga, ON, Canada), depending on the required mass of a given component. GLA-SE or GLASE+ID93 protein was diluted with HPLC grade water to 2× working concentration (4% [v/v] squalene, 20 μg/mL GLA; 8 μg/mL ID93) formulations SD-TG and SD-TGI, respectively. The two solutions were then mixed in a 1:1 ratio such that the final composition of the solution prior to spray drying was 100 mg/ml trehalose, 20 mM Tris, 2% [v/v]squalene, 10 μg/mL GLA for SD-TG, with additional 4 μg/mL ID93 protein for SD-TGI. The excipient composition target of SD-TG and SD-TGI was 20 mM Tris, 10% [w/v] trehalose.

Example 2

Spray Drying Process

Spray Drying was conducted using the Particle Engineering Group's custom research spray dryer [19]. The spray drying has the following components: twin fluid atomizer, drying chamber (30 L volume), cyclone separator, cutoff size less than 1 micrometer at 400 SLPM (standard liters per minute), double-walled collection vessel with thermostat system, peristaltic pump, process gas heater, gas source (compressed air), process control system, and process sensors and data acquisition system. The feedstock was atomized using a customized version of the Buchi B-191 twin fluid atomizer (Buchi Labortechnik, AG, Flawil, Switzerland), which has been characterized elsewhere [20]. Processing conditions were determined based on an in-silico model. The feedstock was supplied to the atomizer using a peristaltic pump (Model 77200-60; Cole-Parmer, Montreal, QC, Canada) at a rate of 0.6 ml/min to produce an air-liquid ratio of 8. The atomized droplets dried in air flowing at 200 SLPM, where the drying gas temperature was 65° C. Dry powder was separated from the air by a cyclone, and powder was collected in glass jars. These jars were sealed and stored in an environmental chamber (Model CEO 910W-4; Lunaire Limited, Williamsport, PA, USA) set to 25° C. and 7% RH until packaging (1-2 days). Laboratory PPE, including respirators, were worn during the spray drying process to minimize risks of inhaling the dry powder.

Example 3

Packaging and Storing

The spray dried formulation was packaged and stored using the following protocol: Packaging—To prevent moisture uptake in the powder during the stability study, an intensive packaging process was utilized. In general, proper packaging was used to preserve pharmaceutical powder integrity; otherwise, the powder may be subjected to moisture, thereby inactivating the biological components due to protein unraveling. The packages containing vials of powder was placed into temperature storage. Packaging preparation involved placing silica gel pouches into an environmental chamber (Model CEO 910W-4; Lunaire Limited, Williamsport, PA, USA) set to 25° C. and 7% RH for 3-4 days in order to equilibrate the desiccant to the outlet relative humidity of the spray dryer. At the same time, an equal number of silica gel pouches were equilibrated to 0% RH in a regulated glove box. A digital hygrometer (M170 Measurement Indicator with HMP77B humidity and temperature probe; Vaisala, Vantaa, Finland) was used to monitor the relative humidity of the environments.

The packaging process took place within a custom glovebox set to 0% RH. The powder was measured into low bind snap cap tubes (Product Z768820; Sigma Aldrich, Oakville, ON, Canada), which were then placed into an aluminum bag, along with a 7% RH desiccant pouch. This aluminum bag was then double heat-sealed, then placed into another aluminum bag, along with a 0% RH desiccant pouch. This external bag was also double heat-sealed. A simplified schematic summarizing process is shown in FIG. 1. The powder was stored as follows: The packages for low temperature stability (5° C.) were placed in a refrigerator (Model SCGP-1804; VWR, Edmonton, AB, Canada). The packages for 25° C. and 40° C. storage were placed in two separate incubators (Model 414005-120; VWR, Edmonton, AB, Canada). Regarding the former, while the incubator set point was 25° C., the temperature controller fluctuated between 25-28° C.

Example 4

Yield and Production Rate

Results for the yield and production rate of the powder are as follows: In-silico calculations predicted the nominal solids throughput to be 75 mg/min. Powder manufacturing for the stability study showed that the actual production rate to produce SD-TG and SD-TGI powders was 49 mg/min and 45 mg/min, respectively. A yield of 60% of theoretical is typical for small scale spray drying. However, the current formulation and processing parameters determined by in-silico modelling targeted maximizing encapsulation efficiency. In some embodiments, the larger agglomerates may be filtered out with the cyclone. In some embodiments, increased yield could be accomplished by addition of dispersability agents to the formulation.

Example 5

Characterization of the Spray Dried Dry Powder Vaccine Compositions

Preservation of emulsions and chemical integrity was studied to identify if the solutes were lost during the spray drying process. Formulation development and appropriate processing parameters were chosen to keep the process from significantly changing the emulsion size, either through evaporation of oil component, or aggregation of the emulsions. Thus, analysis was completed to compare the chemical and colloidal properties of the compounded liquid SD-TG and SD-TGI feedstock and the reconstituted powders as discussed in Example 1. These measured properties of the formulations before and after spray drying are shown in Table 2.

Methods such as scanning electron microscopy, Karl Fisher calorimetry, raman spectroscopy, HPLC, ELISA, SDS-PAGE, and pH and osmolality tests were used to characterize the dry powder and reconstituted powder as follows:

A. Dry Powder Characterization

The dry powder characterization used scanning electron microscopy and Raman spectroscopy as well as Karl Fischer calorimetry. In all cases, Results are reported as mean±standard deviation of replicate measurements. Number of replicates for each method are indicated. Two-tailed student's t-test was used for analysis, where statistically significant differences were reported for $p<0.05$.

For Scanning Electron Microscopy, powder samples were mounted directly onto aluminum SEM stubs (Product 16111; Ted Pella, Inc.; Redding, CA, USA) in such a way to intentionally produce cracked particles. These samples were placed in a desiccator connected to an in-house vacuum for 2-4 days to remove exposed nano-oil droplets to prevent damage to the imaging instrument. Following this process, the samples were sputtered with a coating of 80% gold and 20% palladium (Leica ACE600 Carbon/Metal Coater; Concord, ON, Canada) to a thickness of 10-15 nm. Images of the particles were taken with the Zeiss Sigma Field Emission Scanning Electron Microscope (Zeiss Sigma FE-SEM; Carl Zeiss, Oberkochen, Germany). Images ranging from magnifications of 500-20000× were taken at a working distance of 5.3-6.3 mm using an accelerating voltage of 3-4 kV.

Raman Spectroscopy used a custom dispersive Raman spectroscopy system was utilized to assess the solid state of the powders and obtain reference spectra. The system includes a 671 nm diode-pumped solid-state laser (Ventus Solo MPC6000; Laser Quantum, Stockport, UK) and a series of filters to optimize and clean the signal before it reaches the spectrograph. A detailed description of a sister apparatus, also developed by the Particle Engineering Group, and method of analysis can be found in other publications [22]. Components with low mass fractions (~1% of the sample) cannot be detected. Samples were placed into a closed sample chamber under nitrogen to prevent moisture exposure, as such all spectra were taken at a temperature of 22.0-23.0° C. and <5% RH. In addition to measured SD-TG and SD-TGI powder samples, Raman spectra analysis was also conducted on amorphous and crystalline trehalose powder samples as references. Similarly, references spectra were also obtained for liquid samples of squalene and 200 mg/ml Tris buffer in water, pH adjusted to pH 7.5.

Karl Fischer Calorimetry was used to measure the water content of the powder by mass was measured with a Karl Fisher Coulometric Titrator (Model C30; Mettler Toledo; Mississauga, ON, Canada), where results were displayed as a percentage based on the measured sample mass. The water in the sample is calculated by measuring the current required to react all the water in the sample. Samples were analyzed using a modified version of the default Stromboli coulometric method. For each set of tests, two "blank" vials were used to obtain a baseline of water content in the surroundings at the time of experimentation. Moisture content of the powder was determined by measuring and averaging two vials of the same powder. Analysis of experiments to determine moisture content of a HYDRANAL water standard (Honeywell; Mexico City, Mexico) showed that the machine variance is 0.3%.

B. Reconstituted Powder Characterization

The spray-dried powder was reconstituted as follows: Each of the previously 108 mg of powder massed and packaged vials were reconstituted with 0.8 ml of water upon the time of testing to yield concentrations similar to the liquid drug product. Each test was performed in triplicate on the reconstituted powder. Replicates of measurements on the feedstock were made from the same vial. The reconstituted powder was characterized by Dynamic Light Scattering, HPLC, ELISA, SDS-PAGE, pH, and Osmolality as follows: Dynamic light scattering was used to identify the mean hydrodynamic diameter of the emulsions, as well as their polydispersity using a Malvern Zetasizer APS (Malvern, UK). Liquid feedstock measurements were for 1 replicate analyzed 3 times. GLA and squalene quantification was accomplished with the use of reversed-phase HPLC analysis. These tests were conducted using a 1200 series HPLC device (Agilent Technologies) for separation, and Corona Charged Aerosol Detector (CAD) (ESA Biosciences, Chelmsford, MA, USA) for analyte detection. Liquid feedstock measurements were 2 replicates analyzed once. ELISA was used to identify the antigen content before and after spray drying by plating the sample and using certain antibodies to quantify ID93 content. Liquid feedstock measurements were 1 replicate analyzed 3 times. SDS-PAGE was used to measure the presence and the integrity of the ID93 protein in the sample based on the band presence or intensity, respectively. ID93 integrity was quantified by comparing band intensity to a stock control of ID93 protein. To find the pH, aliquots of 300 μL of reconstituted powder was measured using an Orion ROSS Ultra Semi-micro pH Electrode (Thermo scientific, Waltham, MA, USA) to determine sample pH. The pH meter was calibrated prior to each measurement using 4.00, 7.00, and 10.00 standards. Liquid feedstock measurements consisted of one replicate. Osmolality of the reconstituted powder was measured using an osmometer (Model 2020; Advanced instruments, Norwood, MA, USA). Liquid feedstock measurements consisted of one replicate.

Example 6

Stability Studies Spray Dried Dry Powder Vaccine Compositions

The formulations from Example 1 were studied for chemical, colloidal, and physical stability at a variety of temperatures. Many of the methods used for characterization were used to look at stability. Therefore, Example 2 provides the methods used for the stability studies. Stability is important because emulsion instability can cause deactivation of the adjuvant (the TLR4 agonist, such as GLA) and decreased concentration, thereby decreasing the immune response generated by the adjuvant system. Additionally, emulsion instability may also possibly lead to the emulsions forming larger droplets [6]. Because larger particles will be cleared from the body more quickly, this can also reduce the immune response. Furthermore, emulsions that are larger than 4 μm can cause changes in blood pressure and increase the possibility of embolisms [7]. The GLA-SE adjuvant is stable as a refrigerated liquid, therefore, the current adjuvanted ID93 vaccine candidate is administered in clinical studies in a two vial system consisting of rehydrated lyophilized ID93 and the liquid adjuvant, which are mixed prior to administration [8].

Example 7

Chemical and Colloidal Stability

Stability of the spray-dried powder was assessed based on preset criteria discussed in Table 1. Stability at 3 months at a higher temperature, such as 37° C., indicated long term stability at room temperature.

TABLE 2

Chemical and colloidal properties before and after spray drying for formulations.

| | ID | Squalene Content (mg/mL) | Emulsion Diameter (nm) | Polydispersity Index | GLA Content (μg/ml) | ID93 Content (μg/ml) | pH | Osmolality (mOsmol/kg) |
|---|---|---|---|---|---|---|---|---|
| | Target | 17.2 | 92 | 0.06 | 10 | 4 | 7.5 | ~300 |
| SD-TG | Feedstock Liquid | 19.1 ± 0.4 | 95.3 ± 0.9 | 0.05 ± 0.04 | 9.2 ± 0.5 | N/A | 7.62 | 383 |
| | Reconstituted Powder | 18.8 ± 0.3 | 96.9 ± 0.2 | 0.07 ± 0.02 | 9.5 ± 0.4 | N/A | 7.57 ± 0.04 | 376 ± 8 |

TABLE 2-continued

Chemical and colloidal properties before and after spray drying for formulations.

| ID | | Squalene Content (mg/mL) | Emulsion Diameter (nm) | Polydispersity Index | GLA Content (µg/ml) | ID93 Content (µg/ml) | pH | Osmolality (mOsmol/kg) |
|---|---|---|---|---|---|---|---|---|
| SD-TGI | Feedstock Liquid | 18.8 ± 0.3 | 94.9 ± 0.8 | 0.06 ± 0.01 | 9.3 ± 0.4 | 1.17 ± 0.02 | 7.56 | 389 |
| | Reconstituted Powder | 17.3 ± 0.6 | 97.6 ± 1.1 | 0.09 ± 0.01 | 9.0 ± 0.4 | 2.0 ± 0.1 | 7.55 ± 0.01 | 351 ± 8 |

Abbreviations: SD-TG, spray dried trehalose+Tris+GLA-SE; SD-TGI, spray dried trehalose+Tris+GLA-SE+ID93.

In the results shown in Table 2, comparison of the feedstock liquid and the reconstituted powder indicated a high encapsulation efficiency. The results show high retention (>90%) of the squalene component for both formulations. Surprisingly the droplet size of the reconstituted emulsion was nearly identical to the emulsion in the feedstock and the content was nearly unchanged. This means that is it possible to spray dry these nanoemulsions without breaking them or losing the oil (which is liquid). While, it has been shown that smaller emulsions are more stable over time than large ones [6], the success shown with this nanoemulsion has not been seen. Further, the polydispersity index, GLA content, and pH did not change significantly ($p>0.05$) over the course of spray drying for both formulations, indicating that the number of emulsions that conglomerate is low. The retention of GLA and ID93 content indicated that these components did not degrade over the course of spray drying, which was particularly successful, as these components are sensitive to thermal stress. The low ID93 content in the SD-TGI powder may have been due to the protein binding to the sides of the feedstock container during compounding.

Though immediate analysis after spray drying showed high retention rates (see Example 2), stability of the powder over time was also investigated because applicability of the spray dried emulsion as a vaccine is dependent on the nano-emulsion stability over time. Mlalila et. al's [24] experiments of spray drying lipid nanoparticles initially showed similar diameter scale as GLA-SE; however, after one month of storage in a dessicator the nanoparticle sizes increased by a factor of 2-8. The stability study involved storage of the spray-dried powders at several storage temperatures: −20, 2-8, 25 and 40° C. For each temperature, at a given timepoint the powders were reconstituted and assessed for squalene content, emulsion diameter, polydispersity index, GLA concentration, ID93 concentration, and pH. Osmolality was measured initially and after 3 months for all storage temperatures.

Figure 2:
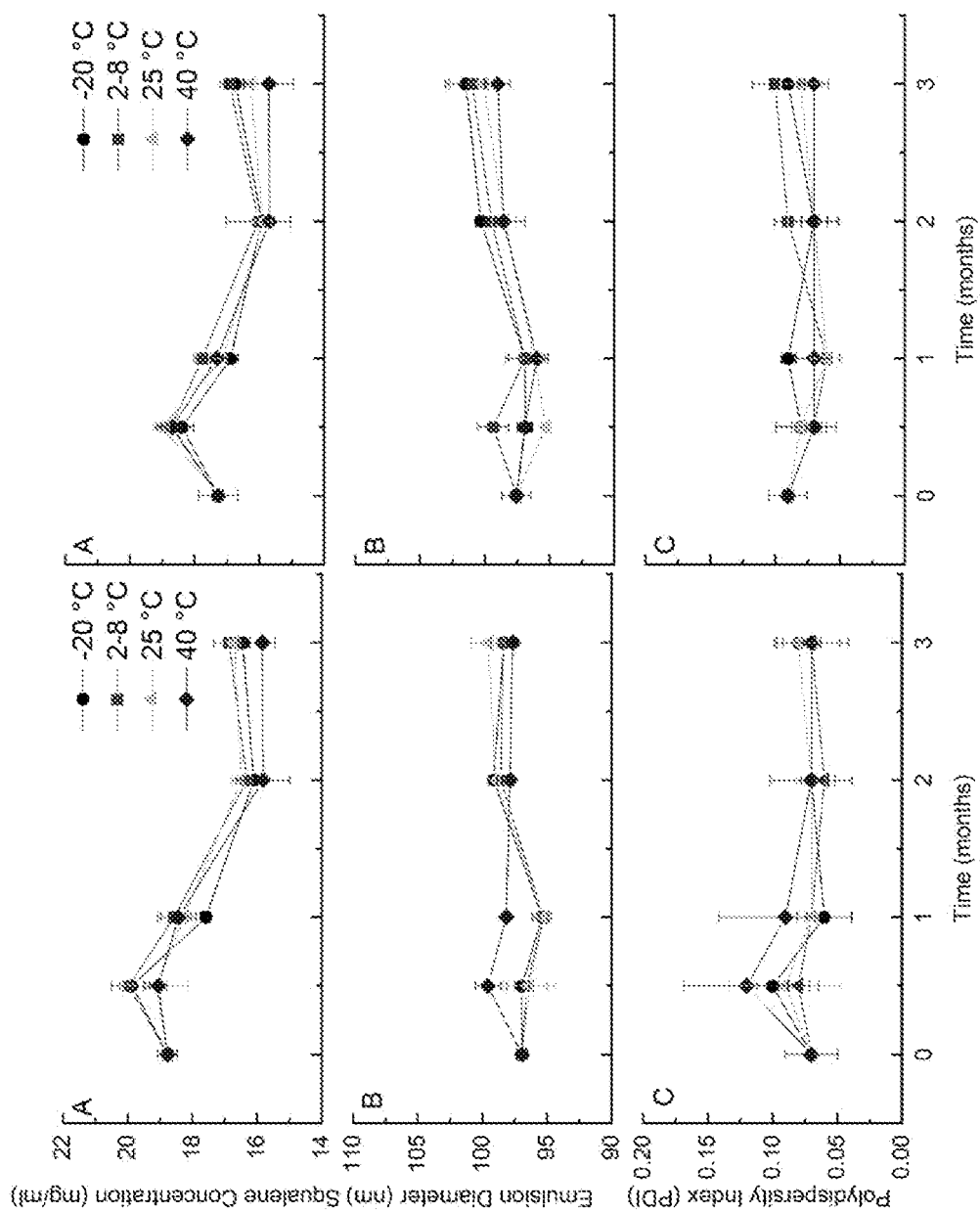
FIG. 2 shows plots showing A) squalene concentration, B) nano-emulsion diameter size and C) polydispersity index of nano-emulsions for the reconstituted SD-TG powder (left) and reconstituted SD-TGI powder (right) stored over 3 months at the indicated temperatures. Legend indicates the storage temperatures for the powder. Error bars indicate the standard deviation of three measurements. Abbreviations: SD-TG, spray dried trehalose+Tris+GLA-SE; SD-TGI, spray dried trehalose+Tris+GLA-SE+ID93; GLA, glucopyranosyl lipid adjuvant; SE, squalene oil-in-water emulsion.

Properties of the squalene component of the GLA-SE vehicle over three months of the stability study are shown in FIG. 2. Squalene content decreased for both powder formulations at all storage temperatures. After 3 months of storage at 40° C., squalene content for SD-TG was reduced from 18.8±0.3 mg/ml to 15.8±0.4 mg/ml (16% loss) and for SD-TGI was reduced from 17.3±0.6 mg/ml to 15.7±0.8 mg/ml (9% loss). Emulsion diameter remained essentially unchanged from 96.9±0.2 nm to 97.7±0.5 nm (only a 1% increase) and from 97.6±1.1 nm to 99±0.9 nm for SD-TG and SD-TGI, respectively. PDI did not change significantly over the course of 3 months at any given storage temperature ($p>0.05$). As such, these changes are all within the aforementioned stability criteria for squalene; that is, <20% loss of squalene; <50% change in emulsion size; and polydispersity index <0.2. As compared to 3-month stability studies at 37° C. conducted on lead lyophilized candidates, the spray-dried powders had a comparable performance regarding particle size change [8]. Additionally, the spray-dried candidates performed significantly better than the current two-vial clinical presentation, liquid single vial, and the proof-of-concept (POC) lyophilized candidate, the latter of which undergoes a particle size change of 84% [8]. GLA retention was high for storage at −20 and 2-8° C. after 3 months for both powders (87-93% retained). However, after 3 months of storage at 25° C., the GLA content was reduced from 9.5±0.4 µg/ml to 8.7±0.2 µg/ml (12% loss) for the SD-TG formulation, and from 9.0±0.4 µg/ml to 7.2±0.1 µg/ml (19% loss) for the SD-TGI formulation. Similarly, at 40° C. the GLA content was reduced to 5.8±0.2 µg/ml (40% loss) for the SD-TG formulation, and to 5.1±0.3 µg/ml (43% loss) for the SD-TGI formulation.

The SDS-PAGE results confirmed that the ID93 was present at all storage temperatures. Analysis with imaging software compared the ID93+GLA-SE control to quantify the remaining ID93 protein in terms of percentage of control. Using this analysis, it was found that after storage at 3 months, the amount of ID93 protein in the SD-TGI formulation was 83±19% at −20° C., 66.5±11% at 2-8° C., 40±5% at 25° C., and 44±3% at 40° C.

Overall, the pH of the reconstituted liquid trended downward over time for all temperatures. However, the pH remained between 7.41 and 7.61 for reconstituted SD-TG and SD-TGI. The greatest change was 0.16 pH units; comparatively, liquid, two-vial and POC samples stored at 37° C. for 3 months showed greater pH decreases of 0.2-0.8 pH units [8]. Alternatively, osmolality slightly increased over time for all samples. For the SD-TG sample, osmolality increased 2-4%, with the lowest change occurring at 40° C. with the largest change occurring at −20° C. storage. Osmolality increased between 3-9% for the reconstituted SD-TGI powder, with the lowest change occurring at 40° C. and the largest change occurring at 2-8° C. storage.

Though the spray-dried formulations experienced some losses in GLA and ID93 protein outside the formulation targets, the dry powder characterization results demonstrated that the particles remained physically stable at all temperatures.

B. Physical Stability

Particle morphology analysis of the SEM images indicated that spray drying the formulation produced a polydisperse sample where the microparticles ranged in geometric diameter from ~1-20 µm. The SEM images for SD-TG and SD-TGI, shown in FIGS. 3a and 3b, respectively, showed the spray dried microparticles appeared to be spherical, non-cohesive, with a surface that ranged from smooth to slightly dimpled. Additionally, the similarity of these microparticles showed that the presence of the protein did not affect the particle structure. Microparticles of 100 mg/mL trehalose spray-dried under the same conditions, shown in FIG. 3c for comparison had a very similar outer particle morphology as the SD-TG and SD-TGI formulation, that is, spherical non-cohesive particles, with smooth or slightly dimpled surfaces. The SD-TG and SD-TGI particles also were slightly larger than the trehalose particles; however, this is to be expected to due to the increased solids content of the SD-TG and SD-TGI formulations.

Figure 3:
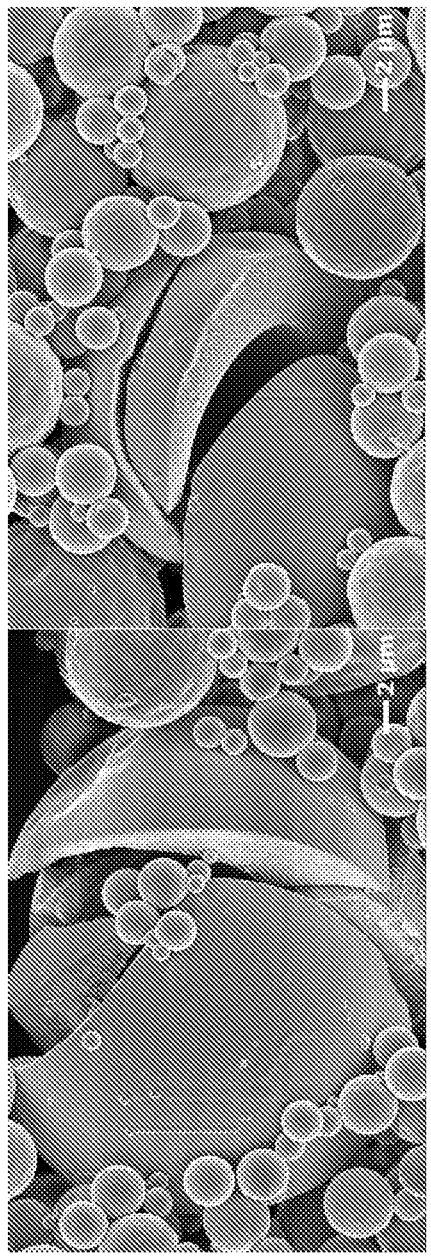
FIG. 3 shows SEM images of a) SD-TG microparticles, b) SD-TGI microparticles c) 100 mg/ml spray dried trehalose, d) lyophilized TT (the lyophilized leading candidate). Scales are provided on the respective images. Abbreviations: SD-TG, spray dried trehalose+Tris+GLA-SE; SD-TGI, spray dried trehalose+Tris+GLA-SE+ID93; GLA, glucopyranosyl lipid adjuvant; SE, squalene oil-in-water emulsion.
Figure 3:
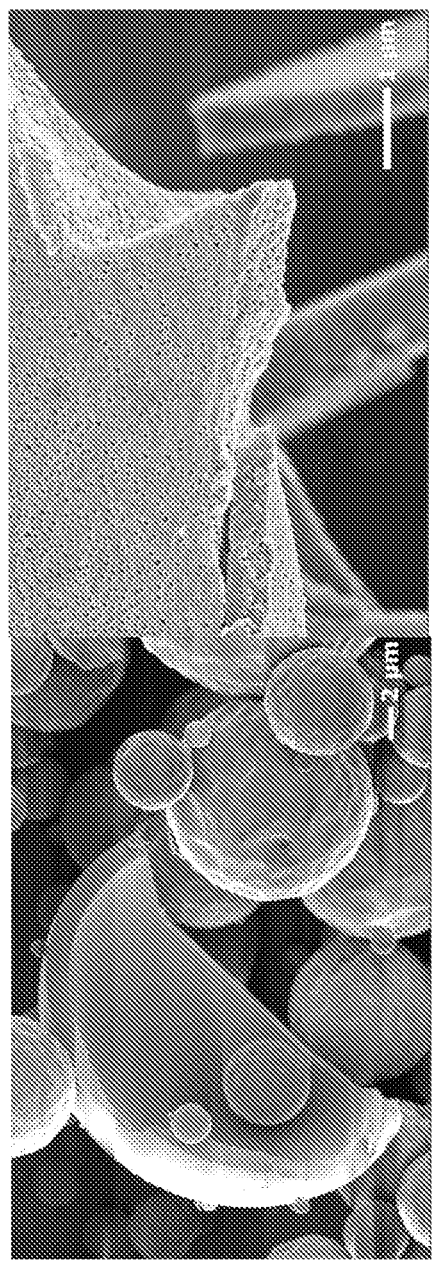
Figure 4:
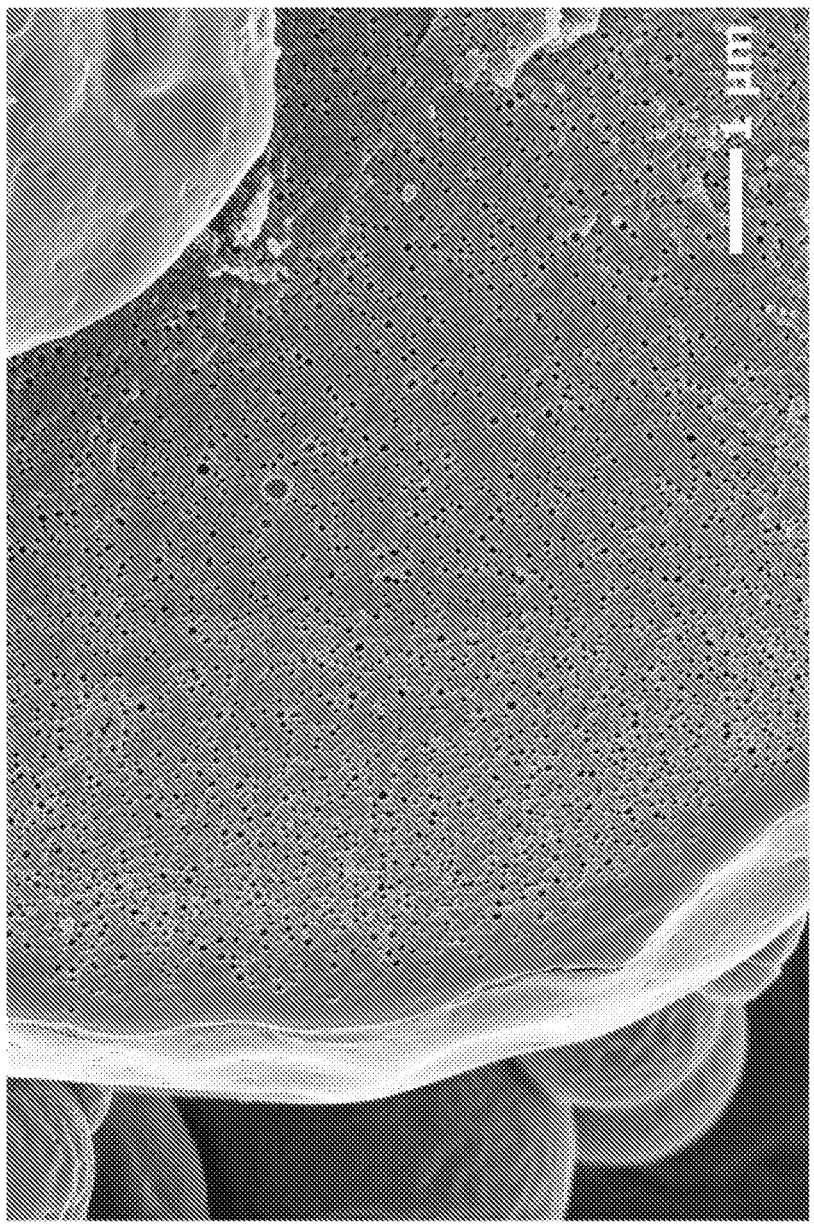
FIG. 4 shows an SEM image of cracked SD-TG microparticle to show interior morphology. Scales are provided on the respective images. Abbreviations: SD-TG, spray dried trehalose+Tris+GLA-SE; GLA, glucopyranosyl lipid adjuvant; SE, squalene oil-in-water emulsion.

SEM images of the cracked microparticles of SD-TG, SD-TGI and trehalose all showed that these particles could be hollow or solid, such that there was a range of shell thicknesses within a given sample. However, the interior structure of this shell differed from spray-dried trehalose. While trehalose particles showed a solid shell, the interior of the SD-TG and SD-TGI particle had numerous voids within a trehalose structure. These voids shown in the SEM images of SD-TG and SD-TGI also appeared in images of the lyophilized TT formulation (FIG. 3d). Given that the size of these voids also appeared to be approximately the nano-emulsion size, the voids were likely left behind by the evaporated nano-emulsion. Higher magnification images of the surface showed comparatively few voids on the surface of the particle, indicating that some, but not a significant amount, of the nano-emulsion was lost due to accumulation on the outer surface of the particle.

Figure 5:
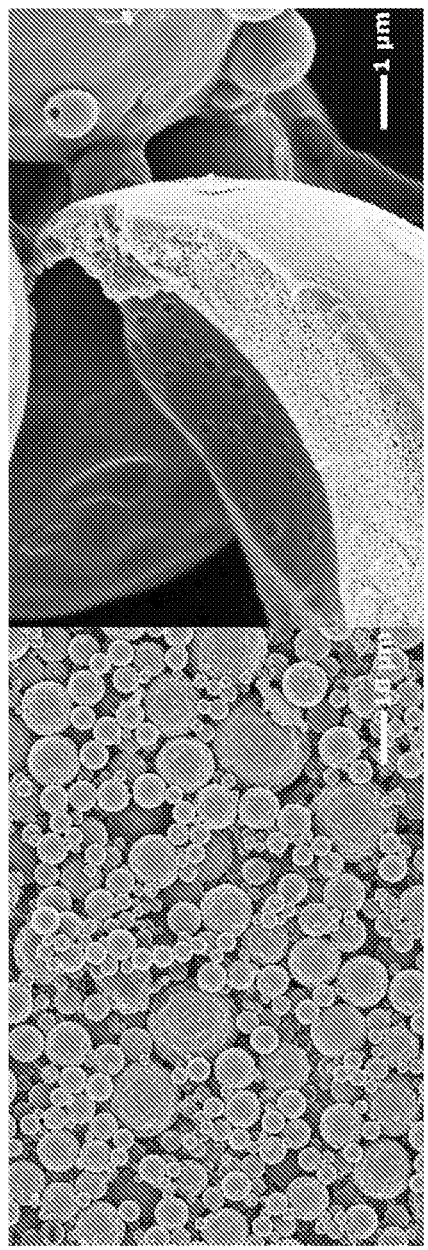
FIG. 5 shows SEM images of SD-TGI powder after 3 months of storage at 40° C. indicating a) sample maintains external morphology after accelerated storage, b) interior particle structure is maintained. Scales are provided on the respective images. Abbreviations: SD-TGI, spray dried trehalose+Tris+GLA-SE+ID93; GLA, glucopyranosyl lipid adjuvant; SE, squalene oil-in-water emulsion.

FIG. 5 shows the SD-TGI formulation after 3 months storage at different storage temperatures. A lower magnification view in.

FIG. 5a, shows that the sample stored at 40° C. maintained its exterior particle structure. The microparticles were still polydisperse, spherical and non-cohesive. The lack of particle fusing and shape change indicated physical stability. As shown in FIG. 5b, the interior structure of the particle was also maintained after storage at 40° C., because the voids left by the nano-emulsions were clearly distinct. The slight rounding of the outer features shown at high magnifications suggest that the powder mobility is not insignificant. The GLA-SE component likely lowered powder $T_g$ to below the predicted ~90° C.

The powder moisture content was identified as follows: The initial moisture content of the powder by wet basis was measured to be 2.6±0.1%. The moisture content after 3 months of storage at 5, 25, and 40° C. was, respectively, 2.7%, 2.4%, 2.1%; all values ±0.1%; these changes were determined to be statistically insignificant (p>0.05). The slight powder drying at higher temperatures is not unexpected, due to the elevated temperatures and the relatively large amount of headspace in the vial used for Karl Fischer experiments. It was notable that the 5° C. sample, which was stored in a refrigerator with an internal environment of >30% RH, did not display moisture uptake. This lack of moisture uptake was particularly interesting and signified that the packaging system implemented was very robust. As noted previously, protein degradation in spray-dried powders is linked to crystallization of these powders; therefore, protein degradation may be mitigated by preventing moisture uptake of these powders by preventing any lowering of the powder's $T_g$.

Solid State Analysis involved looking at the Raman spectra analysis on SD-TG and SD-TGI powders at various timepoints within the stability study in order to confirm the presence of components within the sample and to determine any changes in solid state. Sample spectra for SD-TG powder obtained at timepoint 0, as well as reference spectra for amorphous trehalose, squalene, Tris pH 7.5, and crystalline trehalose are shown FIG. 7. The ID93 protein component contribution was not included in the analysis, because its low mass fraction (~0.003%) was not within the Raman system's detection limit. Reference spectra were also obtained for other components of GLA-SE; however, their mass fraction in the sample was also outside of the detection limit.

Figure 6:
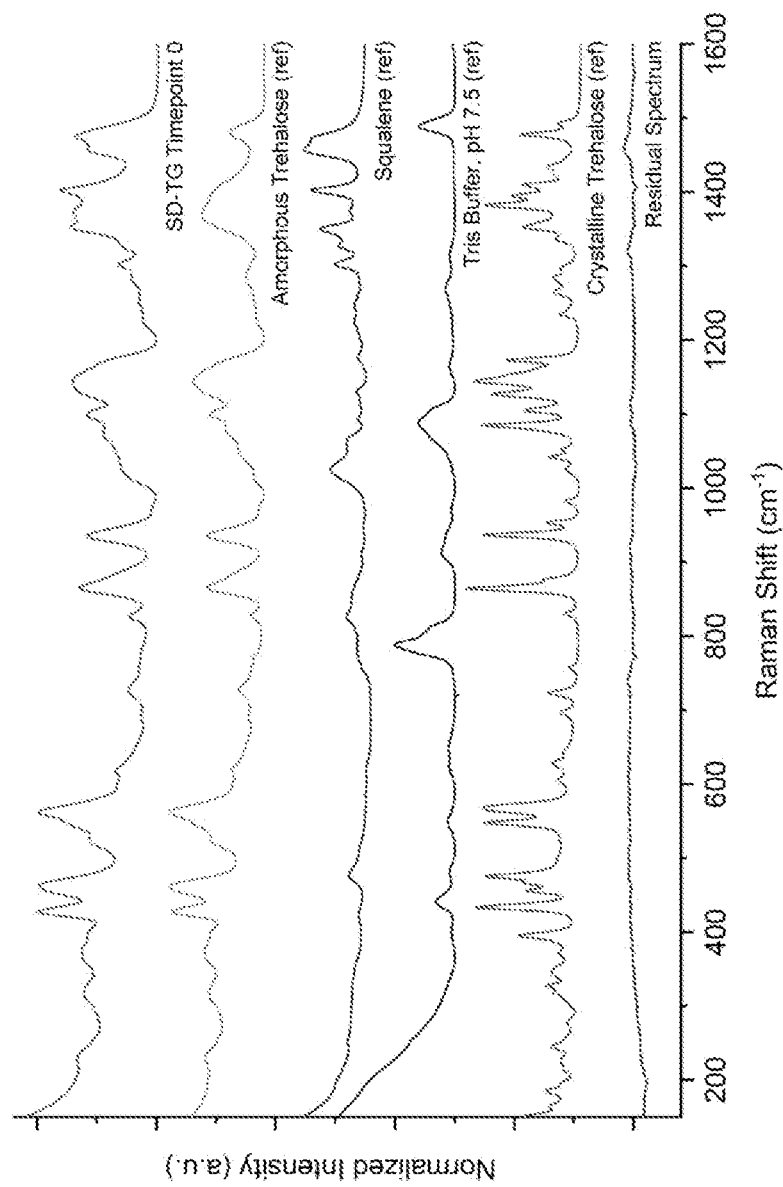
FIGS. 6a and b show SEM images of SD-TGI powder after 3 months of storage at 40° C. indicating a) sample maintains external morphology after accelerated storage, b) interior particle structure is maintained. Scales are provided on the respective images. Abbreviations: SD-TGI, spray dried trehalose+Tris+GLA-SE+ID93; GLA, glucopyranosyl lipid adjuvant; SE, squalene oil-in-water emulsion
Figure 7:
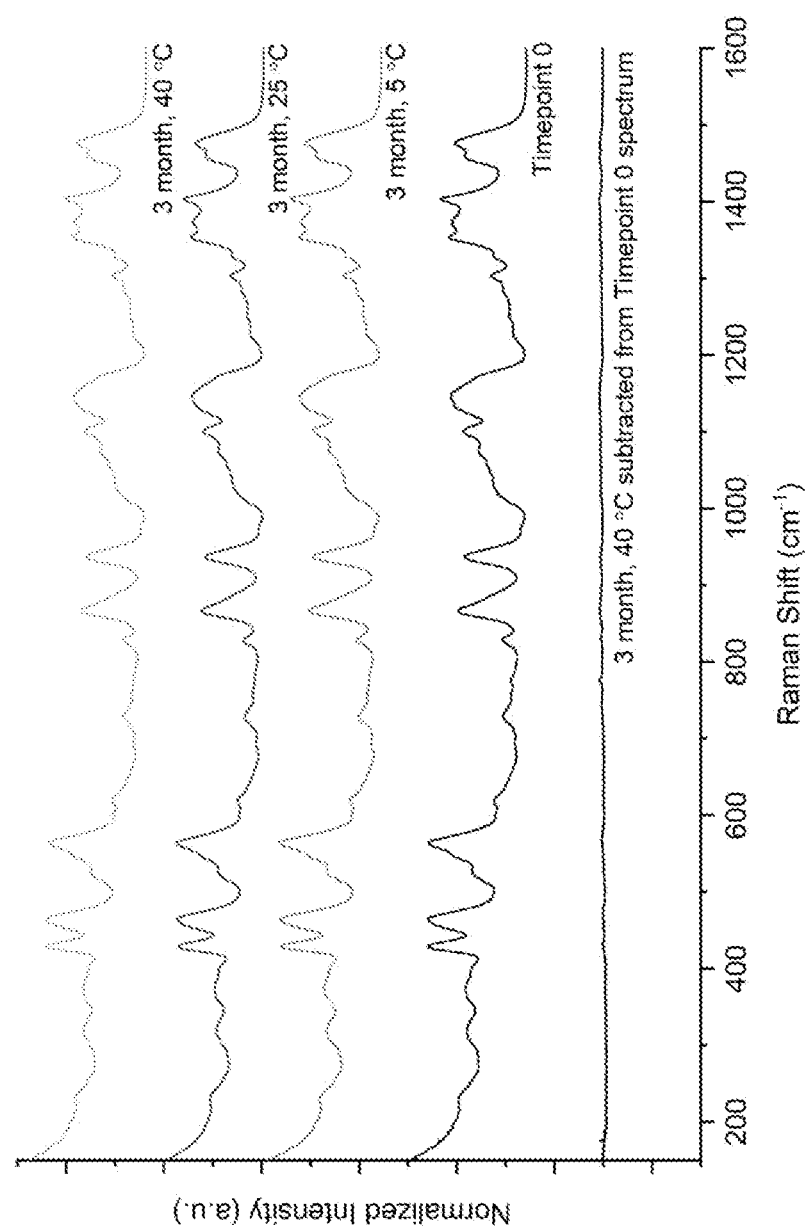
FIG. 7 shows a normalized Raman spectrum of the SD-TG powder sample, and reference spectra of amorphous trehalose, squalene, 1 M Tris Buffer at 7.5 pH, and crystalline trehalose. Also shown is the normalized residual spectrum, obtained by subtracting individual component contributions from the raw measured SD-TG spectrum. Abbreviations: SD-TGI, spray dried trehalose+Tris+GLA-SE+ID93; GLA, glucopyranosyl lipid adjuvant; SE, squalene oil-in-water emulsion.

Inspection of the sample spectra showed that the trehalose component was completely amorphous. This was evident by the presence of amorphous trehalose characteristic peaks at 425, 460, 560, 865, 935, and 1145 cm$^{-1}$ in the sample and further supported by the lack of crystalline trehalose characteristic peaks at approximately 395, 455, 695, 980, and 1235 cm$^{-1}$, to name a few. The squalene presence in the sample was identified by its characteristic peak appearing at 1400 cm$^{-1}$. The solid state of trehalose was further confirmed by the low normalized intensity of the residual spectrum, shown in FIGS. 6a and b show SEM images of SD-TGI powder after 3 months of storage at 40° C. indicating a) sample maintains external morphology after accelerated storage, b) interior particle structure is maintained. Scales are provided on the respective images. Abbreviations: SD-TGI, spray dried trehalose+Tris+GLA-SE+ID93; GLA, glucopyranosyl lipid adjuvant; SE, squalene oil-in-water emulsion. In FIG. 7 the residual spectrum was obtained by subtracting the reference spectra for amorphous trehalose (mass fraction 81%), squalene (mass fraction 14%) and Tris (mass fraction 2%) from the sample spectrum. The DMPC (mass fraction 3%) reference spectrum could not be obtained; however, the presence of peaks at 1325 and 1460 cm$^{-1}$ [25] in the residual spectrum was likely due to this component of the GLA-SE vehicle.

Similar analysis was completed on the SD-TGI powder, also confirming that the trehalose component was amorphous, as well as the presence of squalene and Tris buffer in the sample. It was expected that SD-TG and SD-TGI would have similar results, as the only difference in formulation between the samples is the presence of ID93 in the latter.

Figure 8:
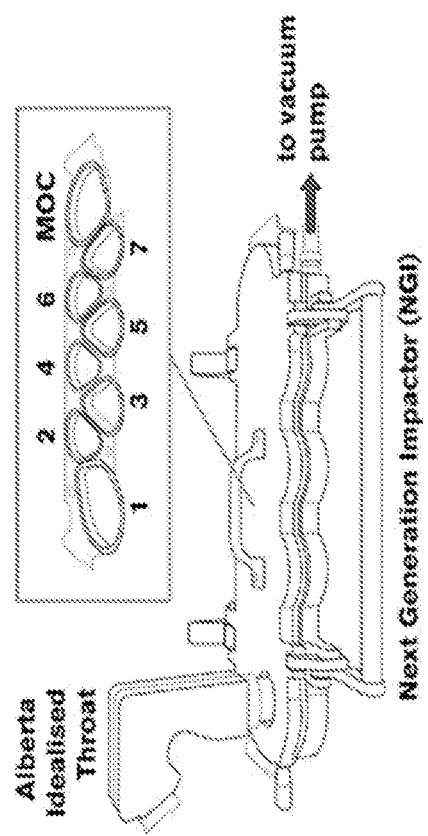
FIG. 8 shows normalized Raman spectra of the SD-TGI powder formulation, shown after 3 months of storage at 5, 25, and 40° C., and at timepoint 0. All samples shown were normalized according to the peak at 460 $cm^{-1}$. Also shown is residual spectrum obtained from subtracting the 3 month, 40° C. spectrum from the spectrum obtained at timepoint 0. The essentially straight remaining spectrum indicates that the SD-TGI powder stored for 3 months at 40° C. does not have a significantly different solid phase than it did at the beginning of the stability study.

Sample spectra for SD-TGI at timepoint 0 and after 3 months of storage at 5, 25, and 40° C. are shown in FIG. 8. All spectra looked very similar, indicating that the solid state of the powder was not changed significantly over the course of the stability study. Indeed, deconvolution of the SD-TG and SD-TGI spectra collected at different points of the stability study confirmed that all samples showed the presence of squalene and Tris, and that trehalose remained amorphous. This fits with the moisture content data, because if moisture content did not rise, it was unlikely that the trehalose would crystallize because the engineered $T_g$ was >88° C. The remaining spectrum after subtracting the SD-TGI spectrum collected after 3 months at 40° C. sample from timepoint 0 spectrum (FIG. 8) showed that the extremely low normalized remainder spectrum indicated that the two samples were remarkably similar and therefore the solid phase of the powder was maintained over this period, even with the added thermal stress placed on the powder.

Spray dried oil-in-water formulations with trehalose as an excipient were evaluated for stability to evaluate the feasibility of encapsulation of nano-emulsions within an amorphous microparticle for long-term storage. Two formulations of an adjuvanted tuberculosis vaccine were tested for stability: a composition of the adjuvant system—formulated as an oil-in-water emulsion, and a composition combining the adjuvant system and the vaccine protein. In-silico modelling was used in conjunction with known trehalose data in order to predict processing conditions with increased likelihood of success, thus reducing the required amount of trial-error empirical work. Comparison of the formulation feedstock and the reconstituted spray dried powder showed that the emulsion integrity was preserved, in both size and concentration. As well, the adjuvant and the protein were shown to have a similar concentration post-spraying. These results strongly suggest that the efficacy of the vaccine was preserved over spray drying due to the exhibited preservation of physiochemical properties upon reconstitution.

These spray-dried powders were then assessed for stability over three months, up to a temperature of 40° C., through characterization of the reconstituted powder and the dry powder itself. The results showed that the powders maintained physical stability for all temperatures after 3 months. Similarly, the emulsion size and polydispersity did not change significantly at all temperatures for both formulations, performing significantly better than a lyophilized proof-of-concept and on par with lead lyophilized candidates in these tests [8]. GLA preservation was on par with the proof-of-concept version [8].

The demonstrated potential of the product shows that it is particularly useful for applications where long-term stability at room temperature is needed, such as in global health applications. Formulating adjuvants with or without antigen as a dry powder and reconstituting immediately prior to administration will significantly reduce costs associated with transport and storage. Further, spray drying is a viable alternative over lyophilization because it has a lower processing cost [10].

Example 8

Spray Dried Formulations for Pulmonary Delivery

After demonstrating the potential of spray drying for vaccine compositions in Examples 1-8, experiments were performed to refine the formulation to generate particle sizes suitable for pulmonary delivery (inhalation). Spray drying, unlike lyophilization, allows for engineering of properties such as particle size. This opens the door to other delivery routes, such as pulmonary (inhalation), rather than intramuscular injections.

Inhalable particles need certain characteristics for successful administration including, 1. An aerodynamic particle size of less than 20 μm, including 2-3 μm, which can be obtainable by lowering the solids content and manipulating the spray drying parameters, and 2. High dispersibility to create particles that are rugose and hollow. This can be obtained by introducing L-leucine as an excipient such that the concentration is greater than 0.25 mass fraction.

The following formulations were made for spray dried ID93 and GLA adjuvant. Initially, the antigen ID93 was not included in the inhalable formulations (LN-23-32 and LN-23-33) because it was difficult to pH small volumes. The Trehalose and GLA-SE concentrations were prepared at ⅓ of those used for lyophilized and spray dried TT (see LN-23-17 in Table 3 below). LN-23-33 was formulated with leucine as a shell former.

TABLE 3

Formulations for injectable spray dried ID93 compared to inhalable formulations with and without leucine.

| Total Solid and Emulsion Content Component | Batch ID: LN-23-17 (Spray dried injectable for comparison) 124 mg/ml | | Batch ID: LN-23-32 40.5 mg/ml | | Batch ID: LN-23-33 (with Leucine) 50.5 mg/ml | |
|---|---|---|---|---|---|---|
| | Concentration in Solution | Mass Fraction in Powder (%) | Concentration in Solution | Mass Fraction in Powder (%) | Concentration in Solution | Mass Fraction in Powder (%) |
| ID93 | 4 μg/mL | 0.003% | 0 μg/mL | — | 0 μg/mL | — |
| Trehalose | 100 mg/mL | 81% | 33.3 mg/mL | 82% | 33.3 mg/mL | 66% |
| Tris (buffer) | 2.4 mg/mL [20 mM] | 2% | 0 mg/mL | — | 0 mg/mL | — |
| GMP grade Squalene | 17.2 mg/mL | 14% | 5.73 mg/mL | 14% | 5.73 mg/mL | 11% |
| DMPC | | 3% | 1.27 mg/mL | 3% | 1.27 mg/mL | 3% |
| GLA | 10 μg/mL | 0.01% | 3.3 μg/mL | 0.01% | 3.3 μg/mL | 0.01% |
| Leucine | 0 mg/mL | — | 0 mg/mL | — | 10 mg/mL | 19.8% |
| Feed volume (mL) | 238 | | 49 | | 28 | |
| Mass if 100% recovered (g) | 29.5 | | 1.98 | | 1.41 | |
| Actual mass recovered (g) | 17.3 | | 0.64 | | 0.89 | |
| % Yield | 59% | | 32% | | 63% | |

Table 4 provides preliminary particle size results using a dry powder inhaler in the form of an Alberta Idealized throat (Next Generator Impactor) as show in FIG. 8. The following were analyzed: (1). Emitted Dose from Inhaler (%), (2) Total Lung Deposition (TLD) (%) indicates losses to mouth-throat), (3). Mass Median Aerodynamic Diameter, MMAD (μm), (4). Geometric Standard Deviation, GSD. The MMAD looks at the diameter of the dry particles. The two inhalable formulations were tested: LN-23-32 and LN-23-33 (with leucine).

The results in Table 3 compared the concentration of the components from three formulations before and after spray drying. The two inhalable formulations (LN-23-32 and LN-23-33) were compared to the dried injectable formulation LN-23-17. The results in Table 3 showed that the leucine increased the yield, based on the mass of the components that were recovered after spray drying.

TABLE 4a and b

Preliminary particle size results for (a) LN-23-32 and (b) LN-23-33

(a) LN-23-32

| n | 1 | 2 | 3 | Average | STD |
|---|---|---|---|---------|-----|
| Emitted Dose (%) | 72% | 93% | 96% | 87% | 13% |
| TLD | 21% | 22% | 19% | 20% | 2% |
| MMAD (um) | 3.0 | 3.4 | 3.3 | 3.2 | 0.2 |
| GSD | 1.8 | 1.6 | 1.6 | 1.7 | 0.1 |

(b) LN-23-33 (with Leucine)

| n | 1 | 2 | 3 | Average | STD |
|---|---|---|---|---------|-----|
| Emitted Dose (%) | 97% | 93% | 100% | 97% | 3% |
| TLD | 33% | 22% | 41% | 32% | 10% |
| MMAD | 3.6 | 3.4 | 3.6 | 3.5 | 0.1 |
| GSD | 1.8 | 1.6 | 2.2 | 1.9 | 0.3 | vaccine compositions therein. For example, to find the pH, aliquots of 300 μL of reconstituted powder were measured using an Orion ROSS Ultra Semi-micro pH Electrode (Thermo scientific, Waltham, MA, USA) to determine sample pH. The pH meter was calibrated prior to each measurement using 4.00, 7.00, and 10.00 standards. Liquid feedstock measurements consisted of one replicate. Osmolality of the reconstituted powder was measured using an osmometer (Model 2020; Advanced instruments, Norwood, MA, USA). Liquid feedstock measurements consisted of one replicate. SD represents the standard deviation. The particle size was determined by measuring the Z-average diameter (Z-Aved) of the liquid dry powder composition (see Zavg in Table 5). GLA and squalene quantification was accomplished using reversed-phase HPLC analysis. The tests were conducted using a 1200 series HPLC device for separation, and Corona Charged Aerosol Detector (CAD) for analyte detection. Liquid feedstock measurement were 2 replicates analyzed once. The polydispersity index (PdI) is evaluated following reconstitution of the spray dried composition. For example, dynamic light scattering (DLS) can be used to evaluate the PdI.

Table 5 shows the results of the tests of the inhalable formulations as compared to injectable. The results show high retention of the squalene and the GLA (low % loss) indicating that these components did not degrade over the course of spray drying and the particle diameter (the Zavg) was preserved. The polydispersity index (PdI) did not change significantly suggesting that the conglomeration of the emulsions was low.

TABLE 5

Results of test for injectable formulations for spray dried ID93 compared to inhalable formulations

| Sample ID | Description | pH* | Zavg (nm) | SD (nm) | PdI | GLA (ug/mL) | SD | Squalene (mg/mL) | SD | Osmolality (mOsmol/kg) |
|---|---|---|---|---|---|---|---|---|---|---|
| Target | | N/A | ~90 | | <0.2 | 3.33 | | 5.72 | | |
| LN-23-32 | Pre-spray dried liquid (no ID93, no Tris) | 7.5 | 92 | 1 | 0.05 | 3.51 | 0.08 | 5.46 | 0.04 | 105 |
| | Spray dried GLA-SE with 3.3% Trehalose (no ID93, no Tris, 1/3 [GLA-SE]) INHALABLE | 7.7 | 92 | 2 | 0.05 | 3.39 | 0.04 | 5.36 | 0.02 | 109 |
| % loss | | -2.4% | 0.3% | | -3.9% | 3.4% | | 1.8% | | -3.8% |
| LN-23-33 | Pre-spray dried liquid (no ID93, no Tris) | 6.9 | 92 | 2 | 0.04 | 4.4 | 0.6 | 5.76 | 0.07 | 183 |
| | Spray dried GLA-SE with 3.3% Trehalose and 1% Leucine (no ID93, no Tris, 1/3 [GLA-SE]) INHALABLE | 7.1 | 176 | 3 | 0.24 | 3.8 | 0.0 | 5.66 | 0.02 | 191 |
| % loss | | -2.7% | -91.0% | | -467.4% | 12.3% | | 1.7% | | -4.4% |

The results in Table 4 show that the formulation containing leucine (LN-23-33) produced the best emitted dose from the inhaler, total lung deposition suggesting that less of the particles were lost in the mouth and throat (more particles made it to the lungs). This suggests that the formulation with leucine provided the best results for an aerosolized vaccine composition.

The methods used for characterization of the formulations for spray dried inhalables were performed as discussed in Example 2 with respect to the spray dry (dry powder)

The results in Table 5 show that LN-23-33, the inhalable formulation containing 1% leucine showed a doubling in the particle size upon reconstitution and that the sample was polydisperse. However, since the powder vaccine is envisioned to be used as a dry powder inhalable without reconstitution, this result is not likely to reduce the effectiveness. Further, the GLA content was roughly as expected given that the reconstitution volumes may not be exactly accurate. Thus, a thermostable inhalable adjuvant composition having the desired characteristics was successfully produced. The inhalable formulations LN-23-33 and LN-23-32 can be used to produce an exemplary inhalable formulation comprising an active amount of the antigen ID93 or another antigen. Other results with the spray dried formulation in Examples 1-3 showed that the addition of the antigen did not affect the particle size and stability. The ID93 content can be quantified using SDS-PAGE and ELISA. The total solid content is varied among different formulations containing ID93 by reducing the amount of trehalose, GMP, squalene, DMPC and/or leucine to keep the particle sizes suitable for inhalable delivery. Thus, the inhalable formulations in Example 4 can be used with an antigen, such as ID93 for inhalable vaccines.

ALTERNATIVES AND EXTENSIONS

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

REFERENCES

[1] R. Vehring, "Pharmaceutical Particle Engineering via Spray Drying," *Pharmaceutical Research*, vol. 25, no. 5, pp. 999-1022, 2007.

[2] C. Encina, C. Vergara, B. Gimenez, F. Oyarzun-Ampuero and P. Robert, "Conventional spray-drying and future trends for the microencapsulation of fish oil," *Trends in Food Science & Technolog*, vol. 56, pp. 46-60, 2016.

[3] S. Bertholet, G. C. Ireton, D. J. Ordway, H. Plessner Windish, S. O. Pine, M. Kahn, T. Phan, I. M. Orme, T. S. Vedvick, S. L. Baldwin, R. N. Coler and S. G. Reed, "A defined tuberculosis vaccine candidate boosts BCG and protects against multidrug-resistant Mycobaterium tuberculosis," *Science Translational Medicine*, vol. 2, no. 53, pp. 53-74, 2010.

[4] W. H. Organization, "Global Tuberculosis Report," World Health Organization, Geneva, 2018.

[5] R. N. Coler, T. A. Day, R. Ellis, F. M. Piazza, A. M. Beckmann, J. Vergara, T. Rolf, L. Lu, G. Alter, D. Hokey, L. Jayashankar, R. Walker, M. A. Snowden, T. Evans, A. Ginsberg and S. G. Reed, "The TLR-4 agonist adjuvant, GLA-SE, improves magnitude and quality of immune responses elicited by the ID93 tuberculosis vaccine: first-in-human trial," *Nature Partner Journals*, vol. 3, no. 34, 2018.

[6] C. B. Fox, R. C. Anderson, T. S. Dutill, Y. Goto, S. G. Reed and T. S. Vedvick, "Monitorung the effects of component structure and source on formulation stability and adjuvant activity of oil-in-water emulsions," *Colloids and Surfaces B; Biointerfaces*, vol. 65, pp. 98-105, 2008.

[7] A. G. Floyd, "Top ten considerations in the development of parenterial emulsions," *Pharmaceutical Science and Technology Today*, vol. 2, no. 4, pp. 134-143, 1999.

[8] R. M. Kramer, M. C. Archer, N. Dubois, N. Dubois Cauwelaert, E. A. Beebe, P.-w. D. Huang, Q. M. Dowling, A. M. Schwartz, D. M. Fedor, T. S. Vedvick and C. B. Fox, "Development of a thermostable nanoemulsion adjuvanted vaccine against tuberculosis using a design-of-experiments approach," *International Journal of Nanomedicine*, vol. 13, pp. 3689-3711, 2018.

[9] M. T. Orr, R. M. Kramer, L. V. Barnes, Q. M. Dowling, A. L. Desbien, E. A. Beebe, J. D. Laurance, C. B. Fox, S. G. Reed, R. N. Coler and T. S. Vedvick, "Elimination of the cold-chain dependance of a nanoemulsion adjuvant vaccine against tuberculois by lyophilization," *Journal of Controlled Release*, vol. 10, no. 177, pp. 20-26, 2014.

[10] H. Schwartzbach, "Achieving aseptic drying with spray drying technologies," *Pharmaceutical Technology Europe*, vol. 23, no. 9, 2011.

[11] International Conference On Harmonisation Of Technical Requirements For Registration Of Pharmaceuticals For Human Use, "ICH Harmonised Tripartite Guideline—Stability Testing of New Drug Substances and Products Q1A(R2)," ICH, 2003.

[12] S. Ohtake and J. Wang, "Trehalose: current use and future applications," *Journal of Pharmaceutical Sciences*, vol. 100, no. 6, pp. 2020-2053, 2011.

[13] D. Zhou, G. G. Zhang, D. Law, D. J. Grant and E. A. Schmitt, "Physical stability of amorphous pharmaceuticals: Importance of configurational thermodynamic quantities and molecular mobility," *Journal of Pharmaceutical Sciences*, vol. 91, no. 8, pp. 1863-1872, August 2000.

[14] M. Gordon and J. S. Taylor, "Ideal copolymers and the second-order transitions of synthetic rubbers. i. non-crystalline copolymers," *Journal of Applied Chemistry*, vol. 2, no. 9, pp. 493-500, September 1952.

[15] T. Chen, A. Fowler and M. Toner, "Literature review: supplemented phase diagram of the trehalose-water binary mixture," *Cryobiology*, vol. 40, no. 3, pp. 277-282, 200.

[16] H. A. Iglesias, J. Chirife and M. P. Buera, "Adsorption isotherm of amorphous trehalose," *Journal of the Science of Food and Agriculture*, vol. 75, no. 2, pp. 183-186, 26 Mar. 1999.

[17] K. D. Roe and T. P. Labuza, "Glass transition and crystallization of amorphous trehalose-sucrose mixtures," *International Journal of Food Properties*, vol. 8, no. 3, pp. 559-574, 2005.

[18] R. Vehring, W. R. Foss and D. Lechuga-Ballesteros, "Particle formation in spray drying," *Aerosol Science*, vol. 38, pp. 728-746, 2007.

[19] J. Ivey, P. Bhambri, D. Lewis, T. Church, W. Finlay and R. Vehring, "Dried corticosteroid particle formation from evaporating monodisperse propellant solution droplets," in *AAPS Annual Meeting and Exposition*, Denver, 2016.

[20] S. Hoe, J. W. Ivey, M. A. Boraey, A. Shamsaddini-Shahrbabak, E. Javaheri, M. Sadaf, W. H. Finlay and R. Vehring, "Use of a fundamental approach to spray-drying formulation design to facilitate the development of multi-component dry powder aerosols for respiratory drug delivery," *Pharmaceutical Research*, vol. 32, no. 2, pp. 449-465, February 2014.

[21] M. Y. Chan, Q. M. Dowling, S. J. Sivananthan and R. M. Kramer, "Particle sizing of nanoparticle adjuvant formulations by dynamic light scattering (DLS) and nanoparticle tracking analysis (NTA)," *Methods in Molecular Biology*, vol. 1494, pp. 239-252, 2017.

[22] H. Wang, D. Barona, S. Oladepo, L. Williams, S. Hoe, D. Lechuga-Ballesteros and R. Vehring, "Macro-Raman spectroscopy for bulk composition and homogeneity analysis of multi-component pharmaceutical powders," *Journal of Pharmaceutical and Biomedical Analysis*, vol. 141, pp. 180-191, 2017.

[23] C. Krogsgard Nielsen, J. Kjems, T. Mygind, T. Snabe, K. Schwarz, Y. Serfert and R. L. Meyer, "Enhancing the antibacterial efficacy of isoeugenol by emulsion encapsulation," *International Journal of Food Microbiology*, vol. 229, pp. 7-14, 2016.

[24] N. Mlalila, H. Swai, L. Kalombo and A. Hilonga, "Effects of spray-drying on w/o/w multiple emulsions prepared from a stearic acid matrix," *Nanotechnology, Science and Applications*, vol. 7, pp. 105-112, 2014.

[25] C. Lee and C. D. Bain, "Raman spectra of planar supported lipid bilayers," *Biochimica et Biophysica Acta*, vol. 1711, no. 1, pp. 59-71, June 2005.

[26] M. Bringas-Lantigua, I. Exposito-Molina, G. A. Reineccius, O. Lopez-Hernandez and J. A. Pino, "Influence of spray-dryer air temperatures on encapsulated mandarin oil," *Drying Technology*, vol. 29, no. 5, pp. 520-526, 2011.

[27] M. T. Orr, R. M. Kramer, L. V. Barnes, Q. M. Dowling, A. L. Desbien, E. A. Beebe, J. D. Laurance, C. B. Fox, S. G. Reed, R. N. Coler and T. S. Vedvick, "Elimination of the cold-chain dependence of a nanoemulsion adjuvanted vaccine against tuberculosis by lyophilization," PMCID: PMC3956454.

[28] R. M. Kramer, M. C. Archer, M. T. Orr, N. Dubois Cauwelaert, E. A. Beebe, P. D. Huang, Q. M. Dowling, A. M. Schwartz, D. M. Fedor, T. S. Vedvick, and C. B. Fox. "Development of a thermostable nanoemulsion adjuvanted vaccine against tuberculosis using a design-of-experiments approach," PMCID: PMC6028350.

TABLE 6

ID93sequences (SEQ ID Nos: 1-8)

SEQUENCES ID93 fusion polypeptide with optional His tag (SEQ ID NO: 1)
MGSSHHHHHHSSGLVPRGSHMTINYQFGDVDAHGAMIRAQAGSLEAEHQA
IISDVLTASDFWGGAGSAACQGFITQLGRNFQVIYEQANAHGQKVQAAGN
NMAQTDSAVGSSWAGTHLANGSMSEVMMSEIAGLPIPPIIHYGAIAYAPS
GASGKAWHQRTPARAEQVALEKCGDKTCKVVSRFTRCGAVAYNGSKYQGG
TGLTRRAAEDDAVNRLEGGRIVNWACNELMTSRFMTDPHAMRDMAGRFEV
HAQTVEDEARRMWASAQNISGAGWSGMAEATSLDTMTQMNQAFRNIVNML
HGVRDGLVRDANNYEQQEQASQQILSSVDINFAVLPPEVNSARIFAGAGL
GPMLAAASAWDGLAEELHAAAGSFASVTTGLAGDAWHGPASLAMTRAASP
YVGWLNTAAGQAAQAAGQARLAASAFEATLAATVSPAMVAANRTRLASLV
AANLLGQNAPAIAAAEAEYEQIWAQDVAAMFGYHSAASAVATQLAPIQEG
LQQQLQNVLAQLASGNLGSGNVGVGNIGNDNIGNANIGFGNRGDANIGIG
NIGDRNLGIGNTGNWNIGIGITGNGQIGFGKPANPDVLVVGNGGPGVTAL
VMGGTDSLLPLPNIPLLEYAARFITPVHPGYTATFLETPSQFFPFTGLNS
LTYDVSVAQGVTNLHTAIMAQLAAGNEVVVFGTSQSATIATFEMRYLQSL
PAHLRPGLDELSFTLTGNPNRPDGGILTRFGFSIPQLGFTLSGATPADAY
PTVDYAFQYDGVNDFPKYPLNVFATANAIAGILFLHSGLIALPPDLASGV
VQPVSSPDVLTTYILLPSQDLPLLVPLRAIPLLGNPLADLIQPDLRVLVE
LGYDRTAHQDVPSPFGLFPDVDWAEVAADLQQGAVQGVNDALSGLGLPPP
WQPALPRLFST ID93 fusion polypeptide (SEQ ID NO: 2)
MTINYQFGDVDAHGAMIRAQAGSLEAEHQAIISDVLTASDFWGGAGSAAC
QGFITQLGRNFQVIYEQANAHGQKVQAAGNNMAQTDSAVGSSWAGTHLAN
GSMSEVMMSEIAGLPIPPIIHYGAIAYAPSGASGKAWHQRTPARAEQVAL
EKCGDKTCKVVSRFTRCGAVAYNGSKYQGGTGLTRRAAEDDAVNRLEGGR
IVNWACNELMTSRFMTDPHAMRDMAGRFEVHAQTVEDEARRMWASAQNIS
GAGWSGMAEATSLDTMTQMNQAFRNIVNMLHGVRDGLVRDANNYEQQEQA
SQQILSSVDINFAVLPPEVNSARIFAGAGLGPMLAAASAWDGLAEELHAA
AGSFASVTTGLAGDAWHGPASLAMTRAASPYVGWLNTAAGQAAQAAGQAR
LAASAFEATLAATVSPAMVAANRTRLASLVAANLLGQNAPAIAAAEAEYE
QIWAQDVAAMFGYHSAASAVATQLAPIQEGLQQQLQNVLAQLASGNLGSG
NVGVGNIGNDNIGNANIGFGNRGDANIGIGNIGDRNLGIGNTGNWNIGIG
ITGNGQIGFGKPANPDVLVVGNGGPGVTALVMGGTDSLLPLPNIPLLEYA
ARFITPVHPGYTATFLETPSQFFPFTGLNSLTYDVSVAQGVTNLHTAIMA
QLAAGNEVVVFGTSQSATIATFEMRYLQSLPAHLRPGLDELSFTLTGNPN
RPDGGILTRFGFSIPQLGFTLSGATPADAYPTVDYAFQYDGVNDFPKYPL
NVFATANAIAGILFLHSGLIALPPDLASGVVQPVSSPDVLTTYILLPSQD
LPLLVPLRAIPLLGNPLADLIQPDLRVLVELGYDRTAHQDVPSPFGLFPD
VDWAEVAADLQQGAVQGVNDALSGLGLPPPWQPALPRLFST TABLE 6-continued ID93sequences (SEQ ID Nos: 1-8)

ID83 fusion polypeptide with optional His tag (SEQ ID NO: 3)
MGSSHHHHHHSSGLVPRGSHMGTHLANGSMSEVMMSEIAGLPIPPIIHYG
AIAYAPSGASGKAWHQRTPARAEQVALEKCGDKTCKVVSRFTRCGAVAYN
GSKYQGGTGLTRRAAEDDAVNRLEGGRIVNWACNELMTSRFMTDPHAMRD
MAGRFEVHAQTVEDEARRMWASAQNISGAGWSGMAEATSLDTMTQMNQAF
RNIVNMLHGVRDGLVRDANNYEQQEQASQQILSSVDINFAVLPPEVNSAR
IFAGAGLGPMLAAASAWDGLAEELHAAAGSFASVTTGLAGDAWHGPASLA
MTRAASPYVGWLNTAAGQAAQAAGQARLAASAFEATLAATVSPAMVAANR
TRLASLVAANLLGQNAPAIAAAEAEYEQIWAQDVAAMFGYHSAASAVATQ
LAPIQEGLQQQLQNVLAQLASGNLGSGNVGVGNIGNDNIGNANIGFGNRG
DANIGIGNIGDRNLGIGNTGNWNIGIGITGNGQIGFGKPANPDVLVVGNG
GPGVTALVMGGTDSLLPLPNIPLLEYAARFITPVHPGYTATFLETPSQFF
PFTGLNSLTYDVSVAQGVTNLHTAIMAQLAAGNEVVVFGTSQSATIATFE
MRYLQSLPAHLRPGLDELSFTLTGNPNRPDGGILTRFGFSIPQLGFTLSG
ATPADAYPTVDYAFQYDGVNDFPKYPLNVFATANAIAGILFLHSGLIALP
PDLASGVVQPVSSPDVLTTYILLPSQDLPLLVPLRAIPLLGNPLADLIQP
DLRVLVELGYDRTAHQDVPSPFGLFPDVDWAEVAADLQQGAVQGVNDALS
GLGLPPPWQPALPRLFST ID83 fusion polypeptide (SEQ ID NO: 4)
HLANGSMSEVMMSEIAGLPIPPIIHYGAIAYAPSGASGKAWHQRTPARAE
QVALEKCGDKTCKVVSRFTRCGAVAYNGSKYQGGTGLTRRAAEDDAVNRL
EGGRIVNWACNELMTSRFMTDPHAMRDMAGRFEVHAQTVEDEARRMWASA
QNISGAGWSGMAEATSLDTMTQMNQAFRNIVNMLHGVRDGLVRDANNYEQ
QEQASQQILSSVDINFAVLPPEVNSARIFAGAGLGPMLAAASAWDGLAEE
LHAAAGSFASVTTGLAGDAWHGPASLAMTRAASPYVGWLNTAAGQAAQAA
GQARLAASAFEATLAATVSPAMVAANRTRLASLVAANLLGQNAPAIAAAE
AEYEQIWAQDVAAMFGYHSAASAVATQLAPIQEGLQQQLQNVLAQLASGN
LGSGNVGVGNIGNDNIGNANIGFGNRGDANIGIGNIGDRNLGIGNTGNWN
IGIGITGNGQIGFGKPANPDVLVVGNGGPGVTALVMGGTDSLLPLPNIPL
LEYAARFITPVHPGYTATFLETPSQFFPFTGLNSLTYDVSVAQGVTNLHT
AIMAQLAAGNEVVVFGTSQSATIATFEMRYLQSLPAHLRPGLDELSFTLT
GNPNRPDGGILTRFGFSIPQLGFTLSGATPADAYPTVDYAFQYDGVNDFP
KYPLNVFATANAIAGILFLHSGLIALPPDLASGVVQPVSSPDVLTTYILL
PSQDLPLLVPLRAIPLLGNPLADLIQPDLRVLVELGYDRTAHQDVPSPFG
LFPDVDWAEVAADLQQGAVQGVNDALSGLGLPPPWQPALPRLFST Rv1813 (SEQ ID NO: 5)
MITNLRRRTAMAAAGLGAALGLGILLVPTVDAHLANGSMSEVMMSEIAGL
PIPPIIHYGAIAYAPSGASGKAWHQRTPARAEQVALEKCGDKTCKVVSRF
TRCGAVAYNGSKYQGGTGLTRRAAEDDAVNRLEGGRIVNWACN Rv3620 (SEQ ID NO: 6)
MTSRFMTDPHAMRDMAGRFEVHAQTVEDEARRMWASAQNISGAGWSGMAE
ATSLDTMTQMNQAFRNIVNMLHGVRDGLVRDANNYEQQEQASQQILSS Rv2608 (SEQ ID NO: 7)
MNFAVLPPEVNSARIFAGAGLGPMLAAASAWDGLAEELHAAAGSFASVTT
GLAGDAWHGPASLAMTRAASPYVGWLNTAAGQAAQAAGQARLAASAFEAT
LAATVSPAMVAANRTRLASLVAANLLGQNAPAIAAAEAEYEQIWAQDVAA
MFGYHSAASAVATQLAPIQEGLQQQLQNVLAQLASGNLGSGNVGVGNIGN
DNIGNANIGFGNRGDANIGIGNIGDRNLGIGNTGNWNIGIGITGNGQIGF
GKPANPDVLVVGNGGPGVTALVMGGTDSLLPLPNIPLLEYAARFITPVHP
GYTATFLETPSQFFPFTGLNSLTYDVSVAQGVTNLHTAIMAQLAAGNEVV
VFGTSQSATIATFEMRYLQSLPAHLRPGLDELSFTLTGNPNRPDGGILTR
FGFSIPQLGFTLSGATPADAYPTVDYAFQYDGVNDFPKYPLNVFATANAI
AGILFLHSGLIALPPDLASGVVQPVSSPDVLTTYILLPSQDLPLLVPLRA
IPLLGNPLADLIQPDLRVLVELGYDRTAHQDVPSPFGLFPDVDWAEVAAD
LQQGAVQGVNDALSGLGLPPPWQPALPRLF Rv3619 (SEQ ID NO: 8)
MTINYQFGDVDAHGAMIRAQAGSLEAEHQAIISDVLTASDFWGGAGSAAC
QGFITQLGRNFQVIYEQANAHGQKVQAAGNNMAQTDSAVGSSWA

The invention claimed is:

1. A spray-dried composition in the form of a dry powder, comprising an effective amount of an attenuated lipid A derivative (ALD), a gel-microparticle comprising squalene, wherein the squalene is present in an oil-in-water emulsion that is liquid at room temperature and trehalose, wherein a particle size of the dry powder has a particle size diameter of less than about 120 µm and the dry powder is formed by spray drying with an outlet relative humidity of less than 10%.

2. The composition of claim 1, wherein the composition is a vaccine comprising an effective amount of an antigen.

3. The composition of claim 1, wherein the particle size of the dry powder has a diameter of less than about 20 µm.

4. The composition of claim 1, wherein the composition is thermostable at a temperature between about 8° C. to about 60° C. for at least 1 month.

5. The composition of claim 4, wherein the composition is thermostable for at least 3 months.

6. The composition of claim 1, further comprising 1,2-dimyristoyl-sn-glycero-3-phosphocholine (DMPC), 1-palmitoyl-2-oleoyl-sn-glycerol-3-phosphocholine (POPC), 1,2-dioleoyl-sn-glycero-3-phosphocholine (DOPC), Dipalmitoylphosphatidylcholine (DSPC), egg PC, lecithin, polysorbate, or a combination thereof.

7. The composition of claim 1, wherein the ALD is monophosphoryl lipid A (MPL), 3d-MPL, or glucopyranosyl lipid adjuvant (GLA).

8. The composition of claim 1, wherein the composition is inhalable.

9. The composition of claim 2, wherein the antigen is a polypeptide, a nucleic acid encoding a polypeptide, or a pathogen.

10. The composition of claim 8, wherein the particle size of the dry powder has a diameter of less than about 20 µm.

11. The composition of claim 10, wherein the particle size has a diameter of less than about 10 µm.

12. The composition of claim 11, wherein the particle size has a diameter of 100 nm-300 nm.

13. The composition of claim 8, wherein the composition is thermostable at a temperature between about 8° C. to about 60° C. for at least 1 month.

14. The composition of claim 8, further comprising a shell formed from a shell former.

15. The composition of claim 14, wherein the shell former is leucine.

16. The composition of claim 8, further comprising 1,2-dimyristoyl-sn-glycero-3-phosphocholine (DMPC), 1-palmitoyl-2-oleoyl-sn-glycerol-3-phosphocholine (POPC), 1,2-dioleoyl-sn-glycero-3-phosphocholine (DOPC), Dipalmitoylphosphatidylcholine (DSPC), egg PC, lecithin, polysorbate, or a combination thereof.

17. A method for generating a thermostable dry powder vaccine composition, comprising the step of spray drying, in a spray dryer using an atomization gas, an oil-in-water emulsion to obtain a dry powder at process parameters such that the dry powder comprises gel-microparticles, wherein the oil-in-water emulsion comprises (1) an antigen, (2) qualene, (3) trehalose, (4) an attenuated lipid A derivative (ALD), and (5) a shell-former.

18. The method of claim 17, further comprising, packaging the thermostable dry powder vaccine composition in an aluminum bag with a dessicant pouch and double heat-sealing.

19. The method of claim 17, the oil-in-water emulsion further comprising 1,2-dimyristoyl-sn-glycero-3-phosphocholine (DMPC), 1-palmitoyl-2-oleoyl-sn-glycerol-3-phosphocholine (POPC), 1,2-dioleoyl-sn-glycero-3-phosphocholine (DOPC), Dipalmitoylphosphatidylcholine (DSPC), egg PC, lecithin, polysorbate, or a combination thereof.

20. The method of claim 17, wherein the process parameters include an atomizing gas pressure of 10 psi, an atomizing gas flow rate of 0.6 mL/min, and a drying gas flow rate of 200 SLPM (standard liters per minute).

21. A method of administering the composition of claim 1 to a subject, comprising administering the spray-dried composition via inhalation or respiratory delivery of the dry powder.

22. The method of claim 21, wherein the respiratory delivery is via the nasal or pulmonary route.

23. A method of administering the spray-dried composition of claim 1 to a subject, comprising (1) reconstituting the dry powder with an aqueous diluent and (2) administering the reconstituted dry powder via a parenteral route.

24. A method of treating a disease with a respiratory component, comprising administering the spray-dried vaccine composition of claim 2 via inhalation of the dry powder.

25. The method of claim 24 wherein the disease with a respiratory component is Tuberculosis (TB), Influenza (flu), Respiratory syncytial virus infection (RSV), or lung cancer.

26. The composition of claim 1, wherein the dry powder has an approximately 2-3% moisture content.

27. The composition of claim 1, wherein the spray-dried composition exhibits colloidal stability as measured by a droplet size of the oil-in-water emulsion following reconstitution of the dry powder being not significantly different than a droplet size of the oil-in-water emulsion before spray drying.

28. The composition of claim 27, wherein the droplet size of the oil-in-water emulsion both before spray drying and after reconstitution is about 100 nm.

29. The composition of claim 1, wherein the spray-dried composition exhibits colloidal stability as measured by a polydispersity index (PDI) of the oil-in-water emulsion following reconstitution of the dry powder being not significantly different than a PDI of the oil-in-water emulsion before spray drying.

30. The method of claim 17, wherein the process parameters include an outlet temperature of about 36° C.

31. The method of claim 17, wherein the process parameters include an outlet relative humidity of about 7%.

32. The method of claim 17, wherein the ALD is monophosphoryl lipid A (MPL), 3d-MPL, or glucopyranosyl lipid adjuvant (GLA).

33. The composition of claim 1, wherein the composition is thermostable at a temperature about 40° C. for at least 3 months.

34. The composition of claim 1, wherein the outlet relative humidity is about 7%.

35. The composition of claim 1, wherein the dry powder is formed by spray drying with an outlet temperature of about 36° C.

36. The composition of claim 1, wherein the outlet relative humidity is about 7% and wherein the dry powder is formed by spray drying with an outlet temperature of about 36° C.

* * * * *